(12) United States Patent
Tully et al.

(10) Patent No.: US 7,939,547 B2
(45) Date of Patent: May 10, 2011

(54) COMPOUNDS AND COMPOSITIONS AS CHANNEL ACTIVATING PROTEASE INHIBITORS

(75) Inventors: David C. Tully, San Diego, CA (US); Arnab K. Chatterjee, Encinitas, CA (US); Hank Michael James Petrassi, Cardiff, CA (US); Badry Bursulaya, San Diego, CA (US); Glen Spraggon, San Diego, CA (US)

(73) Assignee: IRM LLC, Hamilton (BM)

( * ) Notice: Subject to any disclaimer, the term of this patent is extended or adjusted under 35 U.S.C. 154(b) by 1003 days.

(21) Appl. No.: 11/749,001

(22) Filed: May 15, 2007

(65) Prior Publication Data
US 2007/0276002 A1    Nov. 29, 2007

Related U.S. Application Data

(60) Provisional application No. 60/808,014, filed on May 23, 2006, provisional application No. 60/860,622, filed on Nov. 22, 2006.

(51) Int. Cl.
*A61K 31/454* (2006.01)
*C07D 403/02* (2006.01)
(52) U.S. Cl. ........ 514/326; 524/342; 524/397; 524/422; 524/423; 546/207; 546/220.9; 546/279.1; 548/311.1; 548/517; 548/527; 548/530
(58) Field of Classification Search ................. 514/326, 514/342, 397, 422, 423; 546/207, 220.9, 546/279.1; 548/311.1, 517, 527, 530
See application file for complete search history.

(56) References Cited

U.S. PATENT DOCUMENTS
6,469,036 B1 * 10/2002 Costanzo et al. ............. 514/359

FOREIGN PATENT DOCUMENTS

| WO | WO 96/40748    | 12/1996 |
|----|----------------|---------|
| WO | WO 97/31939    | 9/1997  |
| WO | WO 98/07308    | 2/1998  |
| WO | WO 2005/023804 | 3/2005  |
| WO | WO 2005/076886 | 8/2005  |

OTHER PUBLICATIONS

Costanzo, et al., "Potent, Small-Molecule Inhibitors of Human Mast cell Tryptase. Antiasthmatic Action of a Dipeptide-Based Transition-State Analogue Containing a Benzothiazole Ketone", *J. Med. Chem.*, vol. 46, pp. 3865-3876, 2003.
Donnelly, et al., "Therapy for chronic Obstructive Pulmonary Disease in the 21st Century", *Drugs*, vol. 63, No. 19, 2003, pp. 1973-1998.
Edwards, et al., "Discovery and Biological Activity of Orally Active Petidyl Trifluoromethyl Ketone Inhibitors of Human Neutrophil Elastase", *J. Med. Chem.* 1997 vol. 40, pp. 1876-1885.

* cited by examiner

*Primary Examiner* — Celia Chang
(74) *Attorney, Agent, or Firm* — Emily Tongco Wu; Genomics Institute of the Novartis Research Foundation

(57) ABSTRACT

The invention provides compounds and pharmaceutical compositions thereof, which are useful for modulating channel activating proteases, and methods for using such compounds to treat, ameliorate or prevent a condition associated with a channel activating protease, including but not limited to prostasin, PRSS22, TMPRSS11 (e.g., TMPRSS11B, TMPRSS11E), TMPRSS2, TMPRSS3, TMPRSS4 (MTSP-2), matriptase (MTSP-1), CAP2, CAP3, trypsin, cathepsin A, or neutrophil elastase.

17 Claims, No Drawings

COMPOUNDS AND COMPOSITIONS AS CHANNEL ACTIVATING PROTEASE INHIBITORS

CROSS REFERENCE TO RELATED APPLICATIONS

This application claims the benefit of U.S. provisional applications Ser. No. 60/808,014, filed 23 May 2006; and Ser. No. 60/860,622, filed 22 Nov. 2006. Each of these applications is incorporated herein by reference in its entirety.

TECHNICAL FIELD

The invention generally relates to channel activating protease (CAP) inhibitors.

BACKGROUND ART

Prostasin is a trypsin-like serine protease that is present in a variety of mammalian tissues. It is a membrane anchored protease that is expressed on the extra-cellular membrane of cells, but may also be secreted into body fluids such as semen, urine and airway surface liquid. Prostasin (PRSS8), together with proteases such as matriptase, CAP2, CAP3, trypsin, PRSS22, TMPRSS11, cathepsin A, and neutrophil elastase, may stimulate the activity of the amiloride-sensitive epithelial sodium channel (ENaC). Inhibiting these enzymes may induce changes in epithelial ion transport and therefore fluid homeostasis across epithelial membranes. For example, CAP inhibition in the kidney is thought to promote diuresis, whilst CAP inhibition in the airways promotes the clearance of mucus and sputum in lung. CAP inhibition in the kidney may therefore be used therapeutically to treat hypertension. CAP inhibition in the airways prevents the stagnation of respiratory secretions that otherwise tends to make sufferers vulnerable to secondary bacterial infections.

DISCLOSURE OF THE INVENTION

The invention provides compounds, pharmaceutical compositions and methods of using such compounds for modulating channel activating proteases (CAP). For example, the compounds and compositions of the invention may be used for modulating prostasin, PRSS22, TMPRSS11 (e.g., TMPRSS11B, TMPRSS11E), TMPRSS2, TMPRSS3, TMPRSS4 (MTSP-2), matriptase (MTSP-1), CAP2, CAP3, trypsin, cathepsin A, and neutrophil elastase.

In one aspect, the present invention provides compounds of Formula (1):

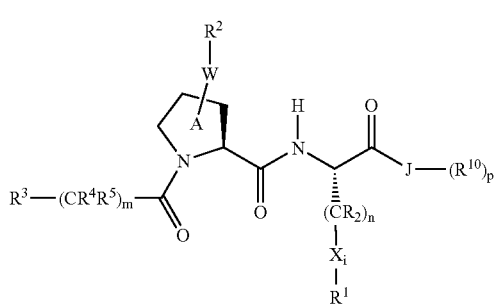

and pharmaceutically acceptable salts, hydrates, solvates and stereoisomers thereof, wherein J is a 5-12 membered monocyclic or fused carbocyclic ring, aryl, heteroaryl or heterocyclic ring containing N, O and/or S;

$R^1$ is —$(CR_2)_l$—$NR_2$, —$(CR_2)_l$—NRC($=$NR)—$NR_2$, —$(CR_2)_l$—C($=$NR)—$NR_2$ or a 5-7 membered nitrogen-containing non-aromatic heterocyclic ring;

W—$R^2$ is a substituent at any position on ring A;

W is or —O($CR_2)_k$—, —S($CR_2)_k$—, —S(O)($CR_2)_k$—, —$SO_2(CR_2)_k$— or —OC(O)($CR_2)_k$—;

$R^2$ is $C_{1-6}$ alkyl, $C_{2-6}$ alkenyl, $C_{2-6}$ alkynyl, $R^6$, —$CR^9$=$CR^9$—$R^6$, or

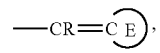

wherein ring E is an optionally substituted 5-7 membered monocyclic or fused carbocyclic or heterocyclic ring; or W—$R^2$ together form $C_{1-6}$ alkyl, a 5-7 membered aryl or —OC(O)$NR^7R^8$;

$R^3$ is $NR^7R^8$ or $R^6$;

$R^4$ and $R^5$ are independently H, $C_{1-6}$ alkyl, OH, or $C_{1-6}$ alkoxy;

$R^7$ and $R^8$ are independently H, $C_{1-6}$ alkyl, $C_{2-6}$ alkenyl, $C_{2-6}$ alkynyl or —$(CR_2)_l$—$R^6$; or $R^7$ and $R^8$ together with N may form an optionally substituted 5-7 membered monocyclic or fused heterocyclic ring;

$R^9$ is H or $C_{1-6}$ alkyl;

$R^{10}$ is halo, $C_{1-6}$ alkyl, $C_{1-6}$ alkoxy, $OR^{11}$ or —$(CR_2)_l$—$R^{11}$;

$R^6$, $R^{11}$ and X are independently an optionally substituted 5-7 membered carbocyclic ring, heterocyclic ring, aryl or heteroaryl; or $R^{11}$ is H or $C_{1-6}$ alkyl;

each R is H, or $C_{1-6}$ alkyl, $C_{2-6}$ alkenyl, or $C_{2-6}$ alkynyl, wherein a carbon may optionally be substituted or replaced with NR, O or S;

i is 0-1;

k and l are independently 0-6;

m and n are independently 1-6; and p is 0-3.

In the above Formula (1), $R^1$ is —$(CH_2)_l$—$NH_2$, —$(CH_2)_l$—NHC($=$NH)—$NH_2$ or —$(CH_2)_l$—C($=$NH)—$NH_2NH_2$, wherein each l is 0-1; or $R^1$ is piperidinyl. In particular examples, $R^1$ is —$(CH_2)_l$—$NH_2$, —$(CH_2)_l$—NHC($=$NH)—$NH_2$ or —$(CH_2)_l$—C($=$NH)—$NH_2NH_2$.

In the above Formula (1), W is —O($CR_2)_k$—, —S($CR_2)_k$—, —S(O)($CR_2)_k$—, —$SO_2(CR_2)_k$— or —OC(O)($CR_2)_k$—; and k is 1. In particular examples, W is —O($CR_2)_k$—.

In some embodiments, $R^2$ is an optionally substituted phenyl, $C_{5-7}$ cycloalkyl, thienyl, furanyl, piperidinyl, methylenecyclohexyl,

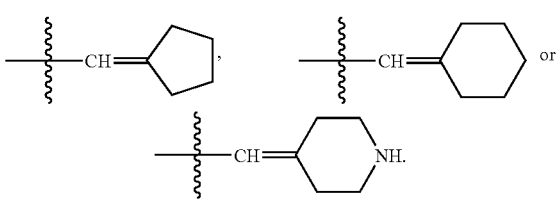

In particular examples, $R^2$ is phenyl or $C_{5-7}$ cycloalkyl.

In other embodiments, $R^3$ is an optionally substituted phenyl, pyridyl, thiazolyl, piperidinyl, or $NR^7R^8$; wherein $R^7$ and $R^8$ are both H, or $R^7$ and $R^8$ together with N form an optionally substituted piperidinyl. In some examples, R, $R^4$, $R^5$, $R^7$ and $R^8$ are each H.

In yet other embodiments, $R^6$ is an optionally substituted phenyl, $C_{3-7}$ cycloalkyl, pyridyl, thiazolyl, piperidinyl, cyclohexanol, imidazolyl, thienyl, furanyl,

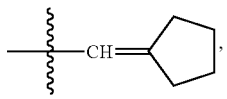 , 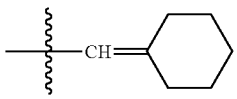 or

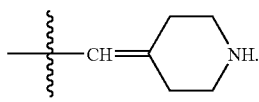

In particular examples, $R^6$ is an optionally substituted phenyl, $C_{3-7}$ cycloalkyl, pyridyl, thiazolyl or piperidinyl.

In yet other embodiments, X is cyclohexyl, phenyl or piperidinyl, each of which may be optionally substituted with $C_{1-6}$ alkyl, $C_{1-6}$ alkoxy, halo, or a combination thereof. In some examples, X is cyclohexyl or phenyl.

In the above Formula (1), $-J-(R^{10})_p$ together may be

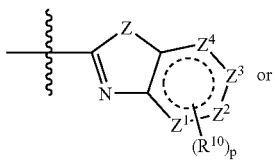 or 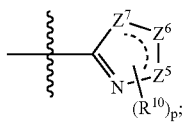

Z is O or S;

$Z^1$, $Z^2$, $Z^3$ or $Z^4$ are independently N, CH, or C when attached to $R^{10}$;

$Z^5$, $Z^6$ or $Z^7$ are independently N, O, S, CH, or C when attached to $R^{10}$;

$R^{10}$ is $C_{1-6}$ alkyl or $—(CR_2)_l—R^{11}$;

$R^{11}$ is phenyl or $C_{5-7}$ cycloalkyl; and p is 0-1.

In some examples, J is benzothiazolyl, benzoxazolyl, thiazolyl, or oxadiazolyl.

In one embodiment, the invention provides compounds of Formula (2A) or (2B):

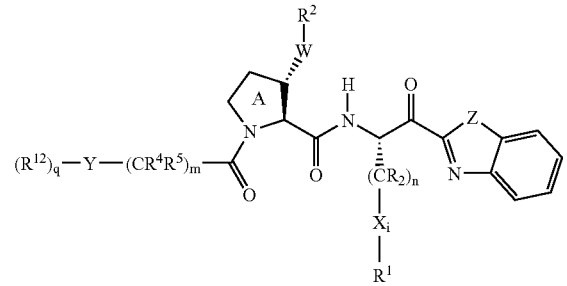

(2A)

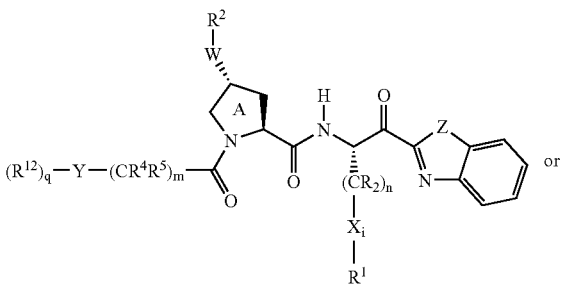

(2B)

wherein Z is O or S;
$R^1$ is $NH_2$, $—NHC(=NH)—NH_2$ or $—C(=NH)—NH_2$;
W is $—O(CH_2)_k—$ or $—S(O)(CH_2)_k—$;
$R^2$ is an optionally substituted phenyl, or $W—R^2$ together form $C_{1-6}$ alkyl or an optionally substituted phenyl;
R, $R^4$ and $R^5$ are independently H;
Y is a 5-7 membered aryl, heteroaryl or heterocyclic ring containing N, O or S;
$R^{12}$ is halo, $C_{1-6}$ alkyl or $-L-(CH_2)_l—R^{13}$;
L is a bond, O, $SO_2$, NHCO, $NHSO_2$ or $SO_2NH$;
$R^{13}$ is optionally halogenated $C_{1-6}$ alkyl, or an optionally substituted $C_{3-7}$ cycloalkyl, or 5-7 membered aryl, heteroaryl or heterocyclic ring;
i is 0;
k is 1;
l is 0-1;
m and n are independently 1-4; and
q is 0-3.

In the above Formula (2A) or (2B), Y may be phenyl, pyridyl, thiazolyl or piperidinyl. In some examples, $R^{12}$ is $-L-(CH_2)_l—R^{13}$; and $R^{13}$ is an optionally halogenated $C_{1-6}$ alkyl, $C_{3-7}$ cycloalkyl, morpholinyl, phenyl or piperidinyl.

In another aspect, the present invention provides pharmaceutical compositions comprising a compound having Formula (1), (2A) or (2B), and a pharmaceutically acceptable excipient.

The invention also provides methods for modulating a channel activating protease, comprising administering to a system or a subject in need thereof, a therapeutically effective amount of a compound having Formula (1), (2A) or (2B), or pharmaceutically acceptable salts or pharmaceutical compositions thereof, thereby modulating said channel activating protease.

In yet another aspect, the invention provides methods for ameliorating a condition mediated by a channel activating protease, comprising administering to a system or subject in need of such treatment an effective amount of a compound having Formula (1), (2A) or (2B), or pharmaceutically acceptable salts or pharmaceutical compositions thereof, and optionally in combination with a second therapeutic agent, thereby treating said condition. Examples of a second therapeutic agent which may be used with the compounds of the invention include but are not limited to an anti-inflammatory, bronchodilatory, antihistamine, anti-tussive, antibiotic or DNase.

Examples of channel activating protease which may be modulated using the compounds of the invention include but are not limited to prostasin, PRSS22, TMPRSS11 (e.g., TMPRSS11B, TMPRSS11E), TMPRSS2, TMPRSS3, TMPRSS4 (MTSP-2), matriptase (MTSP-1), CAP2, CAP3, trypsin, cathepsin A, or neutrophil elastase. In particular examples, the invention provides methods for modulating prostasin, or methods for treating a condition mediated by prostasin.

In the above methods for using the compounds of the invention, a compound having Formula (1), (2A) or (2B) may be administered to a system comprising cells or tissues. For example, a compound having Formula (1), (2A) or (2B) may be contacted with bronchial epithelial cells, which may be human cells. In other embodiments, a compound having Formula (1), (2A) or (2B) may be administered to a human or animal subject.

In one embodiment, the invention provides methods for ameliorating a condition associated with the movement of fluid across ion transporting epithelia or the accumulation of mucus and sputum in respiratory tissues, or a combination thereof. For example, the condition may be cystic fibrosis, primary ciliary dyskinesia, lung carcinoma, chronic bronchitis, chronic obstructive pulmonary disease, asthma or a respiratory tract infection.

Furthermore, the present invention provides the use of a compound of Formula (1), (2A) or (2B), or pharmaceutically acceptable salts or pharmaceutical compositions thereof, and optionally in combination with a second therapeutic agent, for modulating a channel activating protease (e.g., for inhibiting prostasin). The present invention also provides the use of a compound having Formula (1), (2A) or (2B), or pharmaceutically acceptable salts or pharmaceutical compositions thereof, and optionally in combination with a second therapeutic agent, in the manufacture of a medicament for treating a condition mediated by a channel activating protease (e.g., a prostasin-mediated condition).

DEFINITIONS

"Alkyl" refers to a moiety and as a structural element of other groups, for example halo-substituted-alkyl and alkoxy, and may be straight-chained or branched. An optionally substituted alkyl, alkenyl or alkenyl as used herein may be optionally halogenated (e.g., $CF_3$), or may have one or more carbons that is substituted or replaced with a heteroatom, such as NR, O or S (e.g., —$OCH_2CH_2O$—, alkylthiols, thioalkoxy, alkylamines, etc).

"Aryl" refers to a monocyclic or fused bicyclic aromatic ring containing carbon atoms. For example, aryl may be phenyl or naphthyl. "Arylene" means a divalent radical derived from an aryl group.

"Heteroaryl" as used herein is as defined for aryl above, where one or more of the ring members is a heteroatom. Examples of heteroaryls include but are not limited to pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

A "carbocyclic ring" as used herein refers to a saturated or partially unsaturated, monocyclic, fused bicyclic or bridged polycyclic ring containing carbon atoms, which may optionally be substituted, for example, with =O. Examples of carbocyclic rings include but are not limited to cyclopropyl, cyclobutyl, cyclopentyl, cyclohexyl, cyclopropylene, cyclohexanone, etc.

A "heterocyclic ring" as used herein is as defined for a carbocyclic ring above, wherein one or more ring carbons is a heteroatom. For example, a heterocyclic ring may contain N, O, S, —N=, —S—, —S(O), —$S(O)_2$—, or —NR— wherein R may be hydrogen, $C_{1-4}$alkyl or a protecting group. Examples of heterocyclic rings include but are not limited to morpholino, pyrrolidinyl, pyrrolidinyl-2-one, piperazinyl, piperidinyl, piperidinylone, 1,4-dioxa-8-aza-spiro[4.5]dec-8-yl, etc.

The terms "co-administration" or "combined administration" or the like as used herein are meant to encompass administration of the selected therapeutic agents to a single patient, and are intended to include treatment regimens in which the agents are not necessarily administered by the same route of administration or at the same time.

The term "pharmaceutical combination" as used herein refers to a product obtained from mixing or combining active ingredients, and includes both fixed and non-fixed combinations of the active ingredients. The term "fixed combination" means that the active ingredients, e.g. a compound of Formula (1), (2A) or (2B) and a co-agent, are both administered to a patient simultaneously in the form of a single entity or dosage. The term "non-fixed combination" means that the active ingredients, e.g. a compound of Formula (1), (2A) or (2B) and a co-agent, are both administered to a patient as separate entities either simultaneously, concurrently or sequentially with no specific time limits, wherein such administration provides therapeutically effective levels of the active ingredients in the body of the patient. The latter also applies to cocktail therapy, e.g. the administration of three or more active ingredients.

The term "therapeutically effective amount" means the amount of the subject compound that will elicit a biological or medical response in a cell, tissue, organ, system, animal or human that is being sought by the researcher, veterinarian, medical doctor or other clinician.

The term "administration" and or "administering" of the subject compound should be understood to mean as providing a compound of the invention and prodrugs thereof, to the individual in need of treatment.

As used herein, the terms "treat", "treating" and "treatment" refer to a method of alleviating or abating a disease and/or its attendant symptoms.

The term "prostasin" may also be referred to as: human channel-activating protease (hCAP); channel-activating protease-1; and PRSS8, MERPOPS ID S01.159.

MODES OF CARRYING OUT THE INVENTION

The invention provides compounds, pharmaceutical compositions and methods of using such compounds for modulating channel activating proteases (CAP).

In one aspect, the present invention provides compounds of Formula (1):

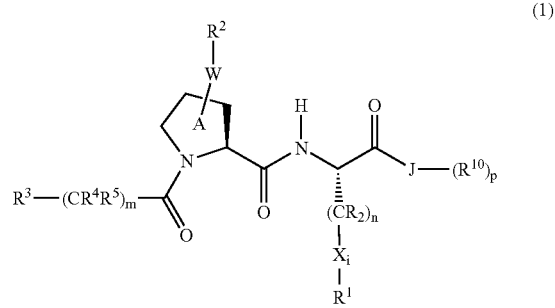

and pharmaceutically acceptable salts, hydrates, solvates and stereoisomers thereof, wherein J is a 5-12 membered monocyclic or fused carbocyclic ring, aryl, heteroaryl or heterocyclic ring containing N, O and/or S;

$R^1$ is —$(CR_2)_l$—$NR_2$, —$(CR_2)_l$—NRC(=NR)—$NR_2$, —$(CR_2)_l$—C(=NR)—$NR_2$ or a 5-7 membered nitrogen-containing non-aromatic heterocyclic ring;

W—$R^2$ is a substituent at any position on ring A;

W is or —$O(CR_2)_k$—, —$S(CR_2)_k$—, —$S(O)(CR_2)_k$—, —$SO_2(CR_2)_k$— or —$OC(O)(CR_2)_k$—;

$R^2$ is $C_{1-6}$ alkyl, $C_{2-6}$ alkenyl, $C_{2-6}$ alkynyl, $R^6$, —$CR^9$=$CR^9$—$R^6$, or $$—CR=C\underset{E}{\overset{}{\underbrace{\phantom{xxx}}}},$$

wherein ring E is an optionally substituted 5-7 membered monocyclic or fused carbocyclic or heterocyclic ring; or W—$R^2$ together form $C_{1-6}$ alkyl, a 5-7 membered aryl or —$OC(O)NR^7R^8$;

$R^3$ is $NR^7R^8$ or $R^6$;

$R^4$ and $R^5$ are independently H, $C_{1-6}$ alkyl, OH, or $C_{1-6}$ alkoxy;

$R^7$ and $R^8$ are independently H, $C_{1-6}$ alkyl, $C_{2-6}$ alkenyl, $C_{2-6}$ alkynyl or —$(CR_2)_l$—$R^6$; or $R^7$ and $R^8$ together with N may form an optionally substituted 5-7 membered monocyclic or fused heterocyclic ring;

$R^9$ is H or $C_{1-6}$ alkyl;

$R^{10}$ is halo, $C_{1-6}$ alkyl, $C_{1-6}$ alkoxy, $OR^{11}$ or —$(CR_2)_l$—$R^{11}$;

$R^6$, $R^{11}$ and X are independently an optionally substituted 5-7 membered carbocyclic ring, heterocyclic ring, aryl or heteroaryl; or $R^{11}$ is H or $C_{1-6}$ alkyl;

each R is H, or $C_{1-6}$ alkyl, $C_{2-6}$ alkenyl, or $C_{2-6}$ alkynyl, wherein a carbon may optionally be substituted or replaced with NR, O or S;

i is 0-1;

k and l are independently 0-6;

m and n are independently 1-6; and p is 0-3.

In one embodiment, the invention provides compounds of Formula (2A) or (2B):

(2A)

(2B)

wherein Z is O or S;

$R^1$ $NH_2$, —NHC(=NH)—$NH_2$ or —C(=NH)—$NH_2$;

W is —$O(CH_2)_k$— or —$S(O)(CH_2)_k$—;

$R^2$ is an optionally substituted phenyl, or W—$R^2$ together form $C_{1-6}$ alkyl or an optionally substituted phenyl;

R, $R^4$ and $R^5$ are independently H;

Y is a 5-7 membered aryl, heteroaryl or heterocyclic ring containing N, O or S;

$R^{12}$ is halo, $C_{1-6}$ alkyl or -L-$(CH_2)_l$—$R^{13}$;

L is a bond, O, $SO_2$, NHCO, $NHSO_2$ or $SO_2NH$;

$R^{13}$ is optionally halogenated $C_{1-6}$ alkyl, or an optionally substituted $C_{3-7}$ cycloalkyl, or 5-7 membered aryl, heteroaryl or heterocyclic ring;

i is 0;

k is 1;

l is 0-1;

m and n are independently 1-4; and q is 0-3.

In each of the above formula, X, $R^8$ and $R^9$ may alternatively be an optionally substituted $C_{3-7}$ cycloalkyl.

In each of the above formula, $R^1$ may be NR'R", NH—C(NR'R")=NH, NH—C(NHR')=NR", NH—C(R')=NR", S—C(NR'R")—NH, S—C(NHR')—NR", C(NR'R")=NH, C(NHR')=NR" or CR=NR"; where R'R" are the same or different and are H, $C_{1-6}$ alkyl, $C_{1-3}$ arylalkyl, aryl or where R'R" forms a cyclic ring containing $(CH_2)_p$ where p is an integer from 2 to 5.

In each of the above formula, each optionally substituted moiety may be substituted with halo, =O, amino, guanidinyl, amidino, $C_{1-6}$ alkoxy; $C_{1-6}$ alkyl, $C_{2-6}$ alkenyl or $C_{2-6}$ alkynyl, each of which may optionally be halogenated or may optionally have a carbon that may be replaced or substituted with N, O or S; $CO_2R^{11}$, O—$(CR_2)_m$—C(O)—$R^{11}$; —$(CR_2)_m$—$R^{11}$, —$(CR_2)_m$—C(O)—$R^{11}$, or —$(CR_2)_m$—$SO_2$—$R^{11}$; or a combination thereof, wherein each $R^{11}$ is H, $C_{1-6}$ alkyl, or an optionally substituted carbocyclic ring, heterocyclic ring, aryl or heteroaryl.

The compounds and compositions of the invention may be useful for modulating a channel activating protease. Examples of channel activating proteases which may be modulated using the compounds and compositions of the invention include but are not limited to prostasin, PRSS22, TMPRSS11 (e.g., TMPRSS11B, TMPRSS11E), TMPRSS2, TMPRSS3, TMPRSS4 (MTSP-2), matriptase (MTSP-1), CAP2, CAP3, trypsin, cathepsin A, or neutrophil elastase. The novel compounds of this invention may also inhibit the activity of proteases that stimulate the activity of ion channels, such as the epithelial sodium channel, and may be useful in the treatment of CAP-associated diseases.

Pharmacology and Utility

Compounds of the invention modulate the activity of channel activating protease, for example, trypsin-like serine proteases such as prostasin, and as such, are useful for treating diseases or disorders in which prostasin contributes to the pathology and/or symptomology of the disease.

Diseases mediated by inhibition of a channel activating protease, for example, by a trypsin-like serine protease such as prostasin, include diseases associated with the regulation of fluid volumes across epithelial membranes. For example, the volume of airway surface liquid is a key regulator of mucociliary clearance and the maintenance of lung health. The inhibition of a channel activating protease will promote fluid accumulation on the mucosal side of the airway epithelium, thereby promoting mucus clearance and preventing the accumulation of mucus and sputum in respiratory tissues (including lung airways). Such diseases include respiratory diseases such as cystic fibrosis, primary ciliary dyskinesia, chronic bronchitis, chronic obstructive pulmonary disease (COPD), asthma, respiratory tract infections (acute and chronic; viral and bacterial) and lung carcinoma. Diseases mediated by inhibition of channel activating proteases also include diseases other than respiratory diseases that are associated with abnormal fluid regulation across an epithelium, perhaps involving abnormal physiology of the protective surface liquids on their surface, for example xerostomia (dry mouth) or keratoconjunctivitis sire (dry eye). Furthermore, CAP regulation of ENaC in the kidney could be used to promote diuresis and thereby induce a hypotensive effect.

Chronic obstructive pulmonary disease includes chronic bronchitis or dyspnoea associated therewith, emphysema, as well as exacerbation of airways hyper-reactivity consequent to other drug therapy, in particular other inhaled drug therapy. The invention is also applicable to the treatment of bronchitis of whatever type or genesis including, for example, acute, arachidic, catarrhal, croupus, chronic or phthinoid bronchitis.

The compounds of the invention may be used for the treatment of asthma, including but not limited to intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects of, for example, less than 4 or 5 years of age, exhibiting wheezing symptoms and diagnosed or diagnosable as "wheezy infants", an established patient category of major medical concern and now often identified as incipient or early-phase asthmatics, or as "wheezy-infant syndrome".

The suitability of a channel activating protease inhibitor such as a prostasin inhibitor for the treatment of a disease mediated by inhibition of a channel activating protease, may be tested by determining the inhibitory effect of the channel activating protease inhibitor according to the assays described below and following methods known in the art.

In accordance with the foregoing, the present invention further provides a method for preventing or treating any of the diseases or disorders described above in a subject in need of such treatment, which method comprises administering to said subject a therapeutically effective amount of a compound of Formula (1), (2A) or (2B), or a pharmaceutically acceptable salt thereof. For any of the above uses, the required dosage will vary depending on the mode of administration, the particular condition to be treated and the effect desired.

Administration and Pharmaceutical Compositions

In general, compounds of the invention will be administered in therapeutically effective amounts via any of the usual and acceptable modes known in the art, either singly or in combination with one or more therapeutic agents.

Channel activating protease inhibitors of the invention are also useful as co-therapeutic agents for use in combination with other drug substances such as anti-inflammatory, bronchodilatory, antihistamine or anti-tussive drug substances, particularly in the treatment of cystic fibrosis or obstructive or inflammatory airways diseases such as those mentioned hereinbefore, for example as potentiators of therapeutic activity of such drugs or as a means of reducing required dosaging or potential side effects of such drugs.

The channel activating protease inhibitor may be mixed with the other drug substance in a fixed pharmaceutical composition or it may be administered separately, before, simultaneously with or after the other drug substance.

Accordingly, the invention may include a combination of channel activating protease inhibitor with an anti-inflammatory, bronchodilatory, antihistamine, anti-tussive, antibiotic or DNase drug substance, said channel activating protease inhibitor and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate, or steroids described in international patent application WO 02/88167, WO 02/12266, WO 02/100879, WO 02/00679 (for example, Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTD4 antagonists such as montelukast and zafirlukast; PDE4 inhibitors such cilomilast (ARIFLO® GlaxoSmithKline), ROFLUMILAST® (Byk Gulden), V-11294A (Napp), BAY19-8004 (Bayer), SCH-351591 (Schering-Plough), AROFYLLINE® (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; and adenosine $A_{2B}$ receptor antagonists such as those described in WO 02/42298, each of which is incorporated herein in its entirety.

Suitable bronchodilatory drugs include beta-2 adrenoceptor agonists such as albuterol (salbutamol), metaproterenol, terbutaline, salmeterol fenoterol, procaterol, formoterol, or carmoterol and pharmaceutically acceptable salts thereof, and compounds of Formula (1) as described in WO 00/75114 (in free or salt or solvate form), which is incorporated herein by reference in its entirety, such as a compound of formula:

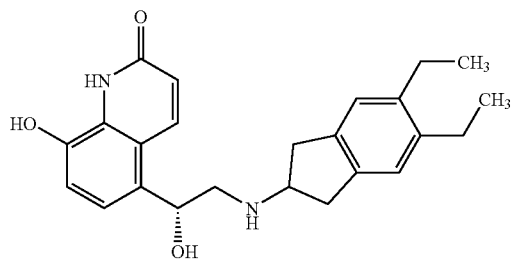

and pharmaceutically acceptable salts thereof; compounds of Formula (1) of WO 04/16601; as well as compounds of EP 1440966, JP 05025045, WO 93/18007, WO 99/64035, US 2002/0055651, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618 WO 04/46083 and WO 04/80964, each in free or salt or solvate form. Each of these publications is incorporated herein in its entirety.

Suitable bronchodilatory drugs also include anticholinergic or antimuscarinic agents, in particular ipratropium bromide, oxitropium bromide, tiotropium salts and CHF 4226 (Chiesi), glycopyrrolate, and also those described in EP 424021, U.S. Pat. No. 3,714,357, U.S. Pat. No. 5,171,744, WO 01/04118, WO 02/00652, WO 02/51841, WO 02/53564, WO 03/00840, WO 03/33495, WO 03/53966, WO 03/87094, WO 04/018422 and WO 04/05285, each of which is incorporated herein in its entirety.

Suitable dual anti-inflammatory and bronchodilatory drugs include dual beta-2 adrenoceptor agonist/muscarinic antagonists such as those disclosed in US 2004/0167167, WO 04/74246 and WO 04/74812, each of which is incorporated herein in its entirety.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine as well as those disclosed in JP 2004107299, WO 03/099807 and WO 04/026841, each of which is incorporated herein in its entirety.

Suitable antibiotics include macrolide antibiotics, for example tobramycin (TOBI™).

Suitable DNase drug substances include dornase alfa (PULMOZYME™), a highly purified solution of recombinant human deoxyribonuclease I (rhDNase), which selectively cleaves DNA. Dornase alfa is used to treat cystic fibrosis.

Other useful combinations of channel activating protease inhibitors with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methyl-phenyl)-5H-benzo-cyclohepten-8-yl]carbonyl]amino]phenyl]-methyl] tetrahydro-N,N-dimethyl-2H-pyran-4-amin-ium chloride (TAK-770), and CCR-5 antagonists described in U.S. Pat. No. 6,166,037, WO 00/66558, WO 00/66559, WO 04/018425 and WO 04/026873, each of which is incorporated herein in its entirety.

In the treatment of a disease mediated by inhibition of prostasin in accordance with the invention, a channel activating protease inhibitor of the invention in free form or in pharmaceutically acceptable salt form, may be administered by any appropriate route, for example orally, e.g. in tablet, capsule or liquid form; parenterally, for example in the form of an injectable solution or suspension; intranasally, for example in the form of an aerosol or other atomisable formulation using an appropriate intranasal delivery device, e.g. a nasal spray such as those known in the art; or by inhalation, such as use with a nebulizer.

The channel activating protease inhibitor may be administered in a pharmaceutical composition together with a pharmaceutically acceptable diluent or carrier. Such compositions may be, for example dry powders, tablets, capsules and liquids, but also injection solutions, infusion solutions or inhalation suspensions, which may be prepared using other formulating ingredients and techniques known in the art.

The dosage of the channel activating protease inhibitor in free form or in pharmaceutically acceptable salt form may depend on various factors, such as the activity and duration of action of the active ingredient, the severity of the condition to be treated, the mode of administration, the species, sex, ethnic origin, age and weight of the subject and/or its individual condition. In a normal case, the daily dose for administration, for example oral administration to a warm-blooded animal, particularly a human being weighing about 75 kg, is estimated to be from approximately 0.7 mg to approximately 1400 mg; or in some examples, from approximately 5 mg to approximately 200 mg. That dose may be administered in a single dose or in several part doses, for example, from 5 to 200 mg.

When the composition comprises an aerosol formulation, it may contain a hydro-fluoro-alkane (HFA) propellant such as HFA134a or HFA227 or a mixture thereof; one or more co-solvents known in the art such as ethanol (up to 20% by weight); one or more surfactants such as oleic acid or sorbitan trioleate; and/or one or more bulking agents such as lactose. When the composition comprises a dry powder formulation, it may contain, for example, the channel activating protease inhibitor having a particle diameter up to 10 microns, optionally together with a diluent or carrier, such as lactose, of the desired particle size distribution and a compound that helps to protect against product performance deterioration due to moisture (e.g. magnesium stearate). When the composition comprises a nebulised formulation, it may contain, for example, the channel activating protease inhibitor either dissolved, or suspended, in a vehicle containing water, a co-solvent such as ethanol or propylene glycol and a stabiliser, which may be a surfactant.

The invention includes (A) a compound of the invention in inhalable form, e.g. in an aerosol or other atomisable composition or in an inhalable particulate, e.g. micronised form; (B) an inhalable medicament comprising a compound of the invention in inhalable form; (C) a pharmaceutical product comprising a compound of the invention in inhalable form in association with an inhalation device; and (D) an inhalation device containing a compound of the invention in inhalable form.

Processes for Making Compounds of the Invention

The present invention also includes processes for the preparation of compounds of the invention. In the reactions described, reactive functional groups, where desired in the final product (e.g., hydroxy, amino, imino, thio or carboxy groups), may be protected using protecting groups known in the art, to avoid their unwanted participation in the reactions. Conventional protecting groups may be used in accordance with standard practice, for example, see T. W. Greene and P. G. M. Wuts in "Protective Groups in Organic Chemistry", John Wiley and Sons, 1991.

The compounds of the invention may be prepared following the Reaction scheme I below:

The intermediate compound II may be synthesized by reacting intermediate compound Iaa with an alkyl reagent of

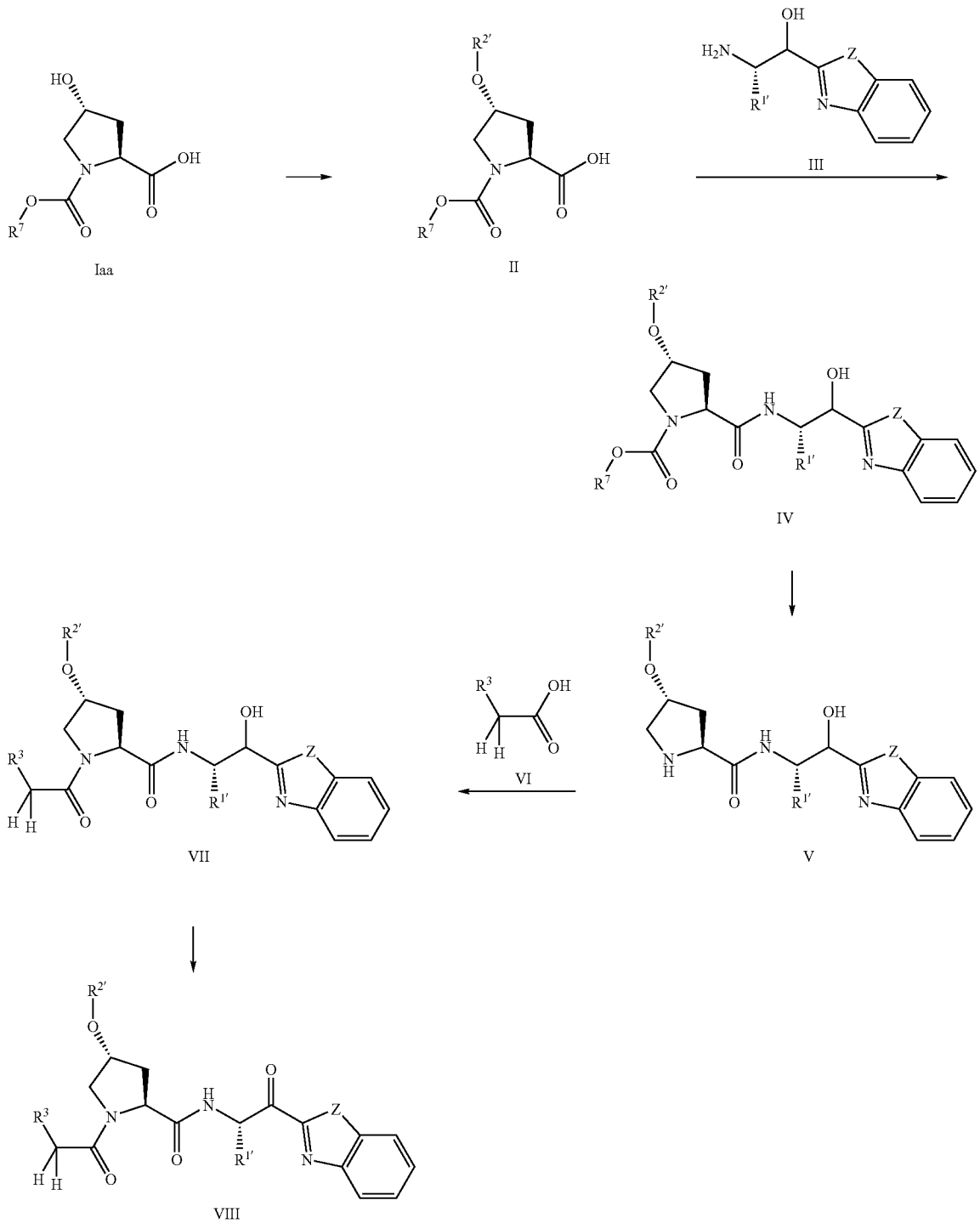

Scheme 1 wherein R$^{1'}$ is (CR$_2$)$_n$—X$_i$—R$^1$;
R$^{2'}$ is (CR$_2$)$_k$R$^2$;
R$^1$, R$^2$, R$^3$, X, Z, i, k and n are as defined in Formula (1);
R$^7$ is an alkyl carbamate protecting group (for example, methyl, ethyl, t-butyl or benzyl and the like).

the type R$^{2'}$—Y where Y is a leaving group, in the presence of a suitable base and a suitable organic solvent. Examples of leaving groups in alkyl reagents R$^{2'}$—Y include but are not limited to halides such as chlorides and bromides, or a tosylate, mesylate, or besylate leaving groups, and the like. These reactions may proceed in a temperature range of about 0° C. to about 60° C. and may take up to about 24 hours to complete.

The intermediate compound IV may be synthesized by reacting intermediate compound II with reagent III with a suitable peptide coupling reagent and a suitable base in the presence of a suitable solvent. Suitable bases for this reaction include but are not limited to triethylamine, DIEA, pyridine, 2,4,6-collidine, and other suitable bases within the knowledge of those skilled in the art. The reaction may proceed in a temperature range of about 0° C. to about 40° C. and may take up to about 24 hours to complete.

In the above Reaction Scheme I, intermediate compound V may be synthesized by removing the carbamate protecting group (e.g., where $R^7$ is t-butyl) from intermediate compound IV with a suitable acid, and optionally in the presence of a suitable organic solvent. Suitable acids include but are not limited to TFA, p-TsOH, TfOH, HCl, HBr, HF, $HBF_4$, and other suitable acids within the knowledge of those skilled in the art. The reaction may proceed in a temperature range of about −20° C. to about 40° C. and may take up to about 24 hours to complete.

Alternatively, intermediate compound V may be synthesized by removing the carbamate protecting group from intermediate compound IV (e.g., where $R^7$ is benzyl or any benzylic derivative) with hydrogen gas in the presence of a suitable catalyst and a suitable solvent or water. Examples of suitable catalysts include but are not limited to Pd/C, Pt, $PtO_2$, Pt/C, Rh/C, and other suitable catalysts within the knowledge of those skilled in the art. The reaction may proceed in a temperature range of about 0° C. to about 80° C., with hydrogen pressures of about 15 psi to about 80 psi, and may take up to about 48 hours to complete.

Alternatively, a compound of Formula V may be synthesized by removing the carbamate protecting group from a compound of Formula IV (e.g., where $R^7$ is allyl or any allylic derivative), by reacting a compound of Formula IV with a suitable allylic scavenger (for example $Et_2NH$, morpholine, piperidine, pyrrolidine, $NaBH_4$, and the like) in the presence of a suitable catalyst (for example $Pd_2(dba)_3$, $PdCl_2$, $Pd(PPh_3)_4$ and the like) in the presence of a suitable solvent (for example water, methanol, ethanol, isopropanol, t-butanol, n-propanol, n-butanol, cyclohexanol, and mixtures thereof and the like).

The intermediate compound VII may be synthesized by reacting intermediate compound V with reagent VI in the presence of a suitable peptide coupling reagent and a suitable base ($Et_3N$, DIEA, pyridine, 2,4,6-collidine, and the like) in the presence of a suitable solvent. The reaction may proceed in a temperature range of about 0° C. to about 40° C., and may take up to about 24 hours to complete.

The final compound VIII may be synthesized by reacting a compound of Formula VII with a suitable oxidant in the presence of a suitable organic solvent or water. Suitable oxidants include but are not limited to Dess-Martin periodinane, 2-iodobenzoic acid with oxone, TEMPO with trichlorisocyanuric acid, TEMPO with NaOCl, DMSO with oxalyl chloride, pyridinium chlorochromate, $MnO_2$, $CrO_2$, and other suitable oxidants within the knowledge of those skilled in the art. The reaction may proceed in a temperature range of about 0° C. to about 40° C., and may take up to about 24 hours to complete.

Suitable peptide coupling reagents for use in the reactions described in Reaction scheme I include but are not limited to DCC, DIC, HATU, BOP, PyBOP, EDC and other coupling reagents within the knowledge of those skilled in the art.

Suitable bases for use in the reactions described in Reaction scheme I include but are not limited to hydroxides such as NaOH, KOH, or LiOH; carbonates such as $K_2CO_3$ or $CsCO_3$; hydrides such as NaH or KH, and the like. Other suitable bases are amines, DIEA, pyridine, 2,4,6-collidine, and other suitable bases within the knowledge of those skilled in the art.

Suitable organic solvents for use in the reactions described in Reaction scheme I include but are not limited to DMSO, THF, DMF, DMAc, acetonitrile, acetone, 2-propanone, butanone, HMPA, NMP, dichloromethane, chloroform, 1,2-dichloroethane, diethyl ether, methanol, ethanol, t-butanol, isopropanol, propanol, n-butanol, cyclohexanol, acetonitrile, dioxane, MTBE, benzene, toluene, and mixtures thereof, and other suitable solvents within the knowledge of those skilled in the art.

Additional Processes for Making Compounds of the Invention

A compound of the invention may be prepared as a pharmaceutically acceptable acid addition salt by reacting the free base form of the compound with a pharmaceutically acceptable inorganic or organic acid. Alternatively, a pharmaceutically acceptable base addition salt of a compound of the invention may be prepared by reacting the free acid form of the compound with a pharmaceutically acceptable inorganic or organic base.

Alternatively, the salt forms of the compounds of the invention may be prepared using salts of the starting materials or intermediates.

The free acid or free base forms of the compounds of the invention may be prepared from the corresponding base addition salt or acid addition salt from, respectively. For example, a compound of the invention in an acid addition salt form may be converted to the corresponding free base by treating with a suitable base (e.g., ammonium hydroxide solution, sodium hydroxide, and the like). A compound of the invention in a base addition salt form may be converted to the corresponding free acid by treating with a suitable acid (e.g., hydrochloric acid, etc.).

Compounds of the invention in unoxidized form may be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention may be prepared by methods known to those of ordinary skill in the art (e.g., for further details, see Saulnier et al., (1994), Bioorganic and Medicinal Chemistry Letters, Vol. 4, p. 1985). For example, appropriate prodrugs may be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention may be made by means known to those of ordinary skill in the art. A detailed description of techniques applicable to the creation of protecting groups and their removal may be found in T. W. Greene, "Protecting Groups in Organic Chemistry", $3^{rd}$ edition, John Wiley and Sons, Inc., 1999.

Compounds of the present invention may be conveniently prepared, or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

Compounds of the invention may be prepared as their individual stereoisomers by reacting a racemic mixture of the compound with an optically active resolving agent to form a pair of diastereoisomeric compounds, separating the diastereomers and recovering the optically pure enantiomers. Resolution of enantiomers may be carried out using covalent diastereomeric derivatives of the compounds of the invention, or by using dissociable complexes (e.g., crystalline diastereomeric salts). Diastereomers have distinct physical properties (e.g., melting points, boiling points, solubilities, reactivity, etc.), and may be readily separated by taking advantage of these dissimilarities. The diastereomers may be separated by chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture may be found in Jean Jacques, Andre Collet, Samuel H. Wilen, "Enantiomers, Racemates and Resolutions", John Wiley And Sons, Inc., 1981.

In summary, the compounds of Formula (1) may be made by a process, which involves:

(a) that of Reaction Scheme I;

(b) optionally converting a compound of the invention into a pharmaceutically acceptable salt;

(c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

Insofar as the production of the starting materials is not particularly described, the compounds are known or may be prepared analogously to methods known in the art or as disclosed in the Examples hereinafter. One of skill in the art will appreciate that the above transformations are only representative of methods for preparation of the compounds of the present invention, and that other well known methods may similarly be used. The present invention is further exemplified, but not limited, by the following intermediates (Reference compounds) and Examples that illustrate the preparation of the compounds of the invention.

In the synthethic methodologies below, the following common abbreviations known in the art are used: DCM (dichloromethane); THF (tetrahydrofuran); and DIEA (diisopropylethylamine).

Reference compound 1

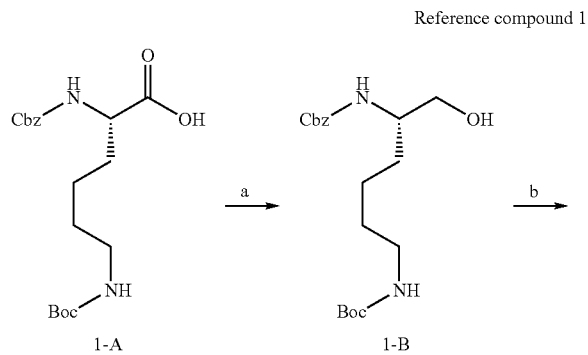

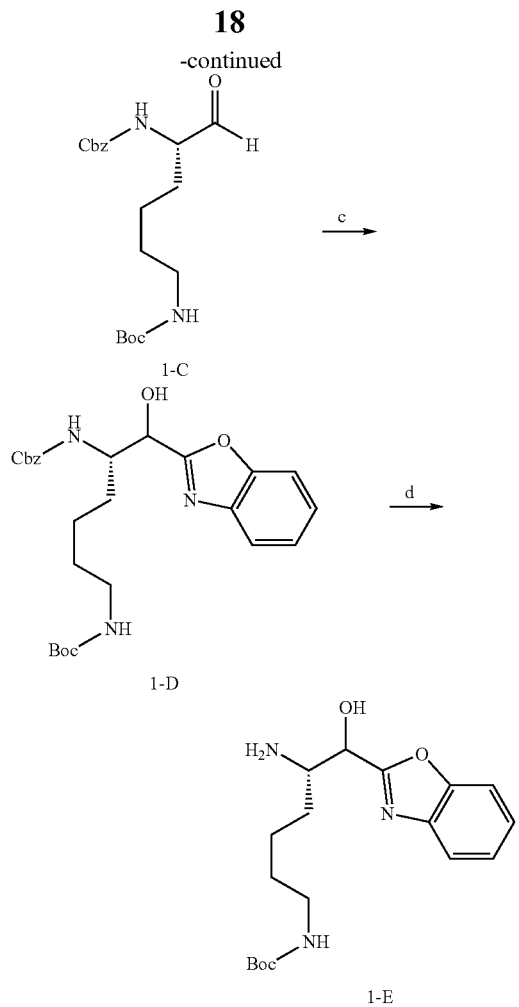

In the above reaction scheme, the reagents and conditions are: (a) iso-BuOCOCl, Et$_3$N, THF; NaBH$_4$, H$_2$O. (b) Dess-Martin periodinane, CH$_2$Cl$_2$; (c) iso-PrMgCl, benzoxazole, THF, −20° C., 30 min, then 1-C, −20° C. to rt. (d) H$_2$ (40 psi), EtOH, Pd/C 10%, rt, 18 h.

1-B: The crude starting material, Z-Lys(Boc)OH 1-A (320 g, 842 mmol) is dissolved in THF (2.5 L), and the solution is cooled to −10° C. followed by the addition of triethylamine (115.2 mL, 1.0 eq) and dropwise addition of iso-butylchloroformate (118.7 mL, 1.1 eq). The resulting suspension is stirred for 2 h at 0° C. The reaction mixture is filtered and cooled to −10° C. NaBH$_4$ (64.6 g, 2.1 eq) is dissolved in water (500 mL) at 0° C., and the solution is added portionwise to the THF solution (heavy CO$_2$ evolution). The reaction mixture is allowed to warm to room temperature and stirred for one hour. The reaction mixture is acidified with 1N HCl solution, and the aqueous phase is extracted several times with EtOAc. The combined organic layers are washed with water, saturated aqueous NaHCO$_3$ solution, and brine; dried on MgSO$_4$, and the solvent is removed in vacuo. The product is purified by flash column chromatography (hexanes/ethyl acetate) to afford the desired product as a white foam.

1-C: The alcohol 1-B (200 g, 545.8 mmol) is dissolved in DCM (2.0 L) and cooled to 0° C. A solution of the Dess-Martin reagent (231 g, 1.0 eq) in DCM (2.0 L) is added portionwise. The suspension is allowed to warm to room temperature and stirred until complete conversion (1-4 h). A 1:1 mixture of saturated aqueous NaHCO$_3$ solution and a 1M Na$_2$S$_2$O$_3$ solution is added, and the resulting biphasic system is stirred vigorously for 20 min. The organic layer is separated and the aqueous layer is extracted once with DCM. The combined organic layers are distilled in vacuo, and the resulting oil is taken up in EtOAc and washed six times with the NaHCO$_3$/Na$_2$S$_2$O$_3$ mixture, water, and brine; dried on MgSO$_4$, and the solvent is removed in vacuo to give the crude aldehyde as a yellowish oil. The material is directly used in the next step without further purification.

1-D: To a solution of isopropyl-magnesium chloride (1.67 eq. vs aldehyde, 390 ml of a 2M-THF solution from Sigma-Aldrich) in THF (1.5 L) is added benzoxazole (92.8 g, 1.67 eq) in THF (1.0 L) at −20° C. The reaction mixture is stirred at −20° C. for 30 min (color change to deep red), and a solution of the aldehyde 1-C (170 g, 466 mmol) in THF (1.5 L) is slowly added under controlled temperature at −20° C. to −15° C. The reaction mixture is allowed to warm to room temperature and stirred until completion. The reaction mixture is quenched with saturated aqueous NH$_4$Cl solution and the solvent is removed in vacuo. The aqueous phase is extracted three times with EtOAc, and the combined organic layers are excessively washed with 1N HCl solution, water, and brine; dried on MgSO$_4$, and the solvent is removed in vacuo to give the crude benzoxazole as a deep red oil. Purification on silica with EtOAc/hexanes (1:5 to 1:1) gave the benzoxazole as a yellow solid.

1-E: A solution of intermediate 1-D (25.0 g, 51.7 mmol) is dissolved in ethanol (150 mL). Pd/C (10%, wet, Degussa type) is added, and the flask is placed on a Parr shaker overnight and subjected to hydrogen gas at 40 psi. The catalyst is filtered through Celite, and solvent is removed in vacuo. The crude material is purified by flash chromatography using first a gradient of hexanes/EtOAc to remove less polar and colored impurities, then followed by a gradient of DCM/MeOH to elute the desired compound. The solvent is removed in vacuo, and the compound is triturated several times in ether to afford the desired reference compound 1 as a white powder. $^1$H-NMR (DMSO-d6, 400 MHz) δ 7.73-7.70 (2H, m), 7.40-7.34 (2H, m), 6.78-6.73 (1H, m), 4.55-4.51 (1H, m), 3.05-3.01 (1H, m), 2.92-2.83 (2H, m), 1.48-1.18 (14H, m). LCMS: 350.5 (M+H)$^+$.

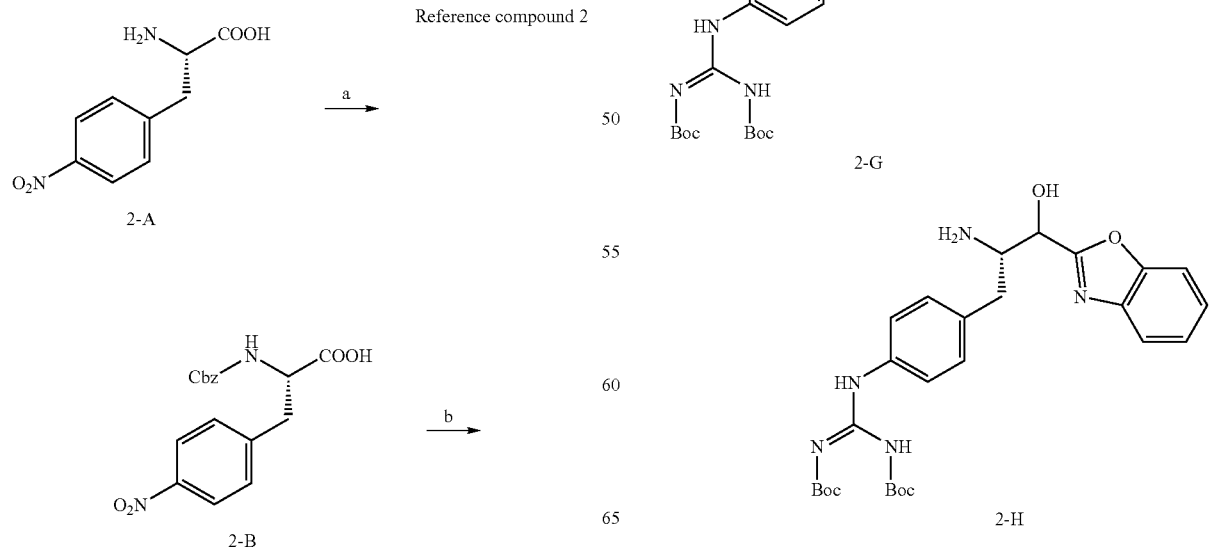

In the above Scheme 2, the reagents and conditions are: a) Cbz-OSu, Et$_3$N, THF, H$_2$O, rt, 18 h, (b) i. iso-BuOCOCl, Et$_3$N, THF; ii. NaBH$_4$, H$_2$O; (c) Dess-Martin periodinane, CH$_2$Cl$_2$; (d) iso-PrMgCl, benzoxazole, THF, −20° C., 30 min, then 2-D, −20° C. to rt; (e) Indium, NH$_4$Cl, EtOH, reflux, 5 h; (f) N,N-Bis (tert-butoxycarbonyl)-1H-pyrazole-1-carboxamidine, DIEA, MeOH; (g) H$_2$, (40 psi), 10% Pd/C, EtOH.

2-B: L-Nitrophenylalanine hydrochloride (4.45 g, 18.0 mmol) and N-(Benzyloxycarbonyloxy)succinimide (Cbz-OSu) (4.49 g, 18.0 mmol) are added to a round bottomed flask containing THF (60 mL) and water (20 mL). The mixture is stirred at room temperature and Et$_3$N (10.1 mL, 72.0 mmol) is added, and the reaction is stirred overnight at room temperature. The clear solution is diluted with EtOAc (200 mL) and washed with 1N HCl (3×100 mL) and brine (1×100 mL), and dried with MgSO$_4$. Solvent is evaporated in vacuo to give 2-B as a white solid, which is used without further purification.

2-C to 2-E: These intermediates are prepared following methods analogous to those described for preparing intermediates 1-B to 1-D of Reference compound 1, respectively.

2-F: The nitrophenyl analog 2-E (1.85 g, 4.15 mmol) is dissolved in EtOH (50 mL) and heated to reflux. Saturated aqueous NH$_4$Cl (5 mL) is added, followed by powdered indium (3.2 g, 27.9 mmol). The reaction mixture is stirred at reflux temperature for 5 h, cooled to room temperature, and the solvent is removed in vacuo. The crude material is suspended in EtOAc (100 mL) and washed with saturated NaHCO$_3$ (3×100 mL), dried with MgSO$_4$, and filtered through Celite. The solvent is removed in vacuo to give the aniline 2-F as an off-white waxy solid, which is used without further purification.

2-G: Aniline 2-F (1.52 g, 3.67 mmol) is dissolved in MeOH (10 mL), and DIEA (0.7 mL, 4.4 mmol) and N,N-Bis (tert-butoxycarbonyl)-1H-pyrazole-1-carboxamidine (1.37 g, 4.4 mmol) are added, and the reaction mixture is stirred at room temperature. After 4 h, another 0.5 equiv of N,N-Bis (tert-butoxycarbonyl)-1H-pyrazole-1-carboxamidine (0.685 g, 2.2 mmol) is added, and the reaction is then stirred overnight at room temperature. EtOAc (100 mL) is added, and the organic layer is washed with water, and brine; and dried on MgSO$_4$. The solvent is removed in vacuo and the crude material is purified by silica gel chromatography with EtOAc/hexanes (0 to 100% gradient) to afford the desired product 2-G as an oil.

2-H: This compound is prepared from 2-G using methods analogous to those described for the preparation of intermediate 1-E for Reference compound 1.

Scheme 3

Reference compound 2

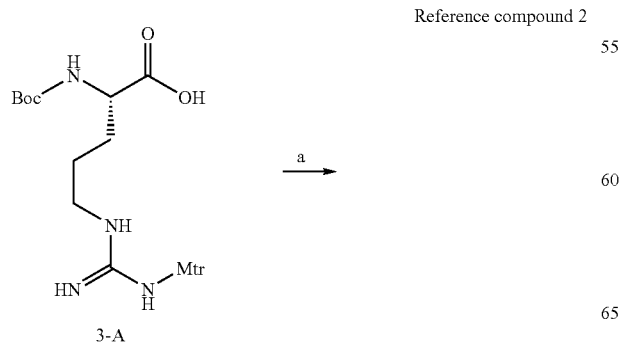

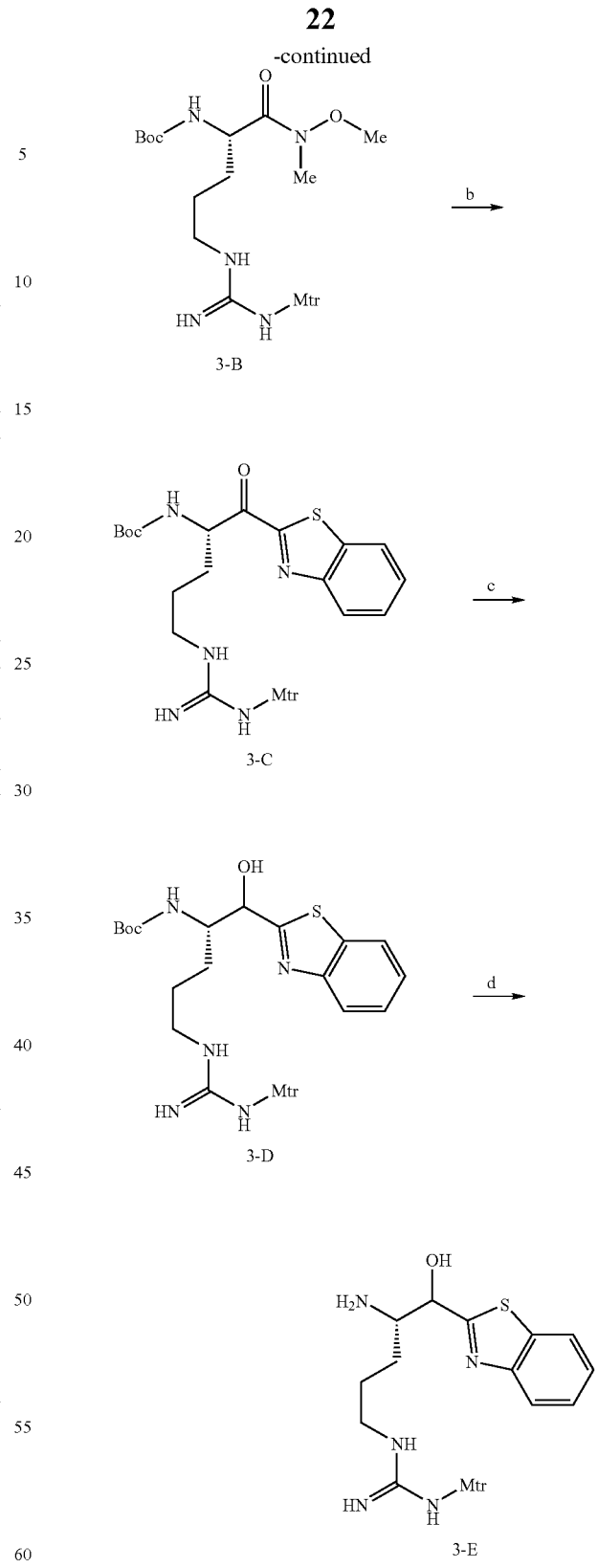

In the above Scheme 3, the reagents and conditions are: (a) HN(OMe)Me.HCl, BOP, Et3N, DMF, 0° C. to rt; (b) n-BuLi (2.5M in hexanes), benzothiazole, THF, −78° C., then 3-B, THF, −70° C. to rt; (c) NaBH$_4$, MeOH; (d) p-TsOH, CH$_2$Cl$_2$, 6 h.

3-B: BOP (50 g, 112 mmol) is added in one portion to a stirring solution of 3-A (49.92 g, 102.6 mmol), N,O-dimethylhydroxylamine hydrochloride (30.4 g, 224 mmol), and triethylamine (88 mL, 616 mmol) in dry DMF (200 mL) under argon at 0° C. The reaction mixture is allowed to slowly warm to room temperature over 2 h, filtered through diatomaceous earth, and concentrated in vacuo. The residue is dissolved in ethyl acetate, washed with H$_2$O, 1M aqueous KHSO$_4$, saturated aqueous NaHCO$_3$, and brine; dried and concentrated in vacuo. The residue is purified by column to give compound 3-B.

3-C: n-Butyllithium (2.5 M in hexanes, 272.2 mL, 681.4 mmol) is added dropwise at −78° C. under argon to a stirring solution of benzothiazole (115.72 g, 850.7 mmol) in dry THF (1660 mL) at a rate that kept the reaction temperature below −64° C. Upon completion of addition, the reaction mixture is stirred for 30 min at −70° C., and a solution of compound 3-B (45 g, 85.7 mmol) in dry THF (300 mL) is added at a rate that maintained the reaction temperature below −70° C. The reaction is stirred for 15 min, quenched with saturated aqueous NH$_4$Cl, and stirred for 16 h at room temperature. The resulting organic layer is separated, diluted with ethyl acetate, washed with water and brine; dried and concentrated in vacuo, and purified by silica gel chromatography to give compound 3-C.

3-D: To a solution of 3-C (33.7 g, 55.82 mmol) in MeOH (407 mL) at 0° C. is added NaBH$_4$ (9.98 g). The reaction mixture is slowly warmed to room temperature over 1 h, then heated to 45° C. for 1 h, and then cooled back to room temperature. The reaction is quenched with acetone (60 mL), and concentrated in vacuo. The residue is dissolved in ethyl acetate, washed with brine, and dried over MgSO$_4$. The crude material is purified by silica gel chromatography to afford product 3-D.

3-E: p-TsOH is added to a stirring solution of compound 3-D (28.2 g) in CH$_2$Cl$_2$ (300 ml) at room temperature until the solution is saturated. The reaction is stirred at room temperature for 6 h. Water is added, and the organic layer is extracted with EtOAc, washed with 1:1 mixture (V/V) of brine and 10% aqueous Na$_2$CO$_3$, dried over Na$_2$SO$_4$, and purified by silica gel chromatography to give the product 3-E.

Scheme 4

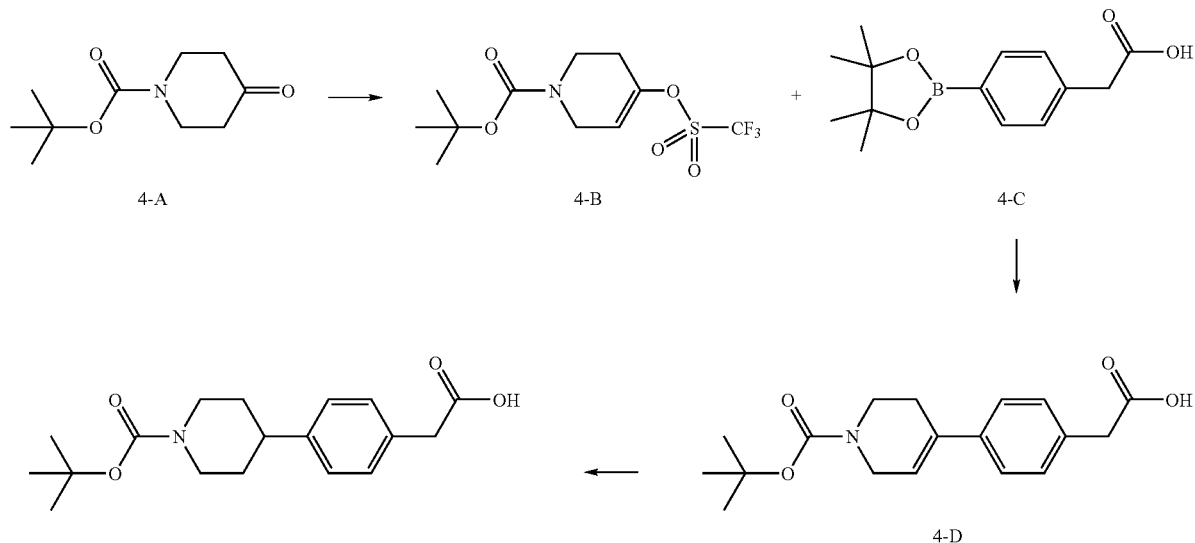

To prepare intermediate 4-B, n-Butyllithium (1.6 M in hexanes, 11.3 mL, 17.9 mmol) is added dropwise to a solution of i-Pr$_2$NH (2.53 mL, 17.9 mmol) in THF (25 mL) cooled to −78° C. and stirred for 10 min. Ketone 4-A (3.25 g, 16.3 mmol) is added dropwise and the solution continued to stir at −78° C. for another 25 min. N-phenyl-bis-(trifluoromethanesulfonamide) (6.26 g, 17.5 mmol) dissolved in THF (25 mL) is added dropwise, and the reaction mixture is placed in a water/ice-bath at 0° C. and stirred for 4 h. The solvent is evaporated, and the crude residue taken up in a minimum amount of hexanes and then filtered through a plug of alumina using hexanes:EtOAc/9:1 as the eluent. The solvent is removed in vacuo to afford the desired triflate 4-B.

Intermediates 4-B (715 mg, 2.16 mmol) and 4-C (514 mg, 1.96 mmol) are dissolved in dioxane (10 mL) in a microwave reaction vial. K$_3$PO$_4$ (874 mg, 4.12 mmol) in water (2.5 mL) is added, and the solution is degassed by three liquid nitrogen freeze-pump-thaw cycles. The catalyst PdCl$_2$(dppf) (143 mg, 0.196 mmol) is added, and the vial purged with nitrogen and sealed. The reaction is heated in an Emrys Personal Chemistry microwave reactor to 150° C. for 25 min. The dioxane is evaporated in vacuo, and the residue taken up in and partitioned between EtOAc (50 mL) and 10% aqueous citric acid (50 mL). The layers are separated, and the organic phase is washed with 10% aqueous citric acid (2×50 mL) and brine (50 mL). The organic layer is dried with Na$_2$SO$_4$ and evaporated, and the crude residue purified by silica gel chromatography (hexanes/EtOAc gradient) to afford the intermediate 4-D.

Intermediate 4-D (45 mg, 0.142 mmol) is dissolved in EtOH (10 mL) in a 25 mL flask fitted with a rubber septum. A catalytic amount of Pd/C (10%) is added, and hydrogen gas is introduced from a balloon fitted with a needle inserted through the septum. The reaction is stirred at room temperature until the starting material is consumed (as indicated by LCMS). The catalyst is then filtered, and the solvent evaporated to dryness to afford Reference compound 4.

Scheme 5

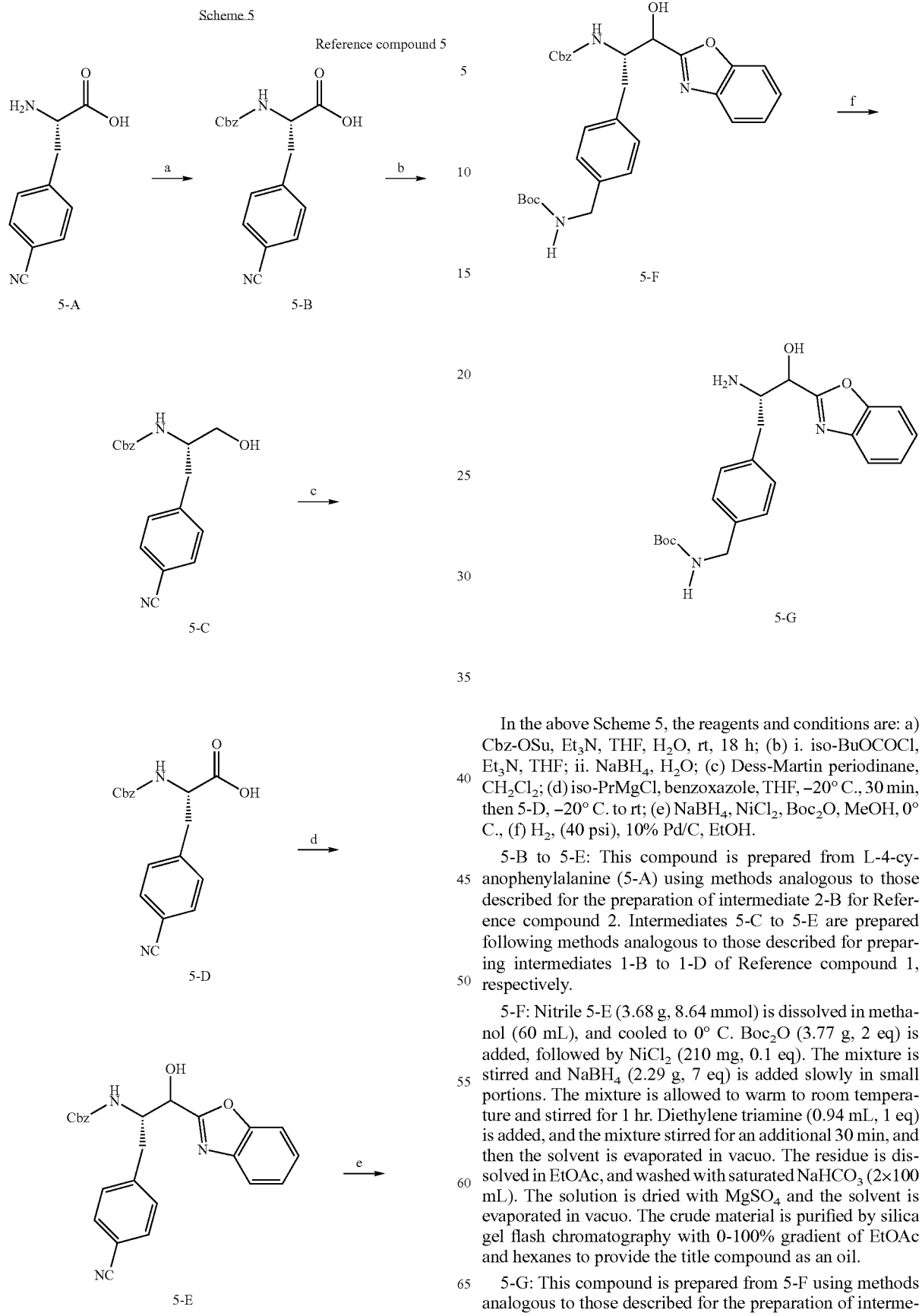

In the above Scheme 5, the reagents and conditions are: a) Cbz-OSu, Et$_3$N, THF, H$_2$O, rt, 18 h; (b) i. iso-BuOCOCl, Et$_3$N, THF; ii. NaBH$_4$, H$_2$O; (c) Dess-Martin periodinane, CH$_2$Cl$_2$; (d) iso-PrMgCl, benzoxazole, THF, −20° C., 30 min, then 5-D, −20° C. to rt; (e) NaBH$_4$, NiCl$_2$, Boc$_2$O, MeOH, 0° C., (f) H$_2$, (40 psi), 10% Pd/C, EtOH.

5-B to 5-E: This compound is prepared from L-4-cyanophenylalanine (5-A) using methods analogous to those described for the preparation of intermediate 2-B for Reference compound 2. Intermediates 5-C to 5-E are prepared following methods analogous to those described for preparing intermediates 1-B to 1-D of Reference compound 1, respectively.

5-F: Nitrile 5-E (3.68 g, 8.64 mmol) is dissolved in methanol (60 mL), and cooled to 0° C. Boc$_2$O (3.77 g, 2 eq) is added, followed by NiCl$_2$ (210 mg, 0.1 eq). The mixture is stirred and NaBH$_4$ (2.29 g, 7 eq) is added slowly in small portions. The mixture is allowed to warm to room temperature and stirred for 1 hr. Diethylene triamine (0.94 mL, 1 eq) is added, and the mixture stirred for an additional 30 min, and then the solvent is evaporated in vacuo. The residue is dissolved in EtOAc, and washed with saturated NaHCO$_3$ (2×100 mL). The solution is dried with MgSO$_4$ and the solvent is evaporated in vacuo. The crude material is purified by silica gel flash chromatography with 0-100% gradient of EtOAc and hexanes to provide the title compound as an oil.

5-G: This compound is prepared from 5-F using methods analogous to those described for the preparation of intermediate 1-E for Reference compound 1.

Scheme 6

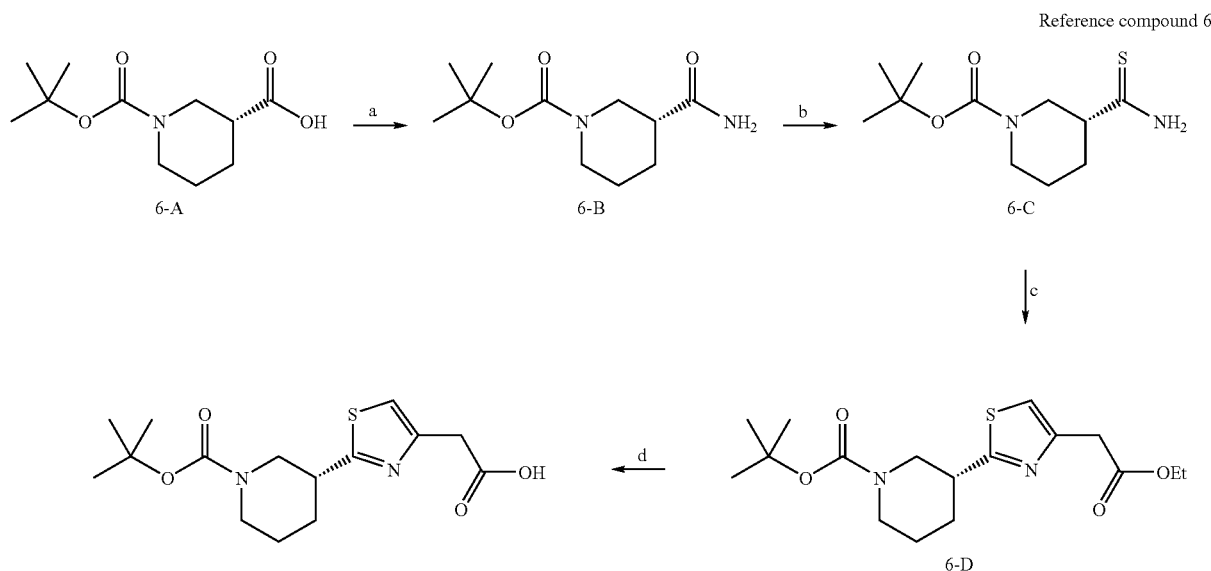

6-B: (R)-Boc-nipecotic acid (2.50 g, 10.9 mmol) and HOBt (1.77 g, 13.1 mmol) are dissolved in DMF (50 mL), and EDC (2.30 g, 12.0 mmol) is added. The reaction mixture is stirred for 1 h, and 30% aqueous ammonia (2.8 mL) is added, and the reaction is stirred for another 2 h. The reaction is then diluted with EtOAc (200 mL) and partitioned with water (100 mL). The organic layer is washed with saturated aq. NaHCO₃ (3×200 mL), and then dried with MgSO₄. The solvent is removed in vacuo to afford amide 6-B as a waxy solid.

6-C: Amide 6-B (2.40, 10.5 mmol) is dissolved in THF (50 mL). Lawesson's reagent (2.64 g, 6.54 mmol) is added, and the reaction mixture stirred at room temperature for 4 h. The solvent is evaporated, and the crude material is purified by silica gel chromatography using a gradient of 0-5% MeOH in CH₂Cl₂ as eluent. The solvent is evaporated to afford the desired thioamide.

6-D: Thioamide 6-C (1.27 g, 5.20 mmol) is dissolved in CH₂Cl₂ (50 mL). Ethyl-4-chloroacetoacetate (0.8 mL, 5.72 mmol) is added, and the solution is stirred at room temperature for 5 h. The solvent is removed in vacuo, and the crude residue is then dissolved in EtOH (50 mL). Activated powdered molecular sieves (1.2 g) are added and the reaction mixture is heated at reflux for 18 h. The mixture is then cooled to room temperature and filtered through Celite. Saturated aq. NaHCO₃ (50 mL) is added to the filtered solution, and then extracted with EtOAc (3×50 mL). The combined organic layer is washed with brine (100 mL) and dried (MgSO₄). The solvent is evaporated in vacuo and the crude material is purified by silica gel flash chromatography using a 0-100% gradient of EtOAc and hexanes to provide thiazole 6-D.

Reference compound 6: LiOH.H₂O (65 mg, 1.55 mmol) is dissolved in water (5 mL) and added dropwise to a stirring solution of ethyl ester 6-D dissolved in dioxane (20 mL). The reaction is stirred for 2 h, and dioxane is evaporated. The crude residue is partitioned between EtOAc and 1M NaHSO₄; the combined organic layer is dried (MgSO₄) and evaporated in vacuo; and the crude material is purified by reverse phase HPLC (H₂O/MeCN mobile phase).

Scheme 7

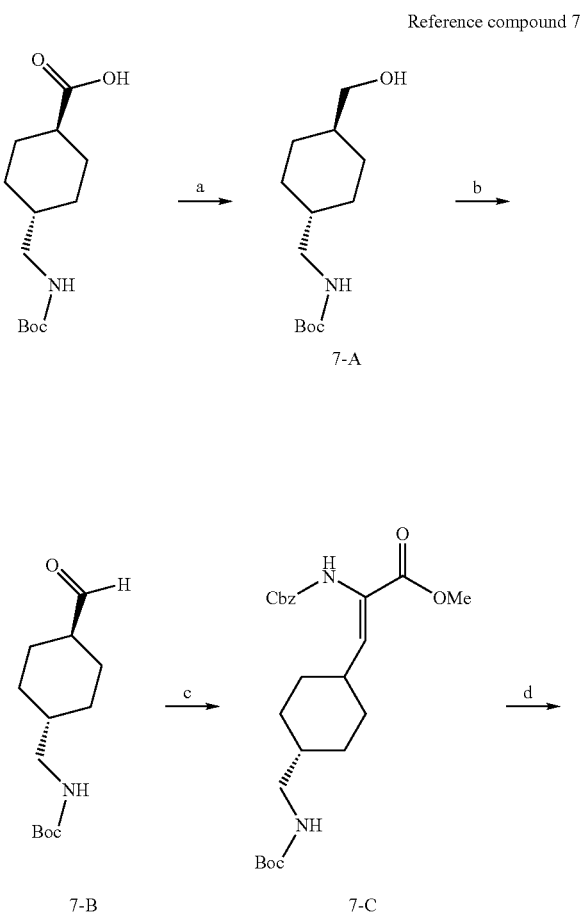

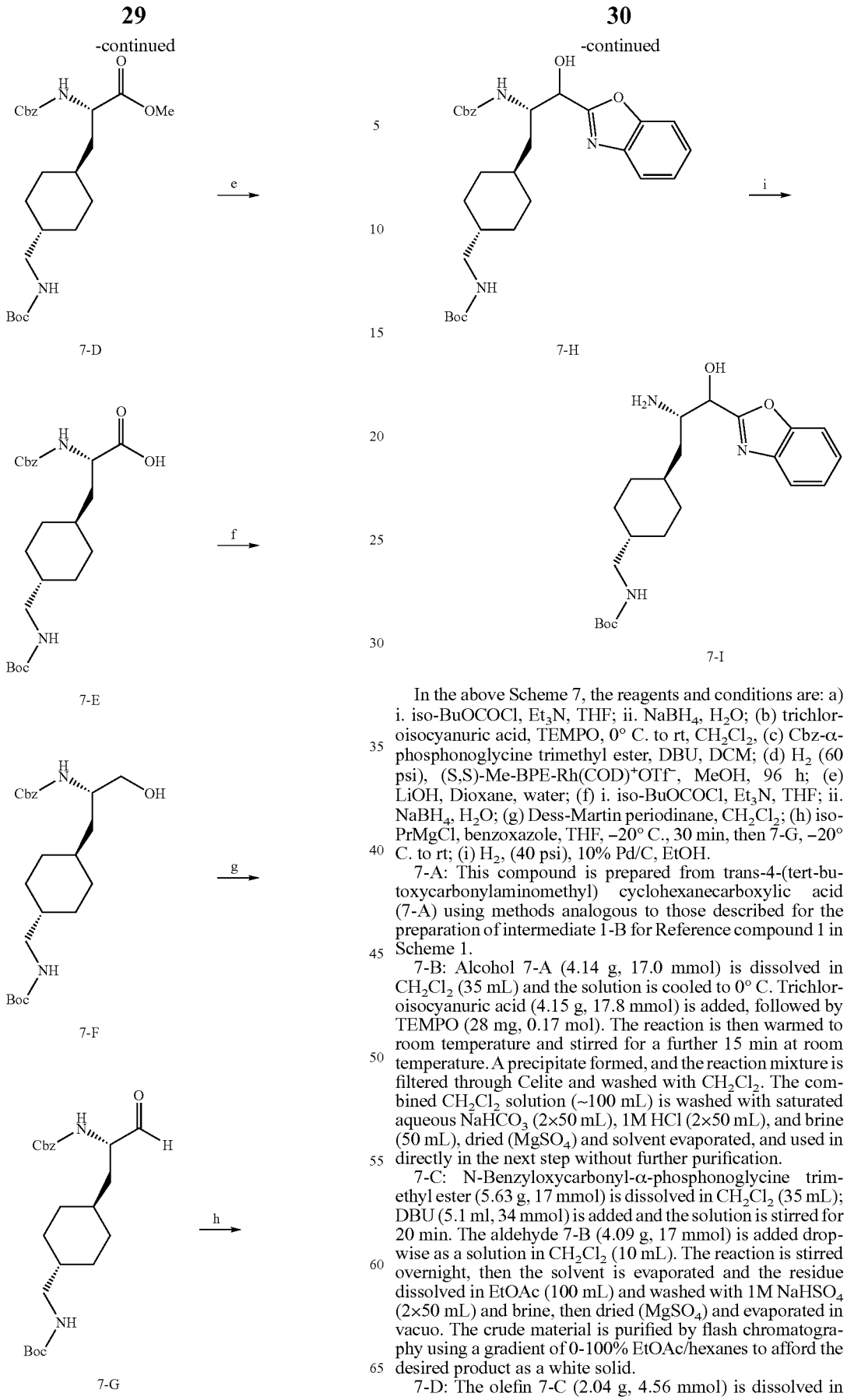

In the above Scheme 7, the reagents and conditions are: a) i. iso-BuOCOCl, Et₃N, THF; ii. NaBH₄, H₂O; (b) trichloroisocyanuric acid, TEMPO, 0° C. to rt, CH₂Cl₂, (c) Cbz-α-phosphonoglycine trimethyl ester, DBU, DCM; (d) H₂ (60 psi), (S,S)-Me-BPE-Rh(COD)⁺OTf⁻, MeOH, 96 h; (e) LiOH, Dioxane, water; (f) i. iso-BuOCOCl, Et₃N, THF; ii. NaBH₄, H₂O; (g) Dess-Martin periodinane, CH₂Cl₂; (h) iso-PrMgCl, benzoxazole, THF, −20° C., 30 min, then 7-G, −20° C. to rt; (i) H₂, (40 psi), 10% Pd/C, EtOH.

7-A: This compound is prepared from trans-4-(tert-butoxycarbonylaminomethyl) cyclohexanecarboxylic acid (7-A) using methods analogous to those described for the preparation of intermediate 1-B for Reference compound 1 in Scheme 1.

7-B: Alcohol 7-A (4.14 g, 17.0 mmol) is dissolved in CH₂Cl₂ (35 mL) and the solution is cooled to 0° C. Trichloroisocyanuric acid (4.15 g, 17.8 mmol) is added, followed by TEMPO (28 mg, 0.17 mol). The reaction is then warmed to room temperature and stirred for a further 15 min at room temperature. A precipitate formed, and the reaction mixture is filtered through Celite and washed with CH₂Cl₂. The combined CH₂Cl₂ solution (~100 mL) is washed with saturated aqueous NaHCO₃ (2×50 mL), 1M HCl (2×50 mL), and brine (50 mL), dried (MgSO₄) and solvent evaporated, and used in directly in the next step without further purification.

7-C: N-Benzyloxycarbonyl-α-phosphonoglycine trimethyl ester (5.63 g, 17 mmol) is dissolved in CH₂Cl₂ (35 mL); DBU (5.1 ml, 34 mmol) is added and the solution is stirred for 20 min. The aldehyde 7-B (4.09 g, 17 mmol) is added dropwise as a solution in CH₂Cl₂ (10 mL). The reaction is stirred overnight, then the solvent is evaporated and the residue dissolved in EtOAc (100 mL) and washed with 1M NaHSO₄ (2×50 mL) and brine, then dried (MgSO₄) and evaporated in vacuo. The crude material is purified by flash chromatography using a gradient of 0-100% EtOAc/hexanes to afford the desired product as a white solid.

7-D: The olefin 7-C (2.04 g, 4.56 mmol) is dissolved in MeOH (100 mL), and the solution is degassed prior to addition of the catalyst, (−)-1,2-Bis-((2S,3S)-2,5-dimethylphospholano)ethane(cyclooctadiene)-rhodium(I)-trifluoro-methane sulfonate (28 mg, 1 mol %). The reaction mixture is placed in a Parr shaker and shaken under 60 psi of $H_2$ for 4 days. The solvent is then evaporated in vacuo, and the crude material is purified by flash chromatography using a gradient of 0-100% EtOAc/hexanes to afford the desired product as a white solid.

7-E: The methyl ester 7-D (1.81 g, 4.04 mmol) is dissolved in dioxane (50 mL) and stirred at 0° C. LiOH (203 mg, 4.84 mmol) dissolved in water (10 mL) is added dropwise, and the solution is then warmed to room temperature. After the starting material had disappeared (by LCMS), the solvent is evaporated, and the crude material is dissolved in EtOAc (100 mL), washed with 1 N $NaHSO_4$ (2×50 mL) and brine (50 mL), and dried ($MgSO_4$). The solvent is removed in vacuo and the product is used directly in the next step without further purification.

7-F to 7-H: Intermediates 7-F to 7-H are prepared following methods analogous to those described for preparing the intermediates of Reference compound 1.

7-I: This compound is prepared from 7-H using methods analogous to those described for the preparation of intermediate 1-E for Reference compound 1. MS m/z 404.2 (M+1); $^1$H-NMR ($CDCl_3$, 400 MHz) d 7.66-7.64 (1H, m), 7.49-7.47 (1H, m), 7.31-7.26 (2H, m), 4.85-4.64 (1H, m), 3.44-3.16 (1H, m), 2.96-2.88 (2H, m), 1.80-1.55 (4H, m), 1.39-1.14 (13H, m), 0.89-0.72 (4H, m).

Reference compound 8 is prepared from (S)-Boc-nipecotic acid using methods analogous to those described for the preparation of Reference compound 6.

Reference compound 9

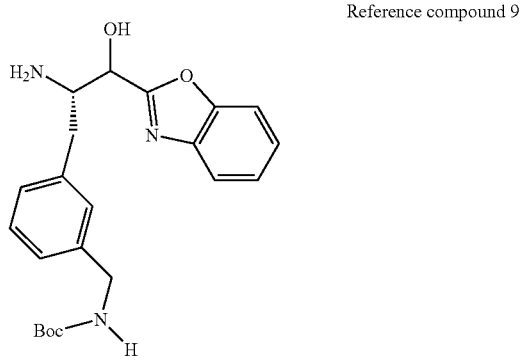

Reference compound 9 is prepared starting from 3-cyanophenylalanine using methods analogous to those described for the preparation of Reference compound 5.

Reference compound 10

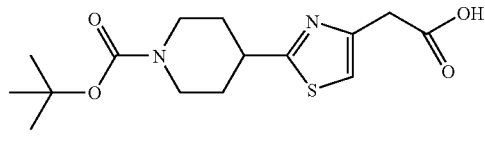

Reference compound 10 is prepared starting from Boc-isonipecotic acid using methods analogous to those described for the preparation of Reference compound 6.

Reference compound 8

Reference compound 11

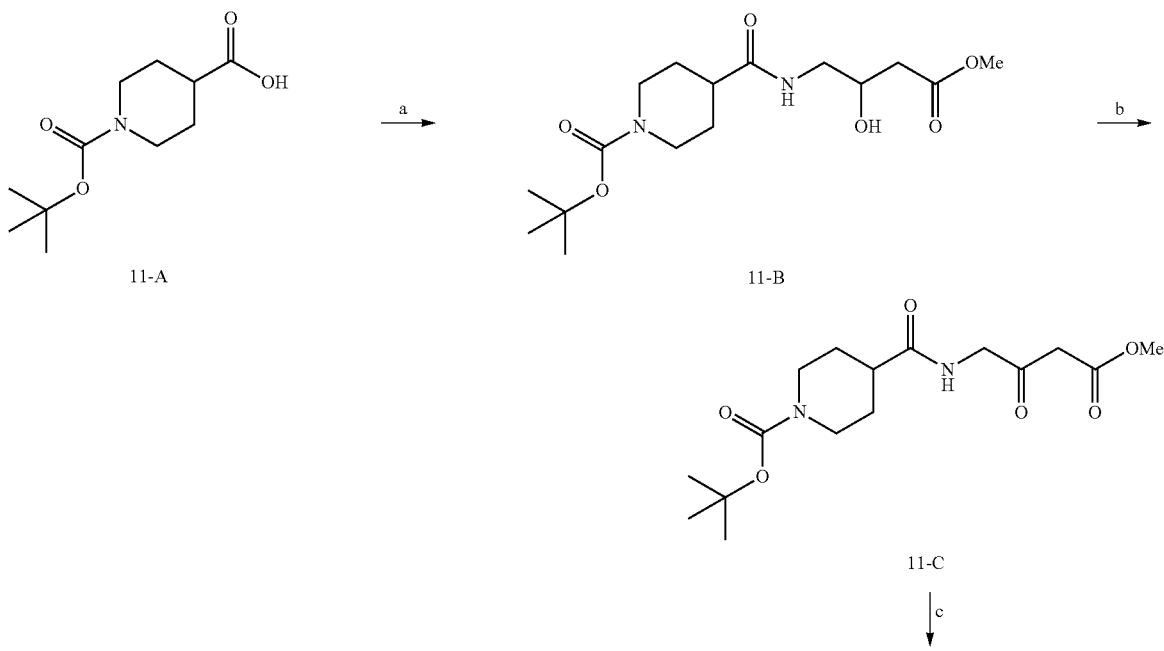

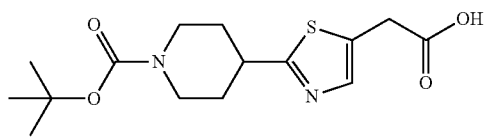
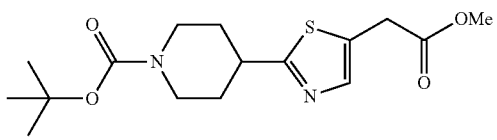

11-D

Boc-isonipecotic acid (3.24 g, 14.1 mmol), DL-4-Amino-3-hydroxy-butyric acid methyl ester hydrochloride (2.40 g, 14.1 mmol), and DIEA (7.0 mL, 42.3 mL) are dissolved in $CH_2Cl_2$ (50 mL). HATU (5.9 g, 15.5 mmol) is added, and the reaction mixture is stirred at room temperature for 2 h. The solvent is evaporated, and the crude residue is taken up in EtOAc (100 mL). The organic phase is washed with 0.1 M HCl (2×100 mL) and brine (100 mL), dried with $MgSO_4$, and evaporated in vacuo. The crude material is purified by silica gel flash chromatography (EtOAc/Hexanes gradient) to provide intermediate 11-B.

11-C: Alcohol 11-B is oxidized to the ketone using conditions analogous to those used for the preparation of Example 1-F.

11-D: Ketone 11-C (1.10 g, 3.21 mmol) is dissolved in THF (100 mL). Lawesson's reagent (650 mg, 1.61 mmol) is added, and the reaction mixture is stirred at room temperature for 48 h. The solvent is removed in vacuo, and the crude material is purified by silica gel flash chromatography (EtOAc/Hexanes 0:100 gradient).

11: The methyl ester 11-D is saponified using methods analogous to those described for the preparation of Reference compound 6.

Reference compound 12

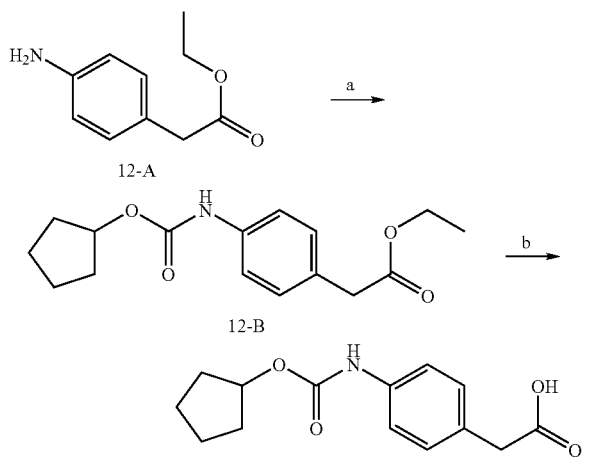

The reagents and conditions in the above reaction for Reference compound 12 are: a) (cyclohexylcarbonyloxy)succinimide, pyridine, DMAP, rt, THF; (b) 1 N NaOH in water.

(4-Amino-phenyl)-acetic acid ethyl ester (0.895 g, 5.0 mmol) and N-(cyclohexylcarbonyloxy)succinimide (1.051 g, 5.0 mmol) are added to a round bottomed flask containing THF (20 mL), pyridine (0.60 mL) and DMAP (10 mg). The mixture is stirred at room temperature overnight. The clear solution is diluted with EtOAc (200 mL), washed with 1N HCl (3×100 mL) and brine (100 mL), and dried with $MgSO_4$. Solvent is evaporated in vacuo to afford the intermediate 12-B as a white solid which is used without further purification.

The ethyl ester 12-B (1.46 g, 5 mmol) is dissolved in 1N NaOH (15 mL, 15 mmol). After the starting material had disappeared (by LCMS), the reaction is acidified with 1 N HCl, to afford Reference compound 12 as a white precipitate.

Reference compound 13

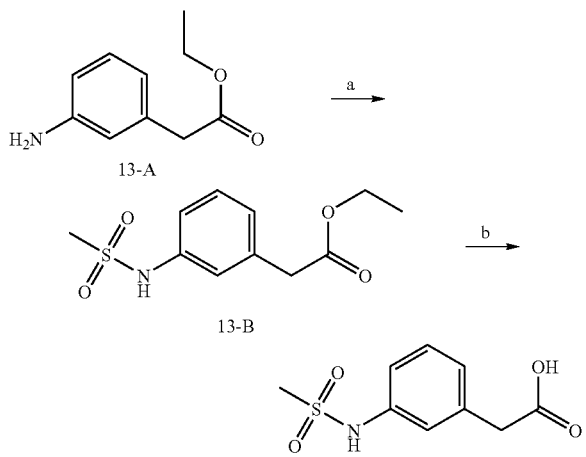

The reagents and conditions in the above reaction for Reference compound 13 are: a) $MeSO_2Cl$, Pyridine, rt, THF; (b) 1 N NaOH in water.

(3-Amino-phenyl)-acetic acid ethyl ester (0.895 g, 5.0 mmol) and (0.281 mL, 5.0 mmol) are added to a round bottomed flask containing THF (20 mL) and pyridine (0.60 mL). The mixture is stirred at room temperature overnight. The clear solution is diluted with EtOAc (200 mL), washed with 1N HCl (3×100 mL) and brine (100 mL), and dried with $MgSO_4$. The solvent is evaporated in vacuo to afford intermediate 13-B as a white solid. The ethyl ester 13-B is saponified following methods analogous to those described for the preparation for Reference compound 12, to afford Reference compound 13.

Reference compound 14

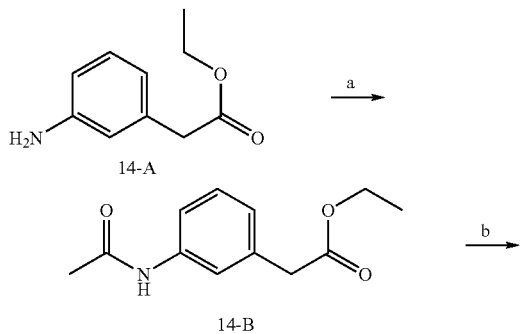

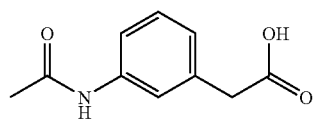

The reagents and conditions in the above reaction for Reference compound 14 are: a) CH$_3$COCl, Pyridine, DMAP, rt, THF; (b) 1 N NaOH in water.

(3-Amino-phenyl)-acetic acid ethyl ester (0.895 g, 5.0 mmol) and acetyl chloride (0.26 mL, 5.0 mmol) are added to a round bottomed flask containing THF (20 mL), pyridine (0.60 mL) and DMAP (10 mg). The mixture is stirred at room temperature overnight. The clear solution is diluted with EtOAc (200 mL), washed with 1N HCl (3×100 mL) and brine (100 mL), and dried with MgSO$_4$. Solvent is evaporated in vacuo to afford intermediate 14-B as a white solid that is used without further purification. The ethyl ester 14-B is saponified following methods analogous to those described above, to afford Reference compound 14.

Reference compound 15

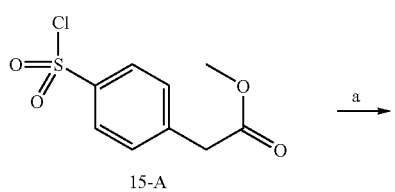
15-A

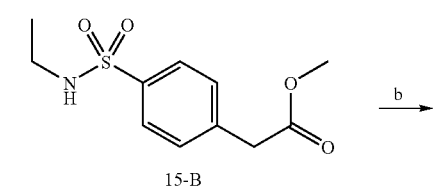
15-B

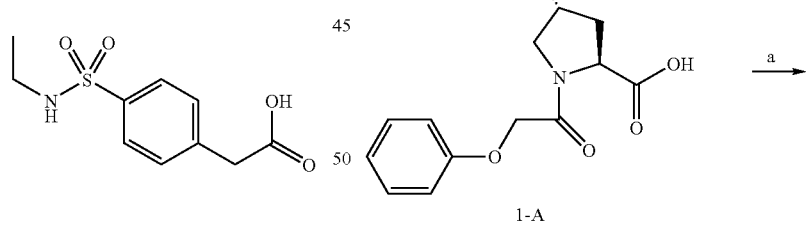

The reagents and conditions in the above reaction for Reference compound 15 are: a) EtNH$_2$, CH$_2$Cl$_2$, DMAP; (b) 1 N NaOH in water.

(4-Chlorosulfonyl-phenyl)-acetic acid methyl ester (0.895 g, 5.0 mmol) and diethylamine (1 mL) are added to a round bottomed flask containing CH$_2$Cl$_2$ (20 mL) and DMAP (10 mg). The mixture is stirred at room temperature overnight. The clear solution is diluted with EtOAc (200 mL), washed with 1N HCl (3×100 mL) and brine (1×100 mL), and dried with MgSO$_4$. Solvent is evaporated in vacuo to afford intermediate 15-B, which is purified from the reaction mixture using a silica column. The ethyl ester 15-B is saponified following methods analogous to those described above, to afford Reference compound 15.

Reference compound 16

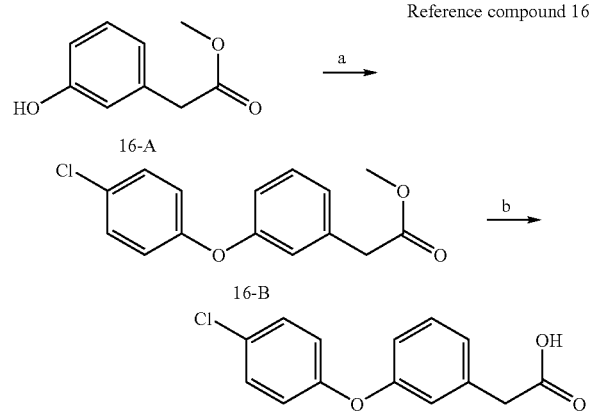

The reagents and conditions in the above reaction for Reference compound 16 are: a) 4-Cl-PhB(OH)$_2$, C$_2$H$_4$Cl$_2$, Cu(OAc)$_2$, pyridine, 4 Å molecular sieves; (b) 1 N NaOH in water.

(3-Hydroxy-phenyl)-acetic acid methyl ester (0.268 g, 1.6 mmol), 4-chlorophenyl boronic acid (755 mg, 4.84 mmol), pyridine (0.388 mL, 4.8 mmol) and copper(II) acetate (477 mg, 2.4 mmol) are added to a round bottomed flask containing 1,2-dichloroethane (10 mL) and 4 Å molecular sieves (300 mg). The mixture is stirred at room temperature overnight. The clear solution is diluted with EtOAc (200 mL), washed with 1N HCl (3×100 mL) and brine (100 mL), and dried with MgSO$_4$. Solvent is evaporated in vacuo to afford intermediate 16-B, which is purified from the reaction mixture using a silica column. The methyl ester 16-B is saponified following methods analogous to those described above, to afford Reference compound 16.

Example 1

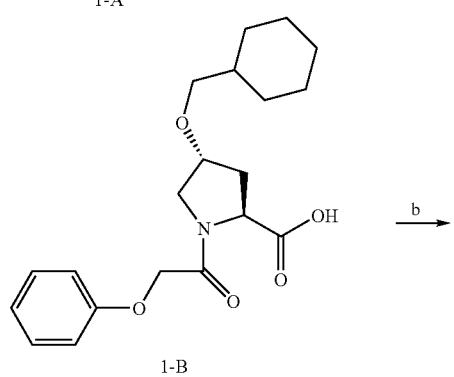

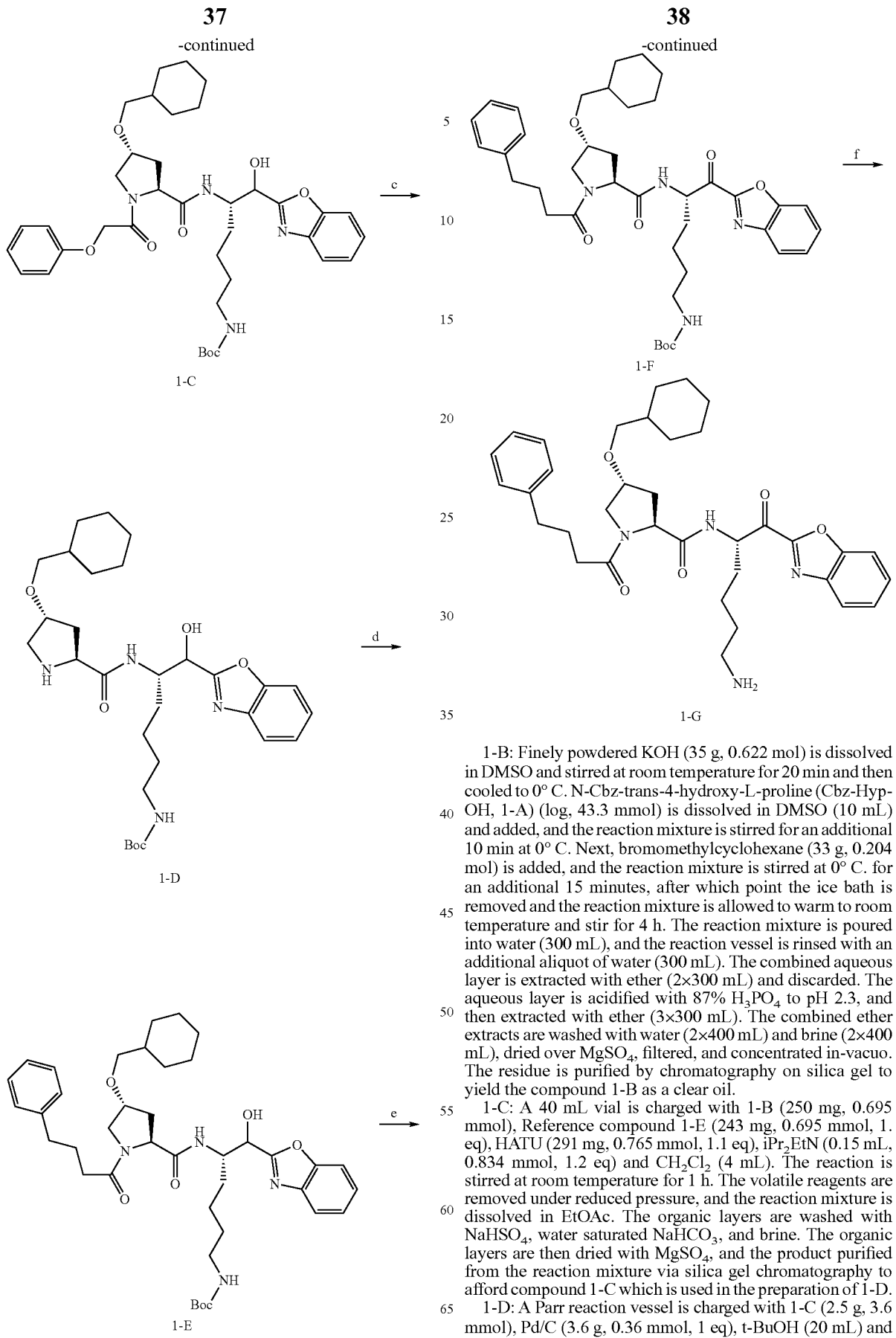

1-B: Finely powdered KOH (35 g, 0.622 mol) is dissolved in DMSO and stirred at room temperature for 20 min and then cooled to 0° C. N-Cbz-trans-4-hydroxy-L-proline (Cbz-Hyp-OH, 1-A) (log, 43.3 mmol) is dissolved in DMSO (10 mL) and added, and the reaction mixture is stirred for an additional 10 min at 0° C. Next, bromomethylcyclohexane (33 g, 0.204 mol) is added, and the reaction mixture is stirred at 0° C. for an additional 15 minutes, after which point the ice bath is removed and the reaction mixture is allowed to warm to room temperature and stir for 4 h. The reaction mixture is poured into water (300 mL), and the reaction vessel is rinsed with an additional aliquot of water (300 mL). The combined aqueous layer is extracted with ether (2×300 mL) and discarded. The aqueous layer is acidified with 87% $H_3PO_4$ to pH 2.3, and then extracted with ether (3×300 mL). The combined ether extracts are washed with water (2×400 mL) and brine (2×400 mL), dried over $MgSO_4$, filtered, and concentrated in-vacuo. The residue is purified by chromatography on silica gel to yield the compound 1-B as a clear oil.

1-C: A 40 mL vial is charged with 1-B (250 mg, 0.695 mmol), Reference compound 1-E (243 mg, 0.695 mmol, 1. eq), HATU (291 mg, 0.765 mmol, 1.1 eq), $iPr_2EtN$ (0.15 mL, 0.834 mmol, 1.2 eq) and $CH_2Cl_2$ (4 mL). The reaction is stirred at room temperature for 1 h. The volatile reagents are removed under reduced pressure, and the reaction mixture is dissolved in EtOAc. The organic layers are washed with $NaHSO_4$, water saturated $NaHCO_3$, and brine. The organic layers are then dried with $MgSO_4$, and the product purified from the reaction mixture via silica gel chromatography to afford compound 1-C which is used in the preparation of 1-D.

1-D: A Parr reaction vessel is charged with 1-C (2.5 g, 3.6 mmol), Pd/C (3.6 g, 0.36 mmol, 1 eq), t-BuOH (20 mL) and water (5 mL). The vessel is placed into a Parr apparatus and shaken for 18 h under a pressure of 50 psi of $H_2$ gas. The reaction mixture is filtered through a pad of Celite to afford compound 1-D, which is used directly in the preparation of 1-E.

1-E: A 40 mL vial is charged with 1-D (100 mg, 0.18 mmol), 4-phenylbutyric acid (30 mg, 0.18 mmol, 1. eq), HATU (75 mg, 0.20 mmol, 1.1 eq), $iPr_2EtN$ (0.04 mL, 0.22 mmol, 1.2 eq) and $CH_2Cl_2$ (2 mL). The reaction is stirred at room temperature for 1 h. The volatile reagents are removed under reduced pressure and the reaction mixture is dissolved in EtOAc. The organic layers are washed with $NaHSO_4$, water, saturated $NaHCO_3$, and brine. The organic layers are then dried with $MgSO_4$, and the product is purified from the reaction mixture via silica gel chromatography 1-E, which is used in the preparation of 1-F.

1-F: Alcohol 1-E (127 mg, 0.18 mmol) is dissolved in DCM (2 mL) and Dess-Martin periodinane (85 mg, 0.2 mmol) is added. The reaction mixture is stirred overnight at room temperature. The solvent is removed in vacuo, and the crude is purified by flash chromatography (4 g silica gel column) using a gradient of EtOAc:hexanes to afford the ketone 1-F as a white foam which is used in the preparation of 1-G.

1-G: Ketone 1-F (128 mg, 0.18 mmol) is dissolved in DCM (1 mL) and TFA 50% in DCM (5 mL) is added. The reaction is stirred at room temp for 2 h and the solvent is removed in vacuo. The crude material is purified by reverse-phase HPLC, and the solvent is lyophilized to afford 1-G as a white powder.

Examples 2-7

Example 2 is prepared following methods analogous to those described for Example 1, using 3-tert-butoxycarbonylamino-propionic acid to afford intermediate 2-E.

Example 3 is prepared following methods analogous to those described for Example 1, using Reference compound 13 to afford intermediate 3-E.

Example 4 is prepared following methods analogous to those described for Example 1, using Reference compound 14 to afford intermediate 4-E.

Example 5 is prepared following methods analogous to those described for Example 1, using (4-ethanesulfonylamino-phenyl)-acetic acid (prepared in a manner analogous to those described for Reference compound 13) to afford intermediate 5-E.

Example 6 is prepared following methods analogous to those described for Example 1, using Reference compound 12 to afford intermediate 6-E.

Example 7 is prepared following methods analogous to those described for Example 1, using 4-(methanesulfonylamino)phenylacetic acid to afford intermediate 7-E.

Example 8

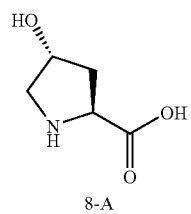

8-A

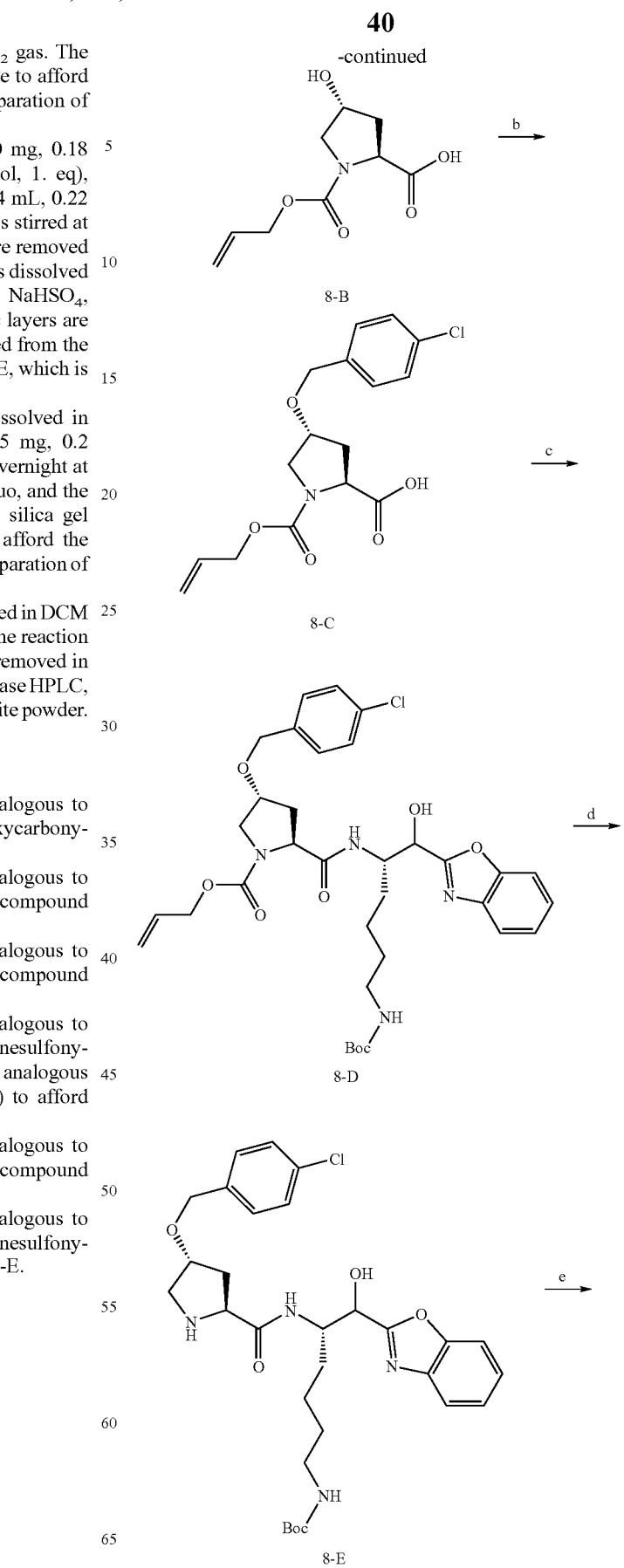

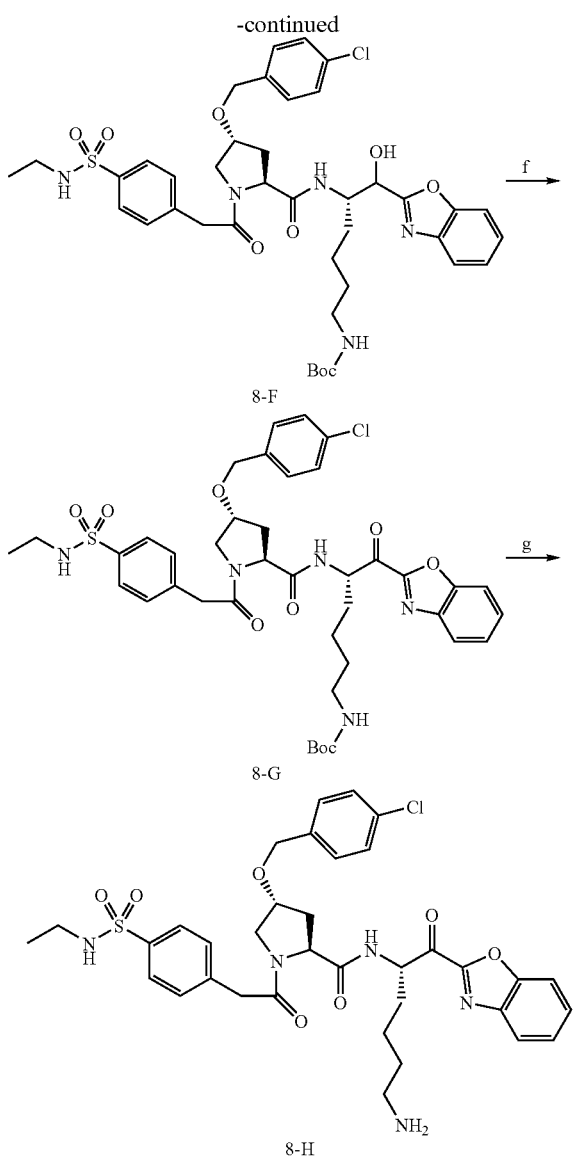

dppe (26 mg, 0.06 mmol, 0.05 eq) and THF (5 mL). The reagents are stirred at room temperature for 15 min and then concentrated to dryness. The product (as a mixture of diastereomers) is purified from the reaction mixture via silica gel chromatography using a 2-9% MeOH in $CH_2Cl_2$ gradient. The amine 8-E is then used in the preparation of 8-F.

8-F: Following methods analogous to those described for the preparation of intermediate 1-E in Example 1, compound 8-F is prepared by HATU coupling of 8-E and (4-ethanesulfonylamino-phenyl)-acetic acid (prepared in a manner analogous to those described for the preparation of the 4-(methanesulfonylamino)phenylacetic acid, which was prepared using methods analogous to those described for the preparation of reference compound 13).

8-G: This compound is prepared by oxidation of 8-F using methods analogous to those described for the preparation of intermediate 1-F in Example 1.

8-H: This compound is prepared by deprotection of 8-G using methods analogous to those described for the preparation Example 1.

Examples 9-30

Example 9 is prepared following methods analogous to those described for Example 8, using Reference compound 15 to afford intermediate 9-F.

Example 10 is prepared following methods analogous to those described for Example 8, using (4-methoxy-phenyl)-acetic acid to afford intermediate 10-F.

Example 11 is prepared following methods analogous to those described for Example 8, using pyridin-4-yl-acetic acid to afford intermediate 11-F.

Example 12 is prepared following methods analogous to those described for Example 8, using (3-chloro-phenyl)-acetic acid to afford intermediate 12-F.

Example 13 is prepared following methods analogous to those described for Example 8, using [4-(morpholine-4-sulfonyl)-phenyl]-acetic acid to afford intermediate 13-F.

Example 14 is prepared following methods analogous to those described for Example 8, using (3,5-dichloro-phenyl)-acetic acid to afford intermediate 14-F.

Example 15 is prepared following methods analogous to those described for Example 8, using (4-phenyl-phenyl)-acetic acid to afford intermediate 15-F.

Example 16 is prepared following methods analogous to those described for Example 8, using (2-chloro-phenyl)-acetic acid to afford intermediate 16-F.

Example 17 is prepared following methods analogous to those described for Example 8, using (3-phenoxy-phenyl)-acetic acid to afford intermediate 17-F.

Example 18 is prepared following methods analogous to those described for Example 8, using (2-phenyl-thiazol-4-yl)-acetic acid to afford intermediate 18-F.

Example 19 is prepared following methods analogous to those described for Example 8, using (4-phenylmethanesulfonylamino-phenyl)-acetic acid (prepared in a manner analogous to those described for the preparation of the reference compound 13) to afford intermediate 19-F.

Example 20 is prepared following methods analogous to those described for Example 8, using [4-(piperidine-1-sulfonyl)-phenyl]-acetic acid to afford intermediate 20-F.

Example 21 is prepared following methods analogous to those described for Example 8, using [3-(4-chloro-phenoxy)-phenyl]-acetic acid reference compound 16 to afford intermediate 21-F.

Example 22 is prepared following methods analogous to those described for Example 8, using [4-(trifluoro-ethane- 8-B: trans-4-Hydroxyproline (Hyp-OH) (7.90 g, 60.1 mmol) and N-(allyloxycarbonyloxy)succinimide (12.0 g, 60.1 mmol) are added to a round bottomed flask containing THF (220 mL), triethylamine (21 mL, 150.3 mmol) and water (55 mL). The mixture is stirred at room temperature overnight. The clear solution is acidified with 1N HCl (100 mL) and extracted with EtOAc (4×150 mL). The combined organic layer is washed with brine (100 mL) and dried with $MgSO_4$. Solvent is evaporated in vacuo to afford the desired product as a white solid, which is used without further purification.

8-C: This compound is prepared by alkylation of 8-B and 1-chloro-4-chloromethyl-benzene using methods analogous to those described for the preparation of intermediate 1-B in Example 1.

8-D: This compound is prepared by HATU coupling of 8-C and reference compound 1-E using methods analogous to those described for the preparation of intermediate 1-C in Example 1.

8-E: A 50 mL round bottom flask is charged with alcohol 8-D (780 mg, 1.16 mmol), $Et_2NH$ (1.8 mL, 17.43 mmol, 15 eq), $Pd_2(dba)_3$ (55 mg, 0.06 mmol 0.05 eq), phosphine ligand sulfonylamino)-phenyl]-acetic acid (following methods analogous to those described for Reference compound 13) to afford intermediate 22-F.

Example 23: This compound is prepared from 1-Boc-piperidin-4-yl-propionic acid following methods analogous to those described for the preparation of Example 8.

Example 24: This compound is prepared from N-Boc-4-piperidin-4-yl-butyric acid following methods analogous to those described for the preparation of Example 8.

Example 25: This compound is prepared from 1-Boc-piperidin-4-yl-acetic acid following methods analogous to those described for the preparation of Example 8.

Example 26: This compound is prepared from 1-Boc-piperidin-3-yl-acetic acid following methods analogous to those described for the preparation of Example 8.

Example 27: This compound is prepared from 1-Boc-piperidin-3-yl-propionic acid following methods analogous to those described for the preparation of Example 8.

Examples 28-30 are prepared following methods analogous to those described for the preparation of Example 8.

Example 31

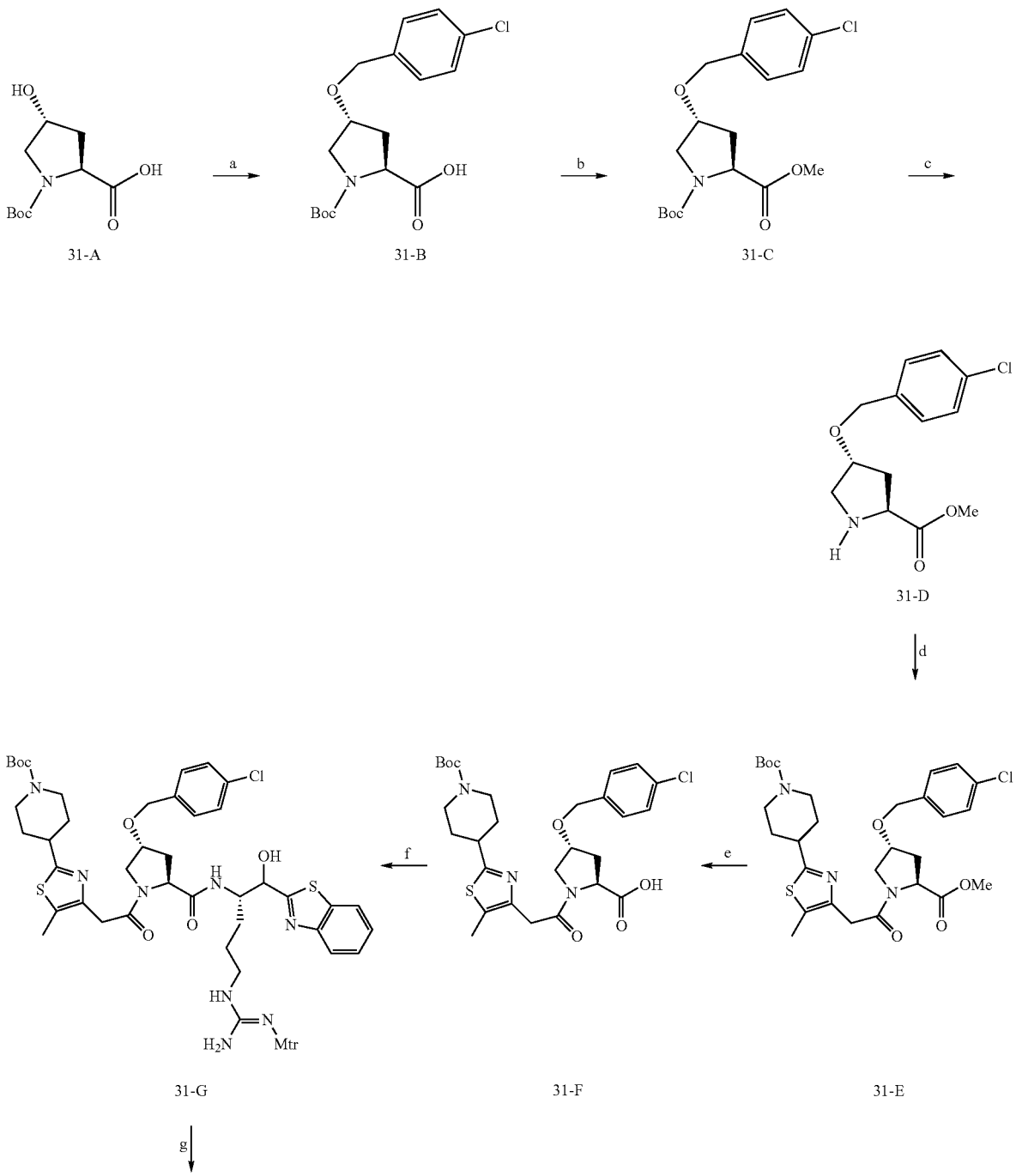

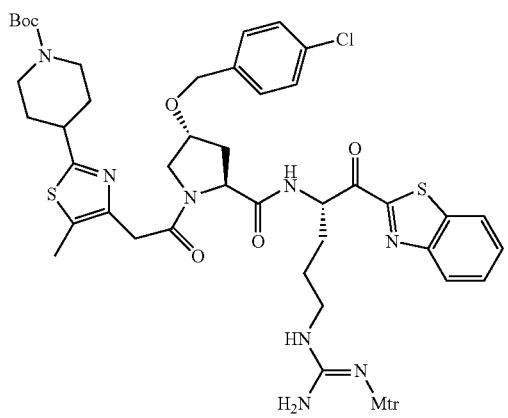

31-H

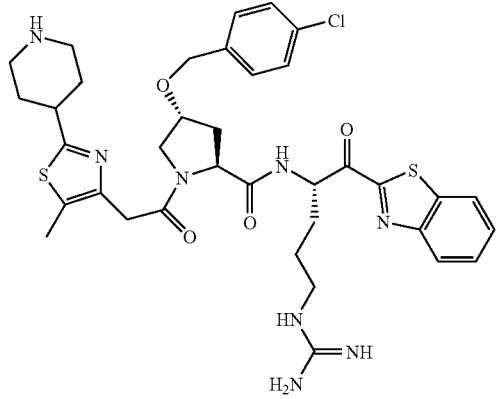

Example 31

31-B: Finely powdered KOH (19.4 g, 0.346 mol) is dissolved in DMSO and stirred at room temperature for 20 min and then cooled to 0° C. N-Boc-trans-4-hydroxy-L-proline (Boc-Hyp-OH, 1-A) (10 g, 43.3 mmol) is dissolved in DMSO (10 mL) and added, and the reaction mixture is stirred for an additional 10 min at 0° C. Next, 4-chlorobenzyl chloride (33 g, 0.204 mol) is added, and the reaction mixture is stirred at 0° C. for an additional 15 min, after which point the ice bath is removed and the reaction mixture is allowed to warm to room temperature and stir for 4 h. The reaction mixture is poured into water (300 mL), and the reaction vessel is rinsed with an additional aliquot of water (300 mL). The combined aqueous layer is extracted with ether (2×300 mL) and discarded. The aqueous layer is acidified with 87% $H_3PO_4$ to pH 2.3, and then extracted with ether (3×300 mL). The combined ether extracts are washed with water (2×400 mL) and brine (2×400 mL), dried over $MgSO_4$, filtered and concentrated in vacuo. The residue is purified by chromatography on silica gel with EtOAc/Hexanes (gradient 0 to 100%) to yield the compound 1-B as a clear oil. MS m/z 256.1 (M+1-Boc); $^1$H NMR (DMSO-$D_6$, 400 MHz) δ 7.39-7.31 (4H, m), 4.52-4.40 (2H, m), 4.16-4.10 (2H, m), 3.48-3.41 (2H, m), 2.40-2.30 (1H, m), 2.03-1.94 (1H, m), 1.39-1.34 (9H, m).

31-C: A solution of (trimethylsilyl)diazomethane (2M in diethylether) (4.7 mL, 9.45 mmol) is added to carboxylic acid 1-B (2.4 g, 8.6 mmol) dissolved in DCM/MeOH (5:1, 25 mL). When the starting material had been consumed, as determined by LCMS, the reaction mixture is concentrated in vacuo, and the crude residue is purified by flash chromatography (gradient EtOAc:Hexanes) to afford the methyl ester as a clear oil.

31-D: A round bottomed flask is charged with a stirbar and 1-C (510 mg, 1.38 mmol). TFA (50%) in DCM (6 mL) is added and the solution is stirred for 1 h at room temperature. The solvent is removed in vacuo, hexanes is added and then evaporated again in vacuo to dryness, and repeated if necessary to azeotrope remaining TFA. The crude material is used directly in the next step without further purification.

31-E: This compound is prepared from 31-D and commercially available {2-[1-(tert-butoxycarbonyl)piperidin-4-yl]-5-methyl-1,3-thiazol-4-yl}acetic acid using methods analogous to those described for the preparation of Example 1-E.

31-F: This compound is prepared from 31-E by saponification according to the methods described for the preparation of Reference Compound 6.

31-G: This compound is prepared from 31-F and Reference Compound 3 using methods analogous to those described for the preparation of Example 1-C.

31-H: This compound is prepared from 31-G using methods analogous to those described for the preparation of Example 1-F.

31: Reference compound 31 is prepared from 31-H using methods analogous to those described for the preparation of Example 1-G.

Examples 32-43

Example 32 is prepared from Reference compound 10 following methods analogous to those described for the preparation of Example 31.

Example 33 is prepared following methods analogous to those described for the preparation of Example 31.

Example 34 is prepared from Reference compound 11 following methods analogous to those described for the preparation of Example 8.

Example 35 is prepared from Reference compound 8 following methods analogous to those described for the preparation of Example 8.

Example 36 is prepared from Reference compound 6 following methods analogous to those described for the preparation of Example 8.

Example 37 is prepared from Reference compound 2 following methods analogous to those described for the preparation of Example 8.

Example 38 is prepared from Reference compound 2 following methods analogous to those described for the preparation of Example 8.

Example 39 is prepared from Reference compound 2 following methods analogous to those described for the preparation of Example 8.

Example 40 is prepared from Reference compound 5 and {2-[1-(tert-butoxycarbonyl)piperidin-4-yl]-5-methyl-1,3-thiazol-4-yl}acetic acid following methods analogous to those described for Example 8.

Example 41 is prepared from Reference compound 9 and {2-[1-(tert-butoxycarbonyl)piperidin-4-yl]-5-methyl-1,3-thiazol-4-yl}acetic acid following methods analogous to those described for Example 8.

Example 42 is prepared from Reference compound 7 and {2-[1-(tert-butoxycarbonyl)piperidin-4-yl]-5-methyl-1,3-thiazol-4-yl}acetic acid following methods analogous to those described for Example 8.

Example 43 is prepared from Reference compound 2 and {2-[1-(tert-butoxycarbonyl)piperidin-4-yl]-5-methyl-1,3-thiazol-4-yl}acetic acid following methods analogous to those described for Example 8.

Table 1 shows compounds of Formula (1), as described in Examples 1-42.

TABLE 1

| Example | Structure | Physical Data MS (m/z), Elemental Analysis, and $^1$H NMR 400 MHz (DMSO-$d_6$) |
|---|---|---|
| 1 | 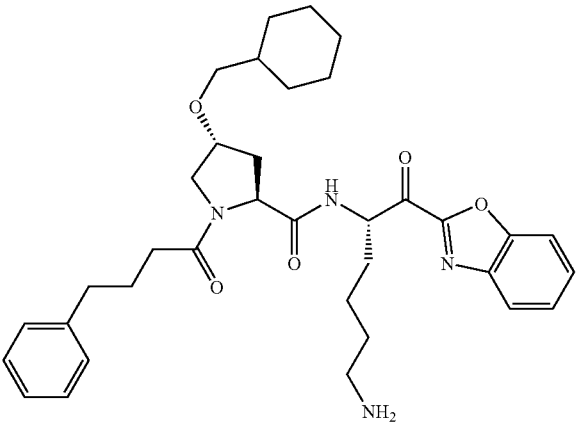 | MS m/z 603.4 (M + 1); $^1$H NMR δ 8.08 (s, 2H), 7.90(d, 1H J=8.0Hz), 7.66(d, 1H J=8.0Hz), 7.53-7.57(m, 1H), 7.45-7.49(m, 2H), 7.14-7.19(m, 3H), 5.70-5.71(m, 1H), 4.47-4.51(m, 1H), 4.10 (s, 1H), 3.63-3.66(m, 3H), 3.38-3.41 (m, 1H), 3.01-3.22(m, 3H), 3.02(s, 2H), 2.60-2.65(m, 2H), 2.23-2.28(m, 4H), 2.06-2.13(m, 1H), 1.85-1.89(m, 3H), 1.46-1.51(m, 2H), 1.11-1.23(m, 4H), 0.85-0.89(m, 3H). |
| 2 | 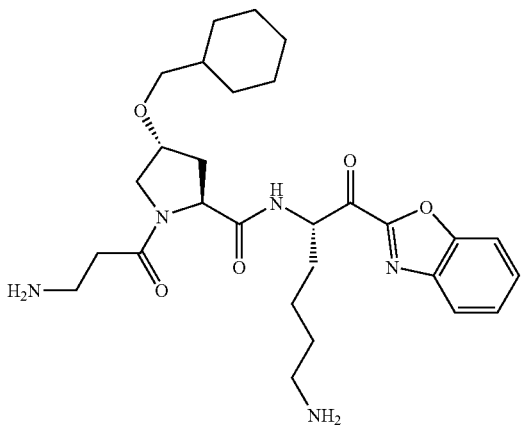 | MS m/z 528.4 (M + 1); $^1$H NMR δ 7.90-7.48(m, 8H), 5.62-5.71(m, 1H), 4.49-4.51(m, 1H), 4.15(s, 1H), 3.82-4.00 (m, 1H), 3.66-3.74(m, 1H), 3.30(s, 1H), 3.00-3.22(m, 4H), 2.51-2.61(m, 2H), 2.00-2.40(m, 3H), 1.43-1.81(m, 12H), 1.1-1.26(m, 3H), 0.80-0.92(m, 3H) |
| 3 | 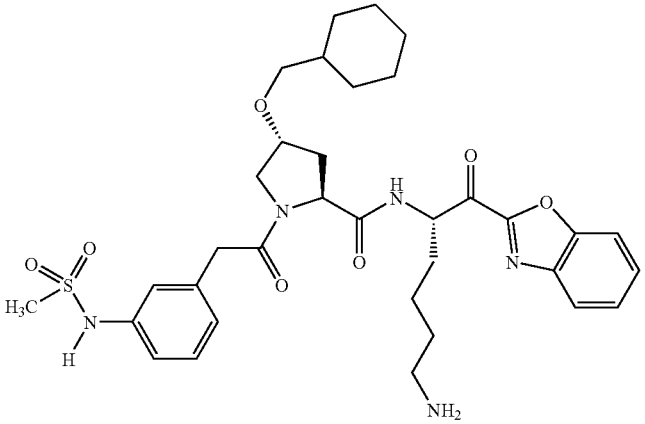 | MS m/z 668.4 (M + 1); $^1$H NMR δ 8.04 (d, 1H J=8.0Hz), 7.80(d, 1H J= 8.0Hz), 7.68-7.72(m, 1H), 7.60-7.64 (m, 1H), 7.49-7.53(m, 3H), 7.32(d, 2H J=8.0Hz), 7.27(s, 1H), 7.13(d, 1H J= 8.0Hz), 4.63-4.67(m, 1H), 4.32(s, 1H), 3.98-4.01(m, 1H), 3.80(s, 3H), 3.35-3.37(m, 2H), 3.27-3.31(m, 2H), 3.11-3.19(m, 10H), 4.83(s, 1H), 2.42-2.48 (m, 1H), 2.34-2.35(m, 1H), 2.24-2.30 (m, 1H), 1.26-1.41(m, 4H), 0.99-1.07 (m, 3H). |

TABLE 1-continued

| Example | Structure | Physical Data<br>MS (m/z), Elemental Analysis, and<br>¹H NMR 400 MHz (DMSO-d₆) |
|---|---|---|
| 4 | 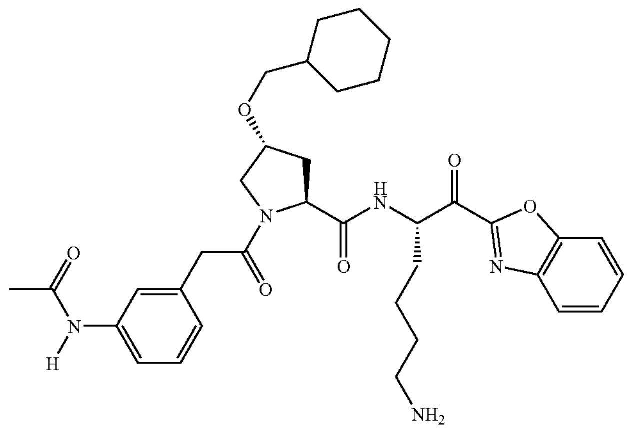 | MS m/z 632.4 (M + 1); ¹H NMR δ 8.30 (s, 1H), 7.91(d, 1H J=8.0Hz), 7.67(d, 1H J=8.0Hz), 7.47-7.59(m, 2H), 7.37 (s, 1H), 7.30(d, 1H J=8.0Hz), 7.17-7.19(m, 3H), 7.97-7.99(m, 1H), 5.71-5.77(m, 1H), 4.40-4.44(m, 1H), 4.20 (s, 1H), 3.84-3.87(m, 2H), 3.16-3.26 (m, 2H), 2.844(s, 1H), 2.69(s, 1H), 2.23-2.37(m, 2H), 2.17(s, 3H), 1.14-1.27(m, 4H), 0.86-0.97(m, 3H). |
| 5 | 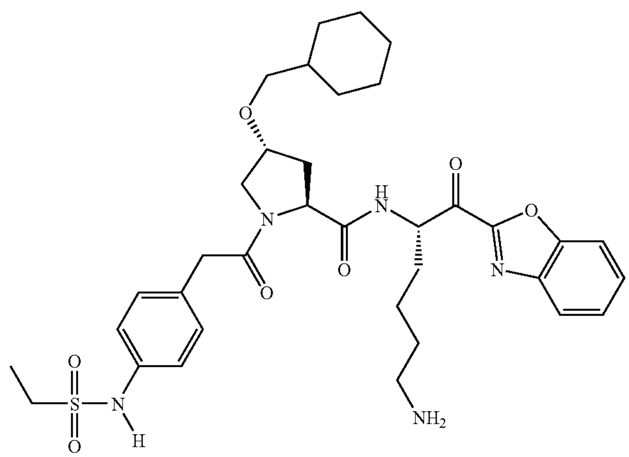 | MS m/z 682.4 (M + 1); ¹H NMR δ 7.92 (d, 1H J=8.0Hz), 7.76(d, 1H J= 8.0Hz), 7.61-7.65(m, 1H), 7.52-7.55 (m, 1H), 7.20-7.23(m, 6H), 5.58-5.61 (m, 1H), 4.51-4.55(m, 1H), 4.10-4.14 (m, 2H), 3.66-3.79(m, 5H), 3.19-3.23 (m, 2H), 3.06-3.13(m, 5H), 2.92-2.95 (m, 2H), 2.66(s, 1H), 2.32-2.37(m, 1H), 2.17-2.24(m, 1H), 1.94-2.01(m, 1H), 1.27-1.32(m, 7H), 0.84-0.98(m, 3H). |
| 6 | 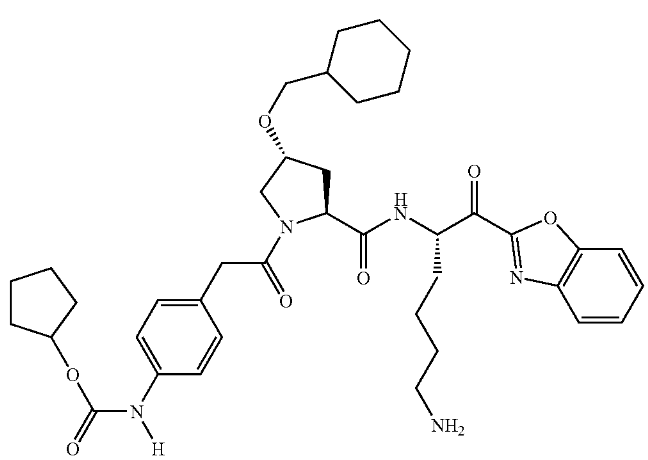 | MS m/z 702.4 (M + 1); ¹H NMR δ 7.91 (d, 1H J=8.0Hz), 7.76(d, 1H J= 8.0Hz), 7.61-7.65(m, 1H), 7.52-7.55 (m, 1H), 7.34-7.41(m, 3H), 7.20(d, 2H J=8.0Hz), 5.61-5.64(m, 1H), 5.12-5.15 (m, 1H), 4.48-4.53(m, 3H), 4.08(s, 1H), 3.63-3.78(m, 5H), 3.11-3.15(m, 1H), 2.98-3.01(m, 1H), 2.91-2.94(m, 3H), 2.66(s, 1H), 2.31-2.34(m, 1H), 2.18-2.26(m, 1H), 1.82-1.99(m, 4H), 1.38-1.42(m, 2H), 1.14-1.29(m, 5H), 0.81-0.94(m, 3H). |

TABLE 1-continued

| Example | Structure | Physical Data MS (m/z), Elemental Analysis, and $^1$H NMR 400 MHz (DMSO-$d_6$) |
|---|---|---|
| 7 | 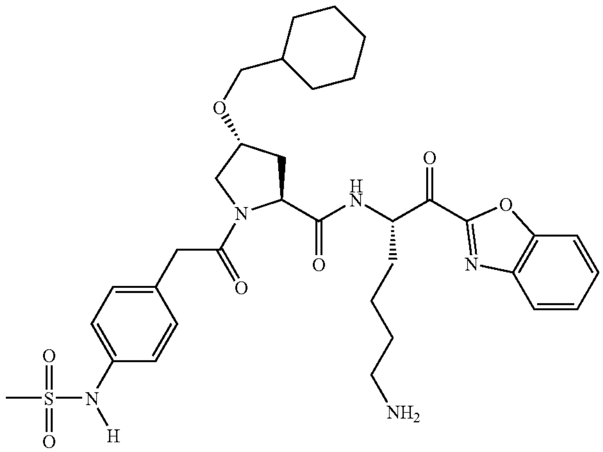 | MS m/z 668.3 (M + 1) |
| 8 | 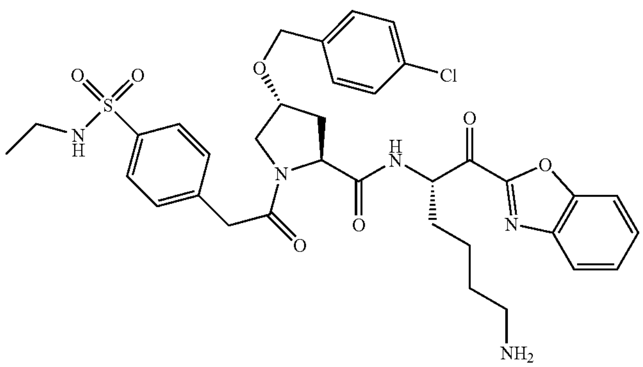 | MS m/z 710.4 (M + 1); $^1$H NMR δ 7.95 (d, 1H J=8.0Hz), 7.78-7.81(m, 2H), 7.63-7.67(m, 1H), 7.51-7.58(m, 2H), 7.46-7.49(m, 2H), 7.38-7.41(m, 2H), 7.31(d, 2H J=8.0Hz), 6.84(s, 2H), 5.54-5.61(m, 1H), 4.43-4352(m, 2H), 4.27-4.29(m, 1H), 3.83(s, 2H), 3.75(s, 2H), 2.89(d 3H, J=8.0Hz), 2.30-2.36 (m, 1H), 2.10-2.19(m, 1H), 2.01-2.08 (m, 1H), 1.57-1.75(m, 4H), 1.03-1.07 (m, 2H). |
| 9 | 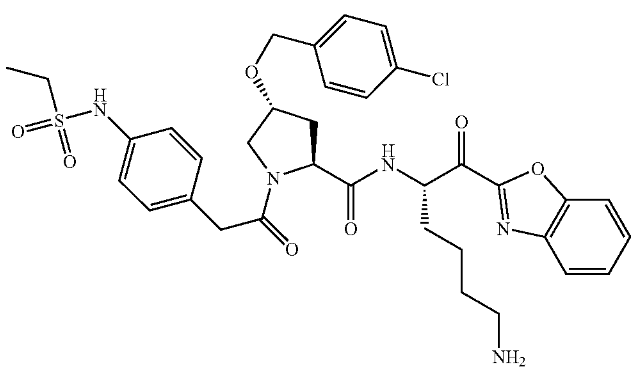 | MS m/z 710.4 (M + 1); C$_{37}$H$_{41}$ClF$_3$N$_5$O$_9$S (M + TFA) C calcd, 53.91 found, 50.06; H calcd, 5.01 found, 4.74; N calcd, 8.50 found, 7.64; $^1$H NMR δ 7.91-7.96(m, 1H), 7.75-7.80 (m, 1H), 7.63-7.67(m, 1H), 7.50-7.57 (m, 1H), 7.37-7.41(m, 2H), 7.29-7.32 (m, 2H), 7.24(s, 4H), 4.43-4.51(m, 2H), 4.28(s, 1H), 3.70(s, 2H), 3.06-3.12(m, 2H), 3.80-3.92(m, 3H), 2.29-2.32(m, 1H), 2.12-2.16(m, 1H), 1.58-1.76(m, 4H), 1.27-1.31(m, 3H) |
| 10 | 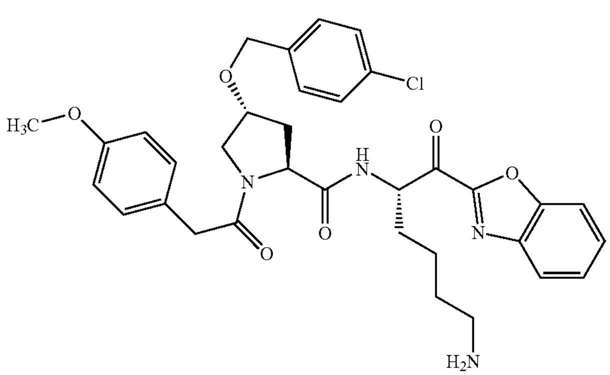 | MS m/z 633.4 (M + 1); $^1$H NMR δ 7.93 (d, 1H J=8.0Hz), 7.78(d, 1H J= 8.0Hz), 7.62-7.66(m, 1H), 7.52-7.59 (m, 2H), 7.35-7.41(m, 2H), 7.27(d, 2H J=8.0Hz), 7.14-7.19(m, 2H), 6.88(d, 2H J=8.0Hz), 7.53-7.59(m, 1H), 4.37-4.48(m, 3H), 4.25-4.26(m, 2H), 4.09 (s, 4H), 3.77(s, 3H), 4.64(s, 2H), 2.88 (s, 2H), 2.28-2.34(m, 1H), 2.10-2.18 (m, 1H), 1.99-2.05(m, 1H), 1.58-1.77 (m, 5H). |

TABLE 1-continued
| Example | Structure | Physical Data MS (m/z), Elemental Analysis, and ¹H NMR 400 MHz (DMSO-d₆) |
|---|---|---|
| 11 | 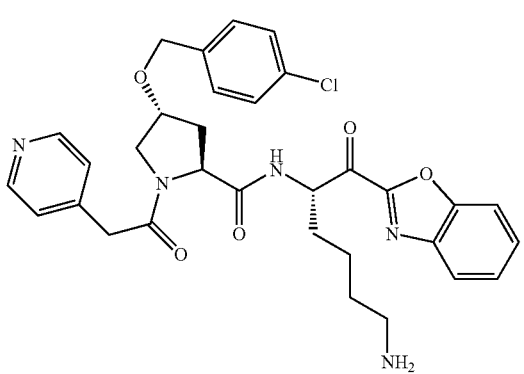 | MS m/z 604.3 (M + 1), ¹H NMR δ 7.93 (d), 8.72(s, 1H), 7.78-7.81(m, 1H), 7.50-7.67(m, 2H), 7.34-7.41(m, 3H), 7.02(s, 2H), 5.47-5.53(m, 1H), 4.46-4.56(m, 2H), 4.29-4.31(m, 1H), 3.95-4.02(m, 2H), 3.73-3.82(m, 2H), 2.86 (s, 2H), 2.54(s, 2H), 2.31-2.37(1H), 2.06-2.15(m, 1H), 1.52-1.74(m, 3H). |
| 12 | 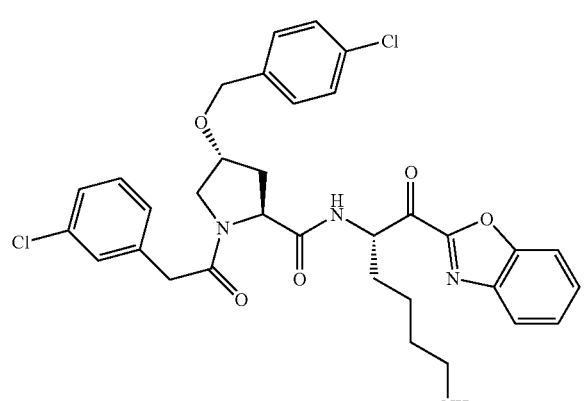 | MS m/z 637.2 (M + 1) |
| 13 | 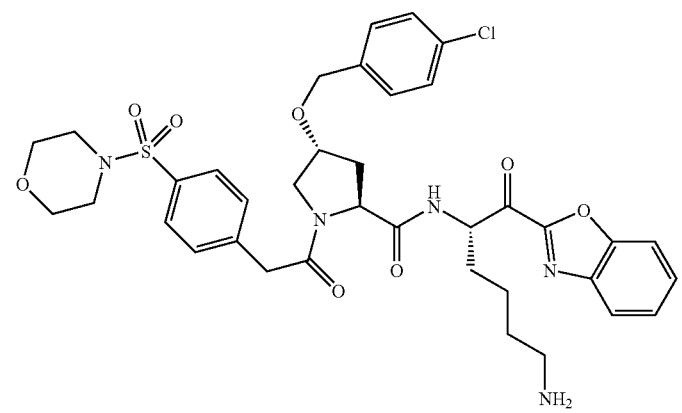 | MS m/z 752.3 (M + 1) |

TABLE 1-continued
| Example | Structure | Physical Data MS (m/z), Elemental Analysis, and $^1$H NMR 400 MHz (DMSO-$d_6$) |
|---|---|---|
| 14 | 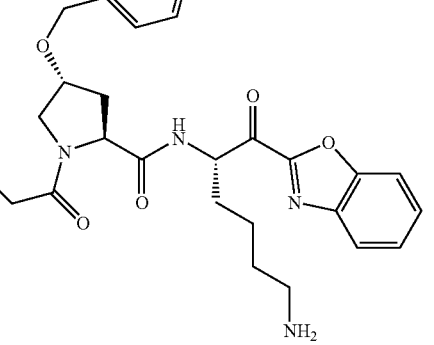 | MS m/z 671.2 (M + 1) |
| 15 | 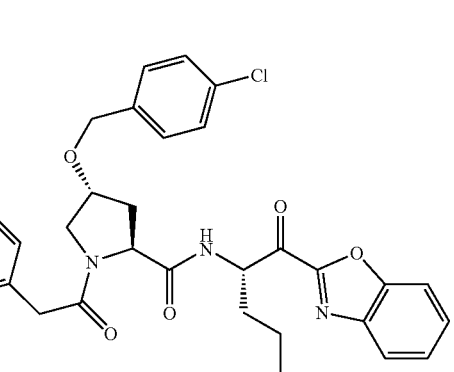 | MS m/z 679.3 (M + 1) |
| 16 | 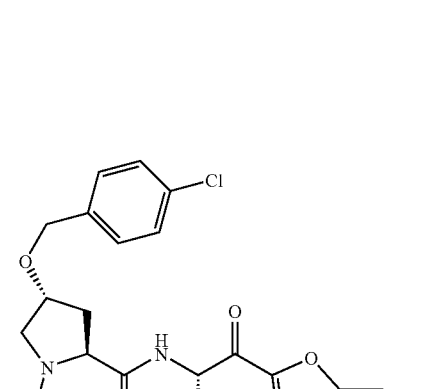 | MS m/z 637.2 (M + 1) |

TABLE 1-continued

| Example | Structure | Physical Data MS (m/z), Elemental Analysis, and $^1$H NMR 400 MHz (DMSO-$d_6$) |
|---|---|---|
| 17 | 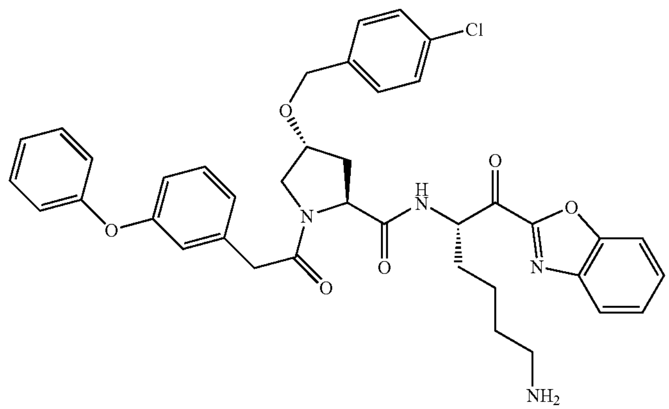 | MS m/z 695.3 (M + 1) |
| 18 | 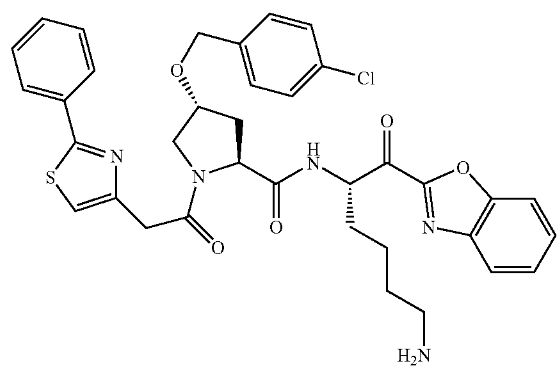 | MS m/z 686.3 (M + 1); $^1$H NMR δ 7.93 (d), 7.94-7.95(m, 3H), 7.79(d, 1H J= 8.0Hz), 7.63-7.67(m, 1H), 7.49-7.58 (m, 5H), 7.40(s, 1H), 7.27-7.35(m, 5H), 7.03(s, 2H), 7.50-7.55(m, 1H), 4.45-4.53(m, 3H), 4.31(s, 1H), 4.02(d, 1H J=8.0Hz), 3.93(d, 2H J=5.2Hz), 3.82-3.86(m, 1H), 2.32-2.38(m, 2H), 2.09-2.14(m, 1H), 1.63-1.78(m, 7H). |
| 19 | 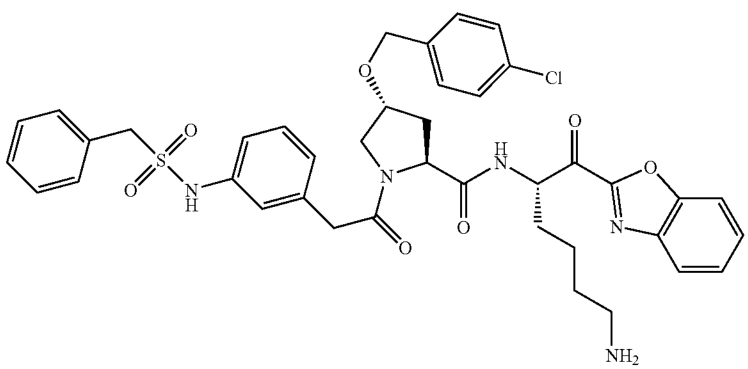 | MS m/z 772.3 (M + 1); $^1$H NMR δ 8.14 (s, 1H), 7.93(d, 1H J=8.0Hz), 7.75-7.78(m, 2H), 7.61-7.66(m, 1H), 7.52-7.56(m, 1H), 7.37-738(m, 6H), 7.30-7.32(m, 5H), 7.18-7.25(m, 6H), 7.50-7.55(m, 1H), 4.44-4.52(m, 3H), 4.37 (s, 3H), 4.27-4.27(m, 1H), 3.75(d, 2H J= 3.2Hz), 3.68(s, 2H), 2.88(s, 3H), 2.29-2.35(m, 1H), 1.99-2.15(m, 2H), 1.56-1.75(m, 6H). |
| 20 | 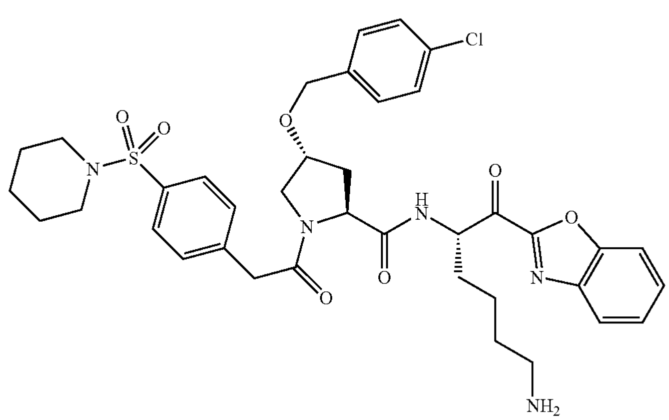 | MS m/z 750.3 (M + 1); $^1$H NMR δ 7.93 (d, 1H J=8.0Hz), 7.77(d, 1H J= 8.4Hz), 7.62-7.73(m, 4H), 7.47-7.56 (m, 3H), 7.37-7.39(m, 3H), 7.29-7.31 (m, 2H), 5.48-5.53(m, 1H), 4.40-4.55 (m, 3H), 4.24-4.26(m, 1H), 3.82(s, 2H), 3.73(d, 2H J=3.2Hz), 2.30-2.36 (m, 1H), 2.01-2.17(m, 2H), 1.66-1.79 (m, 3H), 1.57-1.62(m, 8H), 1.36-1.41 (m, 3H). |

TABLE 1-continued

| Example | Structure | Physical Data MS (m/z), Elemental Analysis, and ¹H NMR 400 MHz (DMSO-$d_6$) |
|---|---|---|
| 21 | 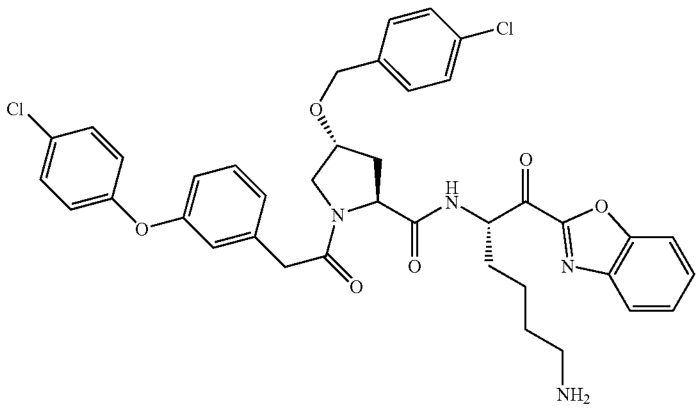 | MS m/z 729.3 (M + 1); ¹H NMR δ 7.93 (d, 1H J=8.0Hz), 7.77(d, 1H J= 8.0Hz), 7.72(d, 1H J=8.0Hz), 7.61-7.65(m, 1H), 7.51-7.56(m, 1H), 7.33-7.39(m, 8H), 7.27(d, 2H J=8.0Hz), 6.90-7.07(m, 5H), 5.48-5.54(m, 1H), 4.37-4.52(m, 3H), 4.22(s, 1H), 3.65-3.74(m, 5H), 3.01(s, 1H), 2.90-2.91 (m, 1H), 2.88(s, 1H), 2.27-2.33(m, 1H), 2.08-2.14(m, 1H), 1.99-2.05(m, 1H), 1.65-1.81(m, 3H), 1.57-1.62(m, 2H). |
| 22 | 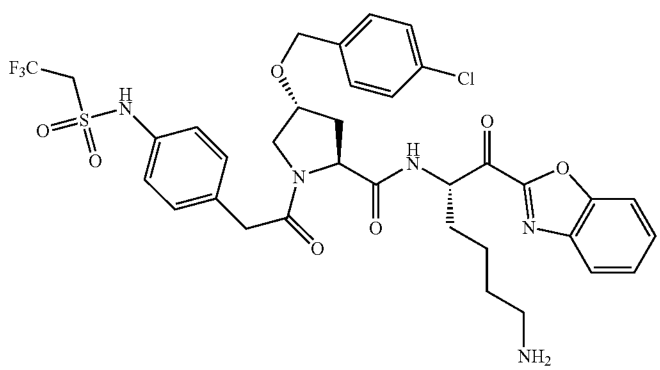 | MS m/z 764.2 (M + 1); ¹H NMR δ 7.93 (d), 8.94(s, 1H), 7.94(d, 1H J=8.0Hz), 7.79(d, 1H J=8.0Hz), 7.63-7.67(m, 1H), 7.53-7.57(m, 2H), 7.39-7.41(m, 2H), 7.32(d, 2H J=8.0Hz), 7.28(s, 4H), 6.99(s, 1H), 5.51-5.6(m, 1H), 4.45-4.53(m, 3H), 4.28-4.30(m, 1H), 4.07-4.14(m, 2H), 3.72-3.77(m, 4H), 2.85(s, 2H), 2.53(s, 1H), 2.27-2.35(m, 2H), 2.02-2.17(m, 3H), 1.62-1.74(m, 3H), 1.55-1.60(m, 2H). |
| 23 | 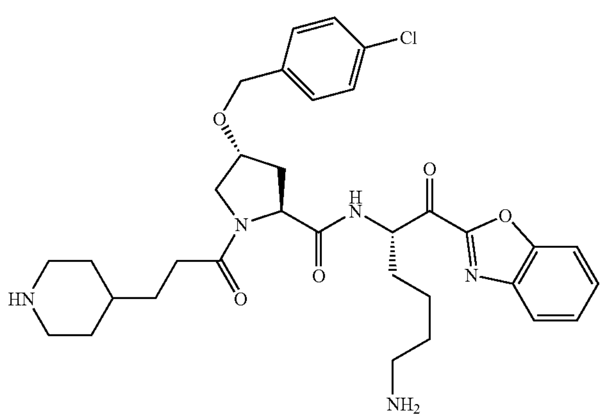 | MS m/z 624.3 (M + 1) |

TABLE 1-continued

| Example | Structure | Physical Data MS (m/z), Elemental Analysis, and $^1$H NMR 400 MHz (DMSO-$d_6$) |
|---|---|---|
| 24 | 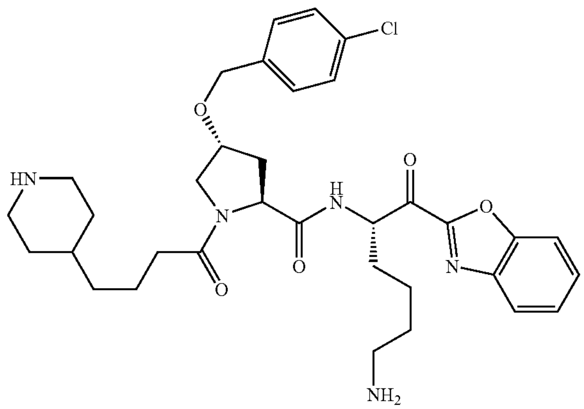 | MS m/z 638.3 (M + 1) |
| 25 | 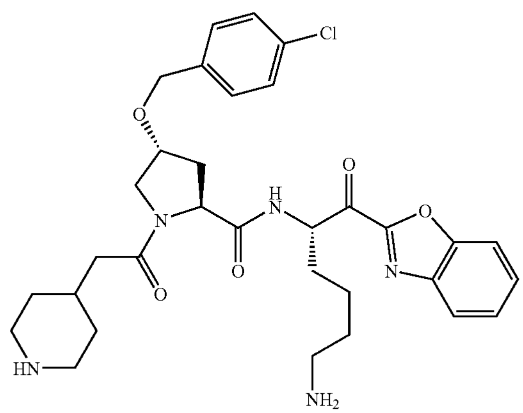 | MS m/z 610.3 (M + 1) |
| 26 | 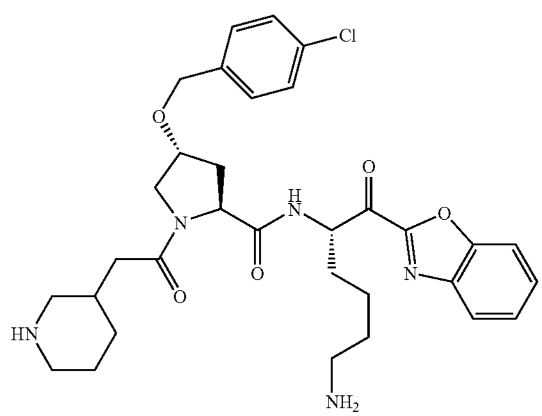 | MS m/z 610.3 (M + 1) |

TABLE 1-continued

| Example | Structure | Physical Data<br>MS (m/z), Elemental Analysis, and<br>¹H NMR 400 MHz (DMSO-d₆) |
| --- | --- | --- |
| 27 | 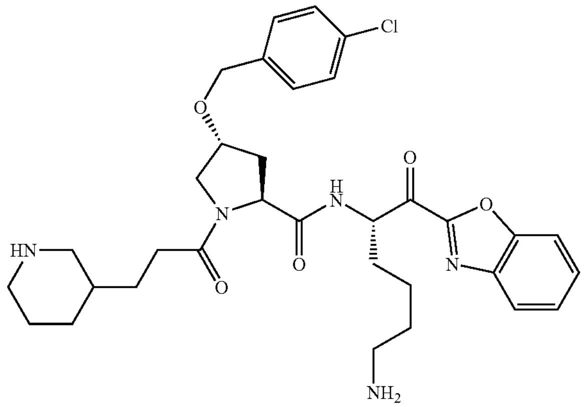 | MS m/z 624.3 (M + 1) |
| 28 | 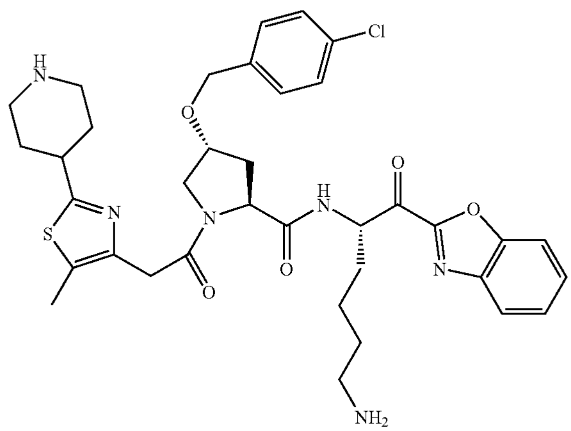 | MS m/z 707.3 (M + 1) |
| 29 | 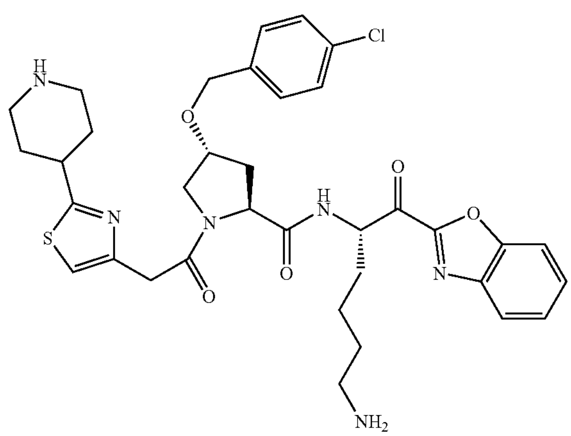 | MS m/z 693.3 (M + 1) |

| Example | Structure | Physical Data MS (m/z), Elemental Analysis, and ¹H NMR 400 MHz (DMSO-d$_6$) |
|---|---|---|
| 30 | 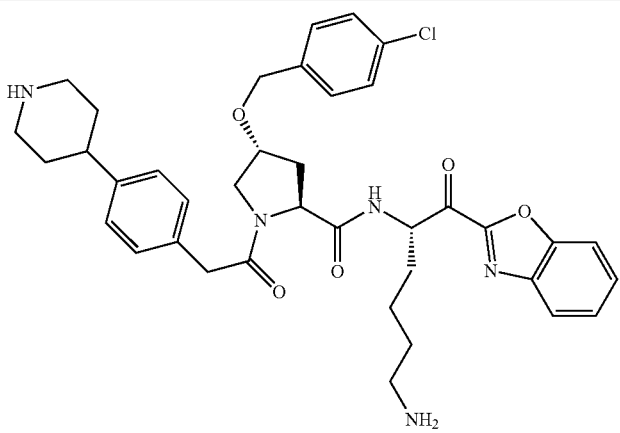 | MS m/z 686.3 (M + 1) |
| 31 | 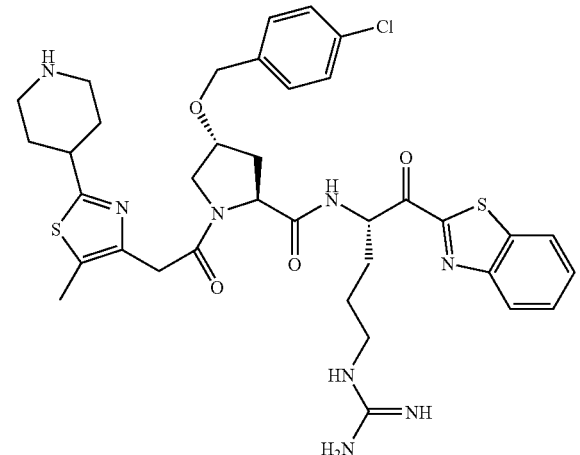 | MS m/z 651.3 (M + 1) |
| 32 | 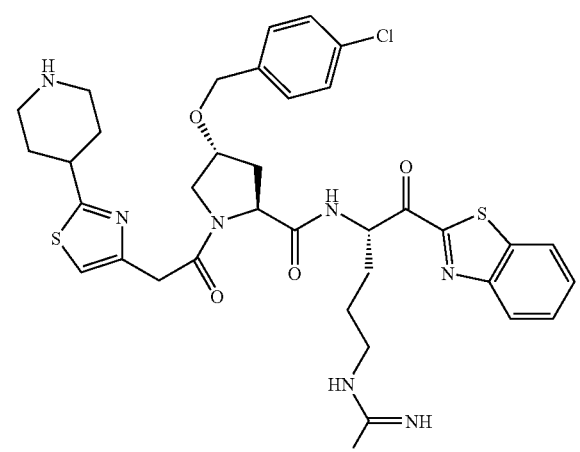 | MS m/z 637.3 (M + 1) |

TABLE 1-continued

| Example | Structure | Physical Data MS (m/z), Elemental Analysis, and ¹H NMR 400 MHz (DMSO-$d_6$) |
|---|---|---|
| 33 | 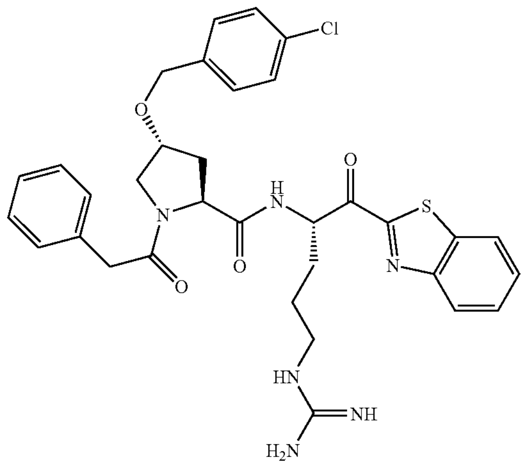 | MS m/z 647.2 (M + 1) |
| 34 | 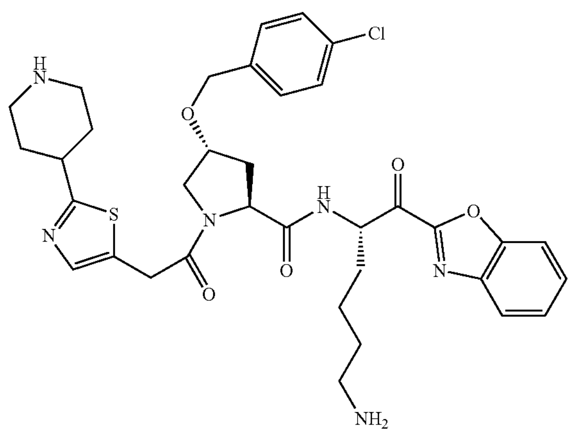 | MS m/z 693.3 (M + 1) |
| 35 | 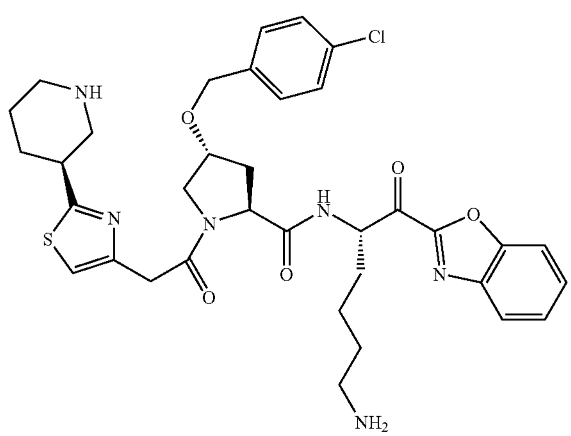 | MS m/z 693.3 (M + 1) |

TABLE 1-continued

| Example | Structure | Physical Data MS (m/z), Elemental Analysis, and $^1$H NMR 400 MHz (DMSO-$d_6$) |
|---|---|---|
| 36 | 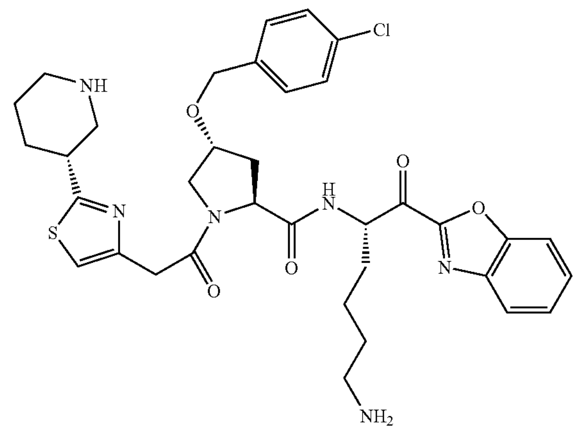 | MS m/z 693.3 (M + 1) |
| 37 | 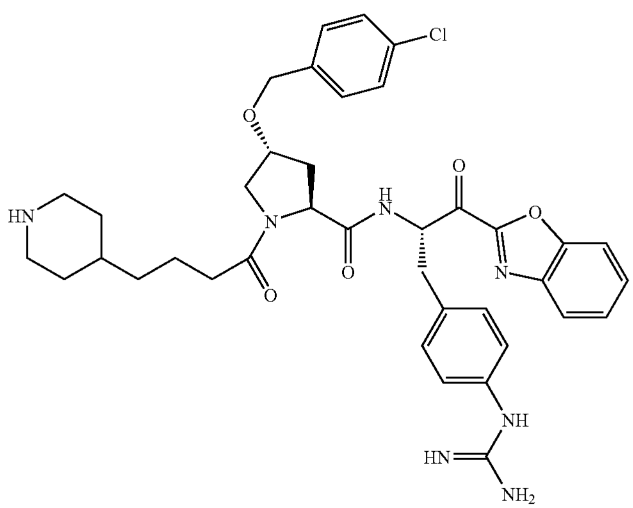 | MS m/z 714.3 (M + 1) |
| 38 | 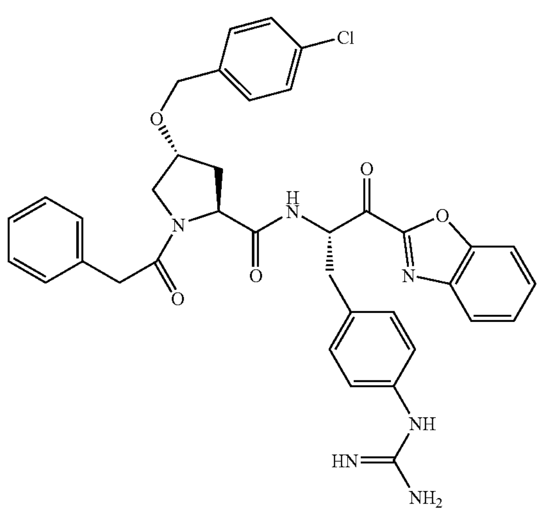 | MS m/z 679.2 (M + 1) |

TABLE 1-continued

| Example | Structure | Physical Data MS (m/z), Elemental Analysis, and $^1$H NMR 400 MHz (DMSO-$d_6$) |
|---|---|---|
| 39 | 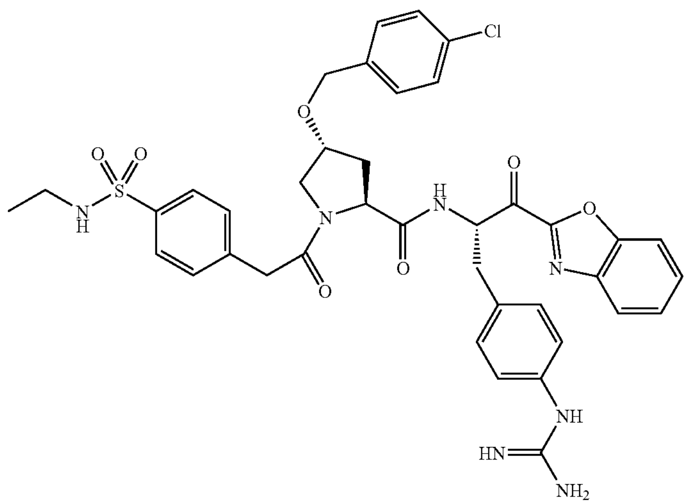 | MS m/z 686.2 (M + 1) |
| 40 | 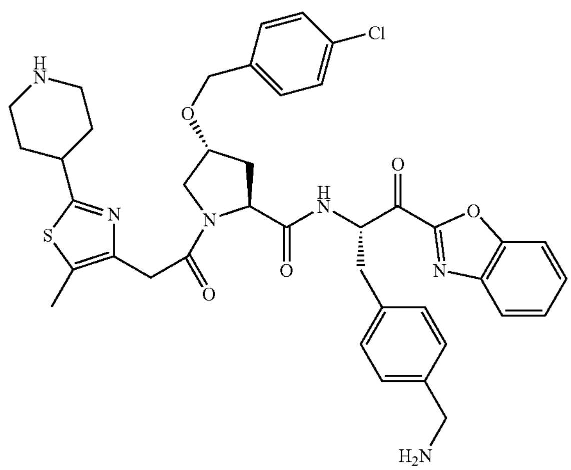 | MS m/z 755.3 (M + 1) |
| 41 | 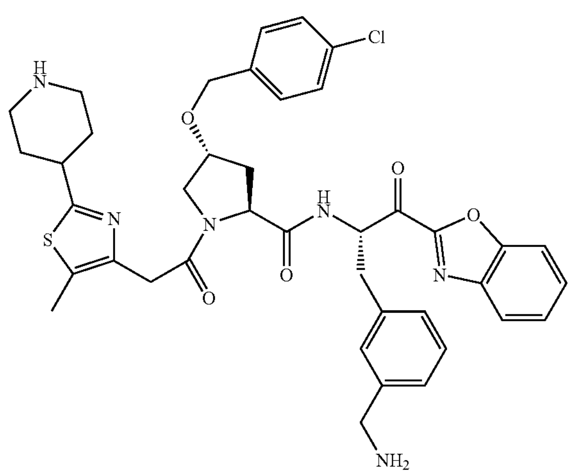 | MS m/z 755.3 (M + 1) |

TABLE 1-continued

| Example | Structure | Physical Data MS (m/z), Elemental Analysis, and ¹H NMR 400 MHz (DMSO-$d_6$) |
|---|---|---|
| 42 | 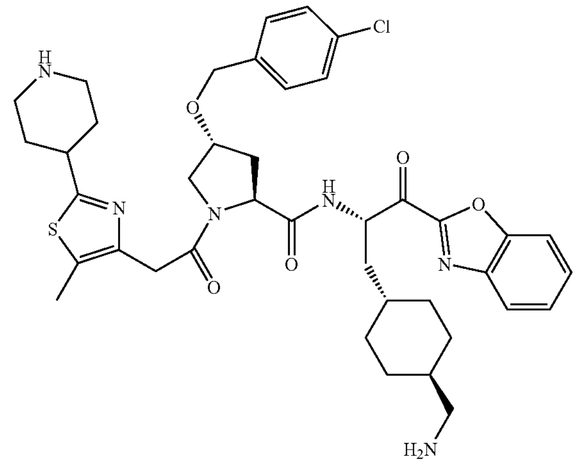 | MS m/z 761.3 (M + 1) |
| 43 | 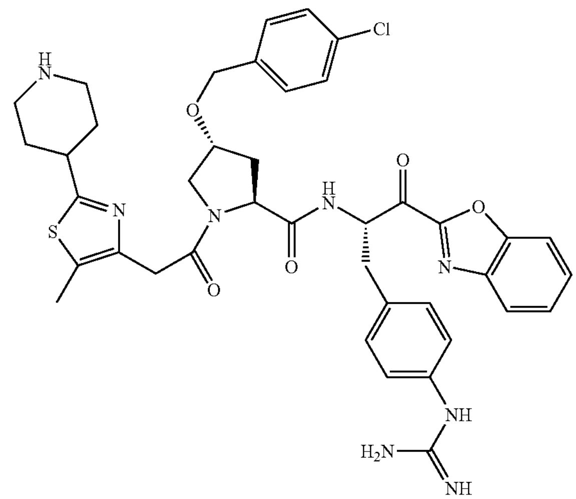 | MS m/z 783.3 (M + 1) |
| 44 | 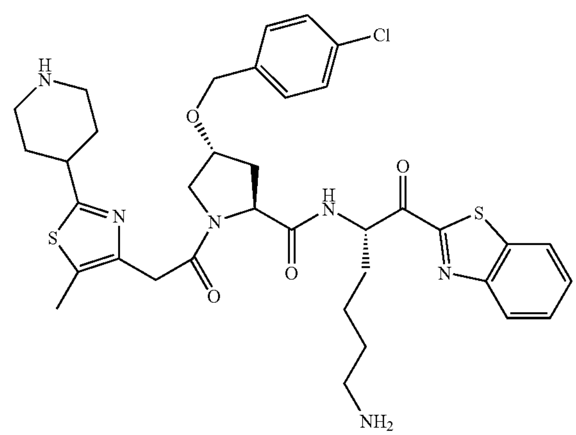 | MS m/z 723.3 (M + 1) |

TABLE 1-continued
| Example | Structure | Physical Data MS (m/z), Elemental Analysis, and ¹H NMR 400 MHz (DMSO-$d_6$) |
|---|---|---|
| 45 | 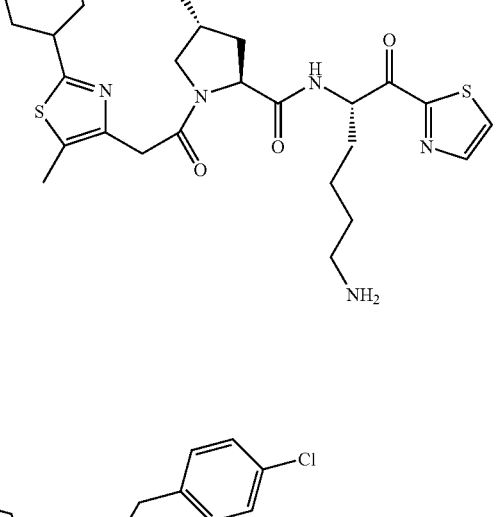 | MS m/z 723.3 (M + 1) |
| 46 | 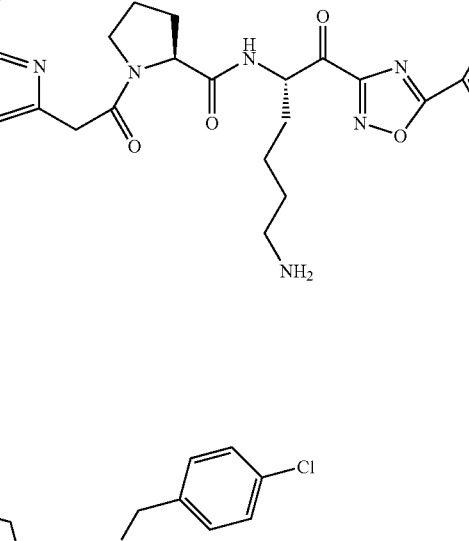 | MS m/z 734.3 (M + 1) |
| 47 | 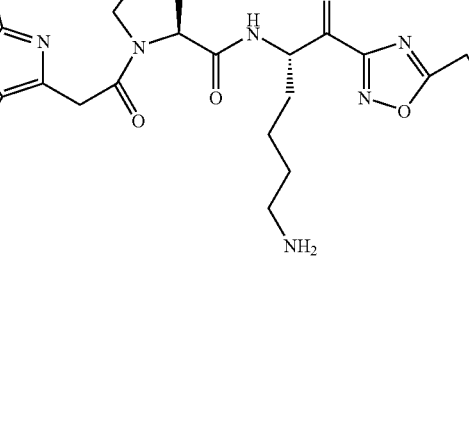 | MS m/z 740.4 (M + 1) |

TABLE 1-continued
| Example | Structure | Physical Data MS (m/z), Elemental Analysis, and $^1$H NMR 400 MHz (DMSO-$d_6$) |
|---|---|---|
| 48 | 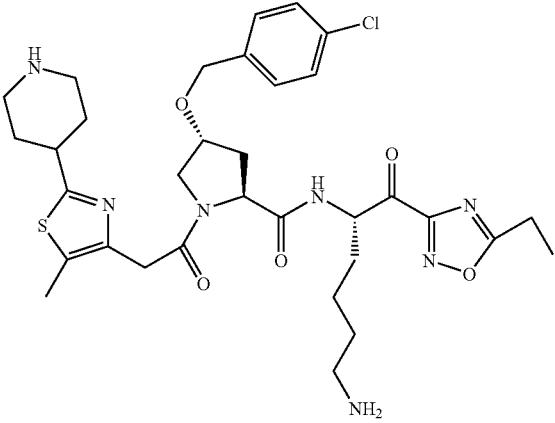 | MS m/z 686.3 (M + 1) |
| 49 | 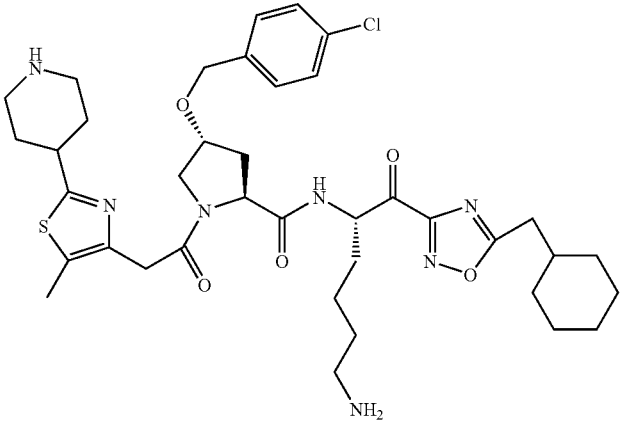 | MS m/z 754.4 (M + 1) |
| 50 | 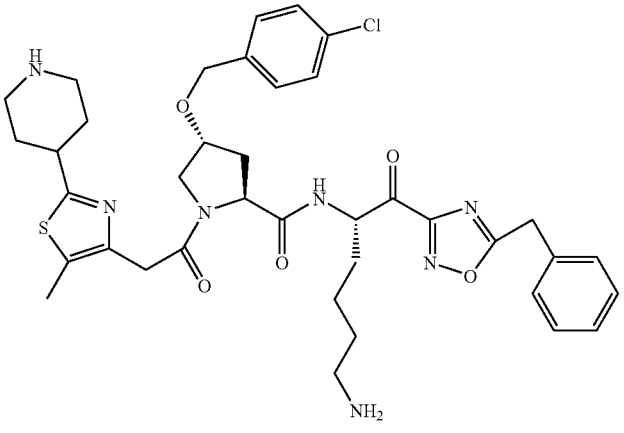 | MS m/z 748.4 (M + 1) |

Examples 51-53

Examples 51-53 in Table 2. are exemplary compounds of the invention having Formula (1) comprising 3-alkyl or 3-aryl substituted prolines, which may be prepared by repeating the procedures described in the above examples, using appropriate starting materials apparent to those skilled in the art.

TABLE 2

| Example | Structure | MS data |
|---|---|---|
| 51 | 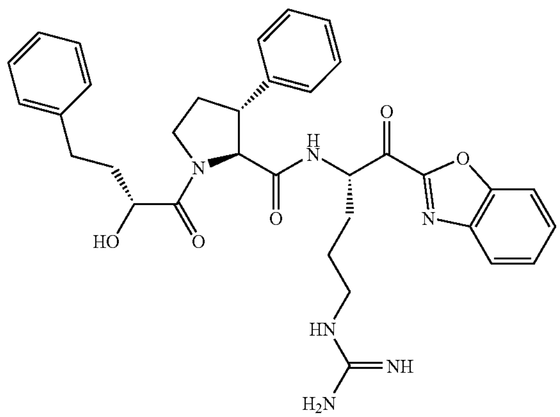 | MS m/z 611.3 (M + 1) |
| 52 | 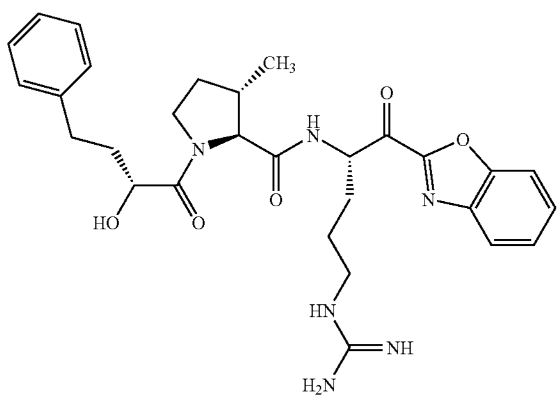 | MS m/z 549.3 (M + 1) |
| 53 | 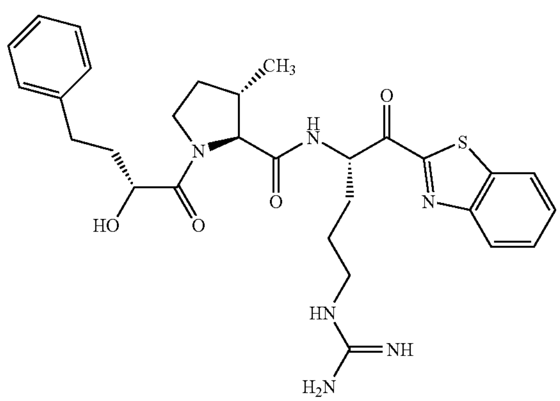 | MS m/z 565.3 (M + 1) |

Assays

The suitability of a channel activating protease inhibitor such as a prostasin inhibitor for the treatment of a disease mediated by inhibition of a channel activating protease, may be tested by determining the inhibitory effect of the channel activating protease inhibitor on: (1) the native, isolated, purified or recombinant channel activating protease, using a suitable biochemical assay format, using the method described in Shipway et al.; Biochem. Biophys. Res. Commun. 2004; 324(2):953-63); and/or (2) the ion channel/ion transport function in suitable isolated cells or confluent epithelia, using the methods described in Bridges et al.; Am. J. Physiol. Lung Cell Mol. Physiol. 2001; 281(1):L16-23; and Donaldson et al.; J. Biol. Chem. 2002; 277(10):8338-45.

Biochemical Assays

Recombinant human prostasin and matriptase and guinea pig prostasin are generated according to methods described in Shipway et al., Biochem. Biophys. Res. Commun. 2004; 324(2):953-63). The recombinant enzymes are incubated in an electrolyte buffer containing the test compounds or vehicle in a suitable multiple well assay plate such as a 96 or 384 well plate. At a defined time after the mixing of enzyme with compound or vehicle, a suitable fluorescent peptide substrate is added to the assay mixture. As substrate becomes cleaved by the active enzyme, fluorescence (measured, using a suitable fluorescence plate reader) increases and the rate of turnover of substrate (i.e. enzyme activity) may be quantified, and thus the inhibitory effect of any test compound. The efficacy of test compounds is expressed as the concentration that induces a 50% attenuation in the enzyme activity ($K_i$).

In general, compounds of the invention may have $K_i$ values from 0.1 nM to 5 µM. In some examples, compounds of the invention may have $K_i$ values from 0.1 nM to 500 nM; from 0.1 nM to 50 nM; from 0.1 nM to 5 nM; or from 0.1 nM to 0.5 nM. In particular examples, compounds of the invention may have $K_i$ values from 0.1 nM to 0.5 nM; from 0.5 nM to 5 nM; from 5 nM to 50 nM; from 50 nM to 500 nM; or from 500 nM to 5 µM. In yet other examples, compounds may have $K_i$ values less than 0.1 nM or more than 5 µM.

Epithelial Ion Transport

Human bronchial epithelial cells are cultured according to methods described in Danahay et al., Am. J. Physiol. Lung Cell Mol. Physiol. 2002; 282(2):L226-36). When suitably differentiated (days 14-21 after establishing an apical-air interface) epithelial cells are treated with either vehicle, aprotinin (200 µg/ml) or test compound for 90 minutes. Epithelia are then placed into, using Chambers as described in Danahay et al., Am. J. Physiol. Lung Cell Mol. Physiol. 2002; 282(2): L226-36) maintaining the concentration of vehicle, aprotinin or test compound on the apical side of the epithelia. Short circuit current (ISC) is then measured by voltage clamping the epithelia to zero millivolts. The amiloride-sensitive ISC is then measured by the addition of amiloride (10 µM) to the apical surface of the epithelia. The potency of the test compound is expressed as the concentration inducing a 50% inhibition of the total aprotinin-sensitive component of the amiloride-sensitive ISC.

In general, compounds of the invention may have $IC_{50}$ values from 1 nM to 10 µM. In some examples, compounds of the invention may have $IC_{50}$ values from 1 nM to 1 µM; or more particularly from 1 nM to 100 nM. In yet other examples, compounds of the invention may have $IC_{50}$ values from 100 nM to 1 µM, or from 1 µM to 10 µM. In yet other examples, compounds may have $IC_{50}$ values less than 1 nM or more than 10 µM.

Tracheal Potential Difference (In Vivo)

Guinea pigs are anaesthetized, using a short acting inhalation anaesthesia such as halothane and $N_2O$. While under short acting anaesthesia, an oral gavage needle is inserted into the trachea via the oropharangeal route. Once inside the trachea, a small volume (50-200 µl) of vehicle or test compound, in a suitable aqueous-based diluent, is instilled into the airways. Animals then recover and become fully ambulatory. Alternatively, test compounds may be administered to animals, using aerosol or dry powder dosing. At a defined time after dosing, the animals are surgically anaesthetized, using a suitable anaesthesia such as ketamine and xylazine. The trachea is then exposed and a plastic agar bridge electrode is inserted into the tracheal lumen. A reference electrode is also inserted into the layers of muscle in the animal's neck. The tracheal potential difference is then measured, using a suitable high impedance voltmeter as described in Takahashi et al., Toxicol Appl Pharmacol. 1995; 131(1):31-6. The potency of the test compound is expressed as the dose inducing a 50% reduction in the sensitive-component of the tracheal potential difference.

It is understood that the examples and embodiments described herein are for illustrative purposes only, and that various modifications or changes in light thereof will be suggested to persons skilled in the art and are to be included within the spirit and purview of this application and scope of the appended claims. All publications, patents, and patent applications cited herein are hereby incorporated by reference for all purposes.

The invention claimed is:
1. A compound of Formula (1):

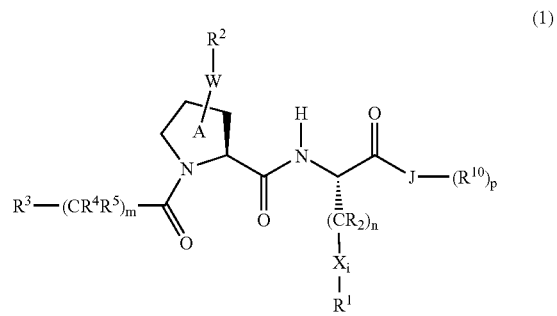

and pharmaceutically acceptable salts, and stereoisomers thereof, wherein

J is

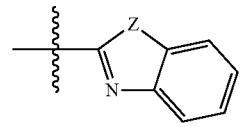

Z is O or S;
$R^1$ is —$(CR_2)_t$—$NR_2$, —$(CR_2)_t$—$NRC(=NR)$—$NR_2$, or —$(CR_2)_t$—$C(=NR)$—$NR_2$;
W—$R^2$ is a substituent at any position on ring A;
W is or —$O(CR_2)_k$—, —$S(CR_2)_k$—, —$S(O)(CR_2)_k$—, —$SO_2(CR_2)_k$— or —$OC(O)(CR_2)_k$—;
$R^2$ is $C_{1-6}$ alkyl, $C_{2-6}$ alkenyl, $C_{2-6}$ alkynyl, $R^6$, —$CR^9=CR^9$—$R^6$, or

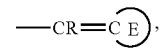

wherein ring E is an optionally substituted 5-7 membered monocyclic or fused carbocyclic or heterocyclic ring; or
W—$R^2$ together form $C_{1-6}$ alkyl, a 5-7 membered aryl or —$OC(O)NR^7R^8$;
$R^3$ is $NR^7R^8$ or $R^6$;
$R^4$ and $R^5$ are independently H, $C_{1-6}$ alkyl, OH, or $C_{1-6}$ alkoxy;
$R^7$ and $R^8$ are independently H, $C_{1-6}$ alkyl, $C_{2-6}$ alkenyl, $C_{2-6}$ alkynyl or —$(CR_2)_t$—$R^6$; or $R^7$ and $R^8$ together with N may form an optionally substituted 5-7 membered monocyclic or fused heterocyclic ring;
$R^9$ is H or $C_{1-6}$ alkyl;
$R^{10}$ is halo, $C_{1-6}$ alkyl, $C_{1-6}$ alkoxy, $OR^{11}$ or —$(CR_2)_t$—$R^{11}$;
$R^6$, $R^{11}$ and X are independently an optionally substituted 5-7 membered carbocyclic ring, heterocyclic ring, aryl or heteroaryl; or $R^{11}$ is H or $C_{1-6}$ alkyl;

R is H;
i is 0-1;
k and l are independently 0-6;
m and n are independently 1-6; and
p is 0-3.

2. The compound of claim 1, wherein $R^1$ is —$(CH_2)_l$—$NH_2$, —$(CH_2)_l$—$NHC(=NH)$—$NH_2$ or —$(CH_2)_l$—$C(=NH)$—$NH_2NH_2$, wherein each l is 0-1.

3. The compound of claim 1, wherein W is —$O(CR_2)_k$—, —$S(CR_2)_k$—, —$S(O)(CR_2)_k$—, —$SO_2(CR_2)_k$— or —$OC(O)(CR_2)_k$—; and k is 1.

4. The compound of claim 1, wherein $R^2$ is an optionally substituted phenyl, $C_{5-7}$ cycloalkyl, thienyl, furanyl, piperidinyl, methylenecyclohexyl,

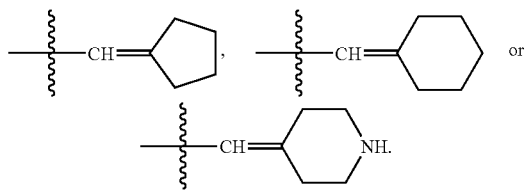

or

5. The compound of claim 1, wherein $R^3$ is an optionally substituted phenyl, pyridyl, thiazolyl, piperidinyl, or $NR^7R^8$; wherein $R^7$ and $R^8$ are both H, or $R^7$ and $R^8$ together with N form an optionally substituted piperidinyl.

6. The compound of claim 1, wherein R, $R^4$, $R^5$, $R^7$ and $R^8$ are each H.

7. The compound of claim 1, wherein $R^6$ is an optionally substituted phenyl,
  $C_{3-7}$ cycloalkyl, pyridyl, thiazolyl, piperidinyl, cyclohexanol, imidazolyl, thienyl, furanyl,

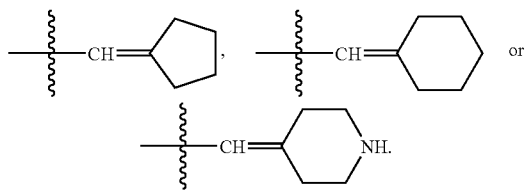

or

8. The compound of claim 1, wherein X is cyclohexyl, phenyl or piperidinyl.

9. The compound of claim 1, wherein J is benzothiazolyl, or benzoxazolyl.

10. The compound of claim 1, wherein said compound is of Formula (2A) or (2B):

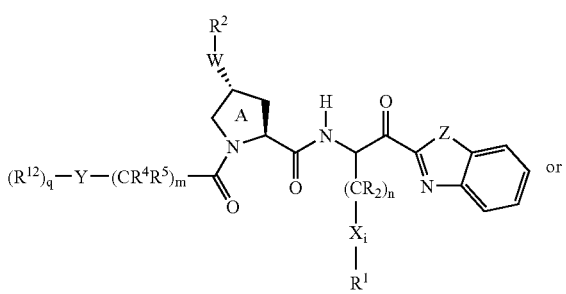

(2A)

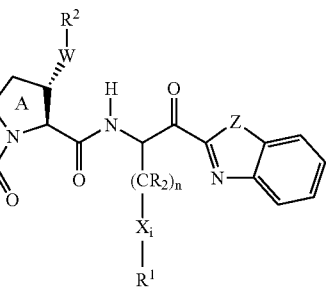

(2B)

wherein Z is O or S;
$R^1$ is $NH_2$, —$NHC(=NH)$—$NH_2$ or —$C(=NH)$—$NH_2$;
W is —$O(CH_2)_k$— or —$S(O)(CH_2)_k$—;
$R^2$ is an optionally substituted phenyl, or W—$R^2$ together form $C_{1-6}$ alkyl or an optionally substituted phenyl;
R, $R^4$ and $R^5$ are independently H;
Y is a 5-7 membered aryl, heteroaryl or heterocyclic ring containing N, O or S;
$R^{12}$ is halo, $C_{1-6}$ alkyl or -L-$(CH_2)_l$—$R^{13}$;
L is a bond, O, $SO_2$, NHCO, $NHSO_2$ or $SO_2NH$;
$R^{13}$ is optionally halogenated $C_{1-6}$ alkyl, or an optionally substituted $C_{3-7}$ cycloalkyl, or 5-7 membered aryl, heteroaryl or heterocyclic ring;
i is 0;
k is 1;
l is 0-1;
m and n are independently 1-4; and
q is 0-3.

11. The compound of claim 10, wherein Y is phenyl, pyridyl, thiazolyl or piperidinyl.

12. The compound of claim 10, wherein $R^{12}$ is -L-$(CH_2)_l$—$R^{13}$; and $R^{13}$ is an optionally halogenated $C_{1-6}$ alkyl, $C_{3-7}$ cycloalkyl, morpholinyl, phenyl or piperidinyl.

13. The compound of claim 1, wherein said compound is selected from the group consisting of:

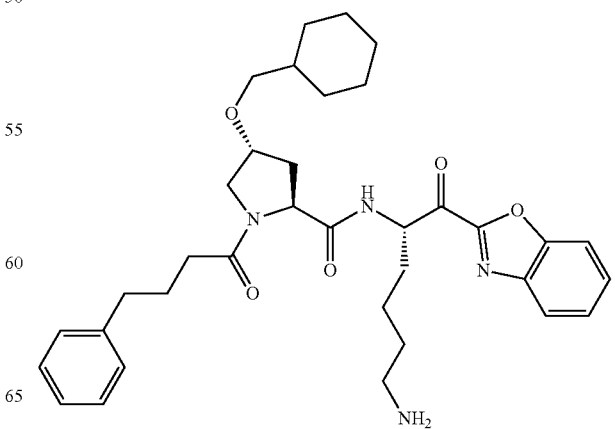

1

85
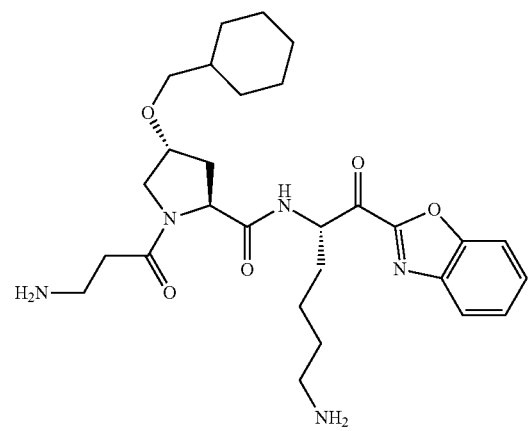
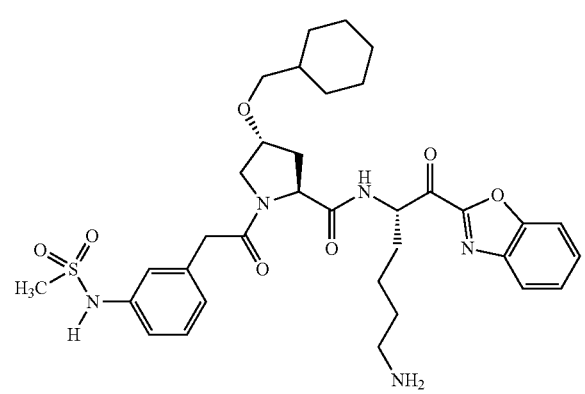
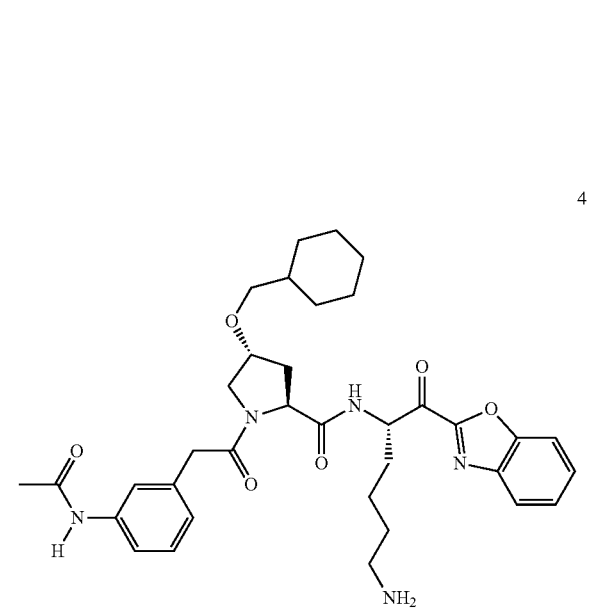
86
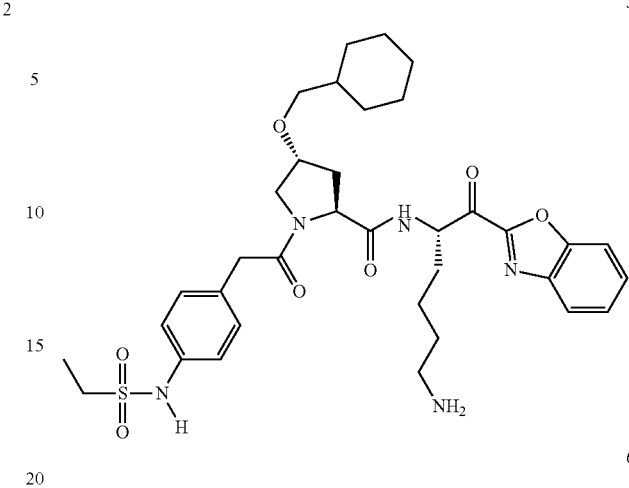
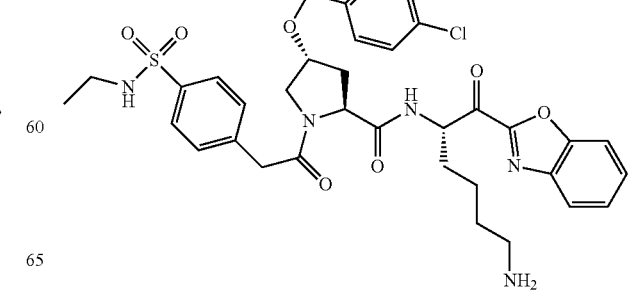

9
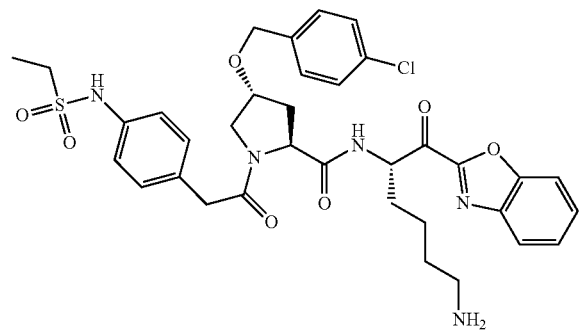
10
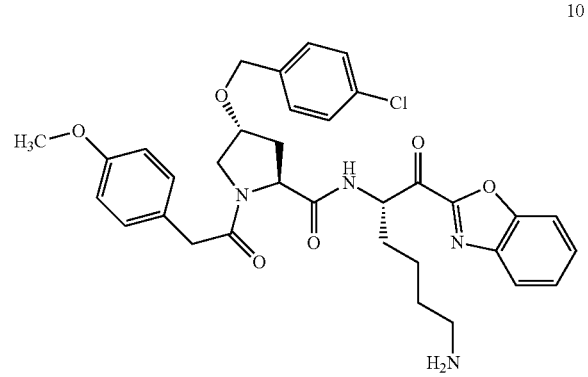
11
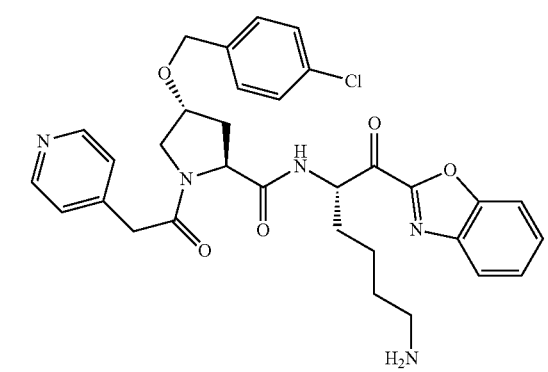
12
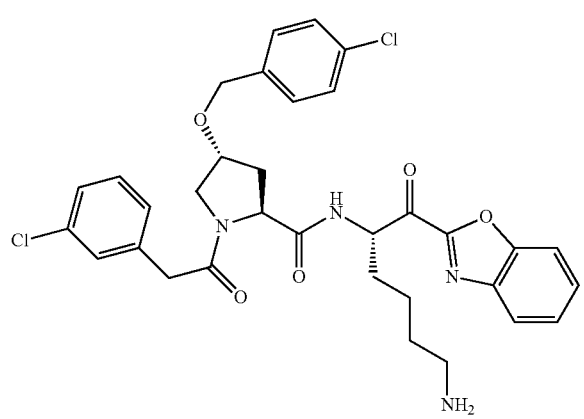
13
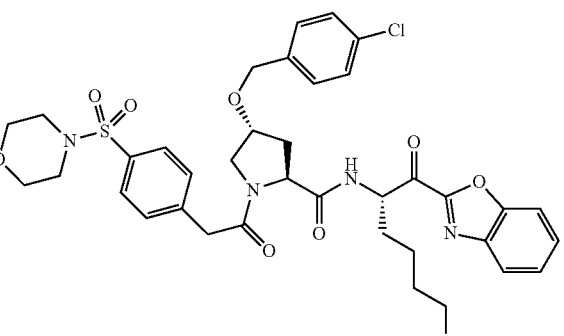
14
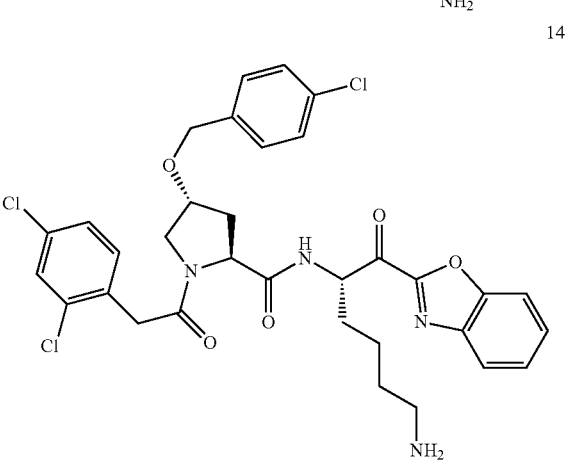
15
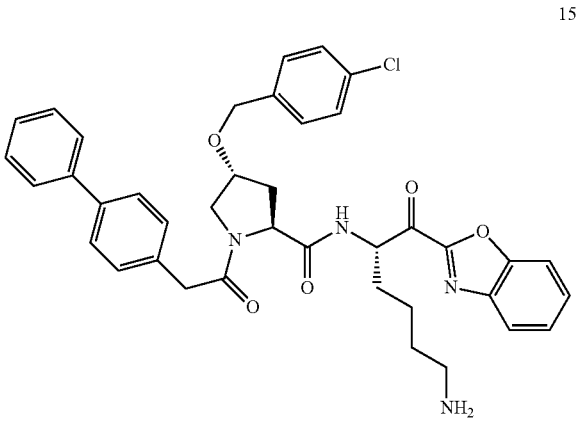
16

| 89 | 90 |
|---|---|
| -continued | -continued |
17
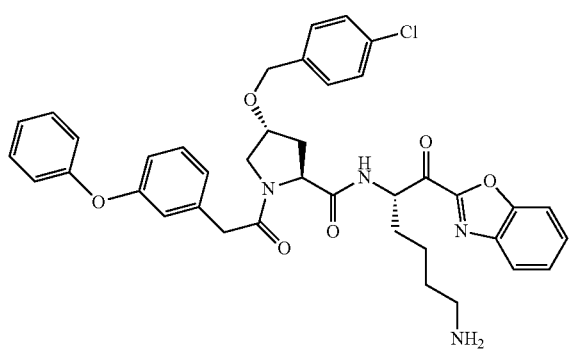
18
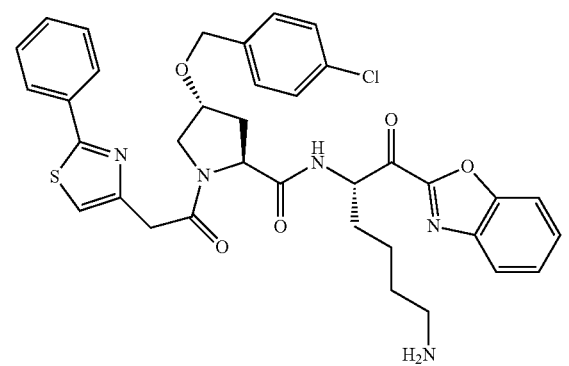
19
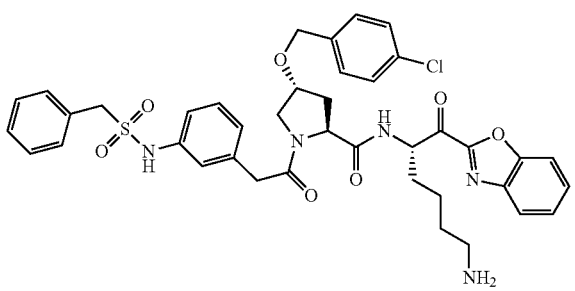
20
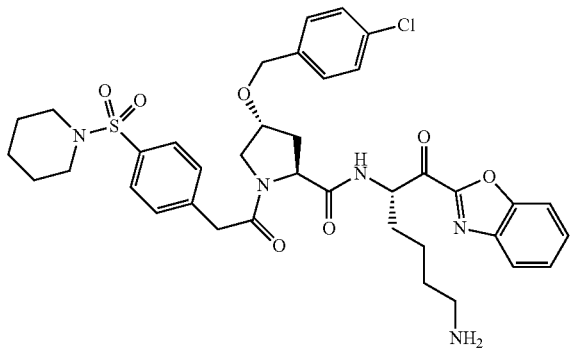
21
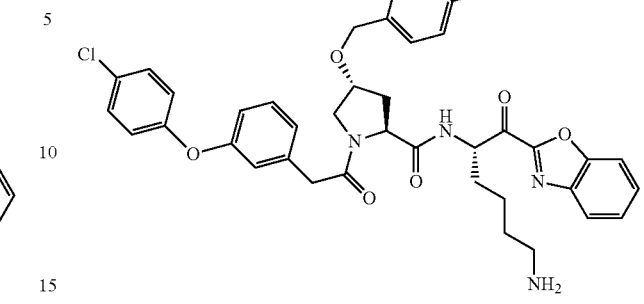
22
23
24
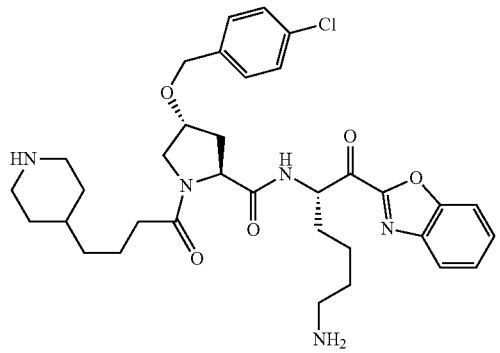

91
25
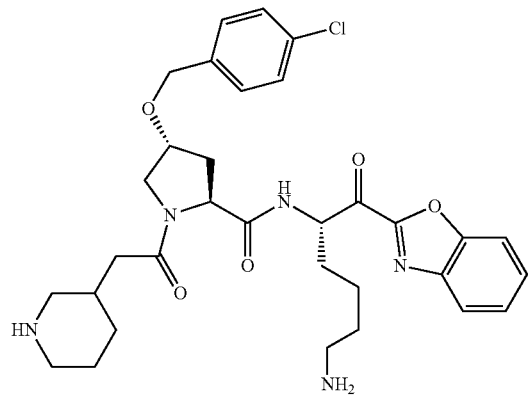
26
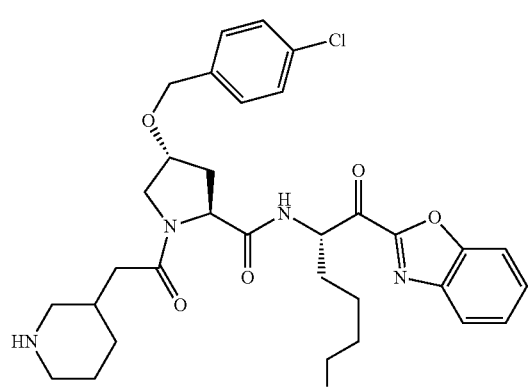
27
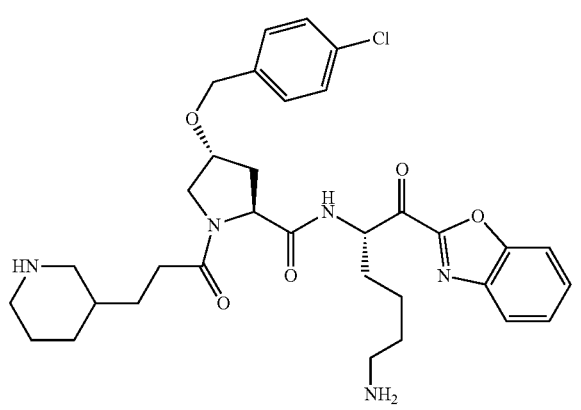
92
28
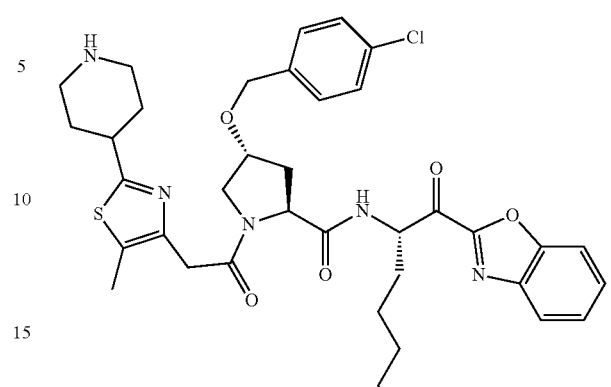
29
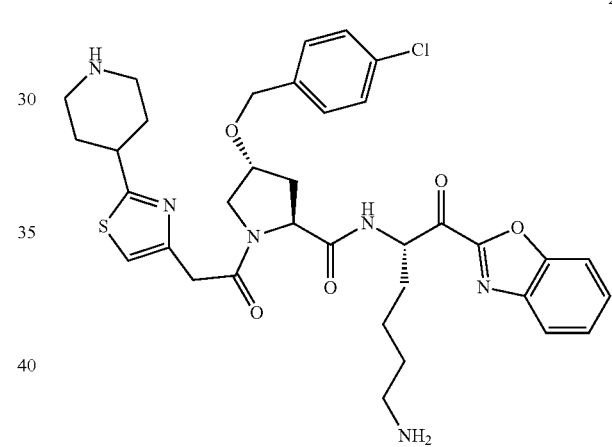
30
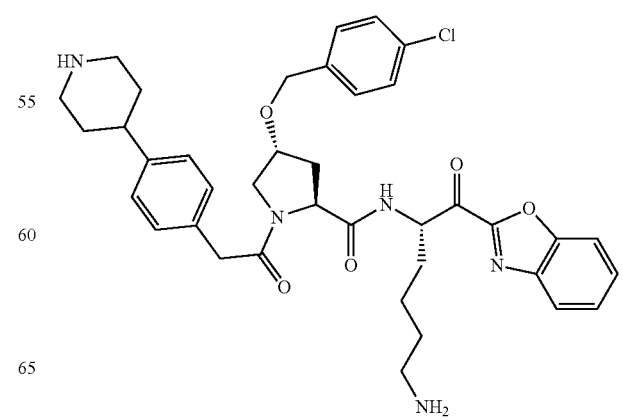

93
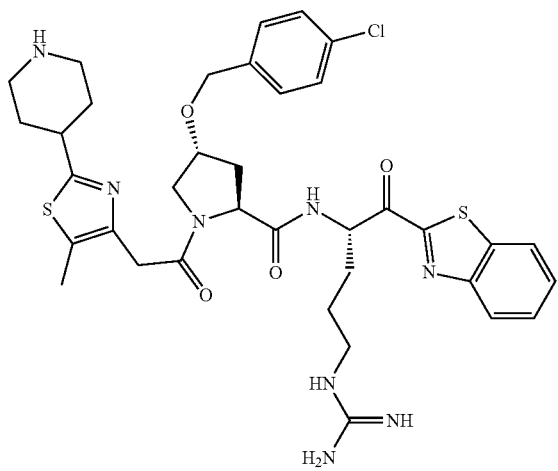
31
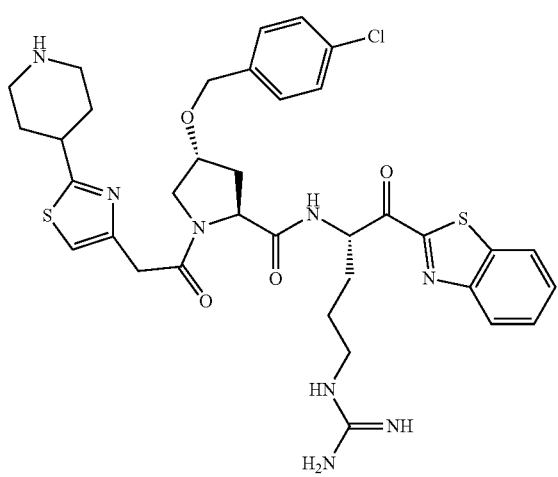
32
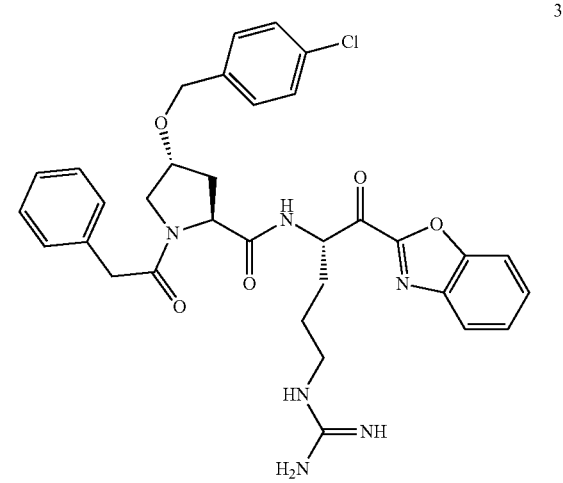
33
94
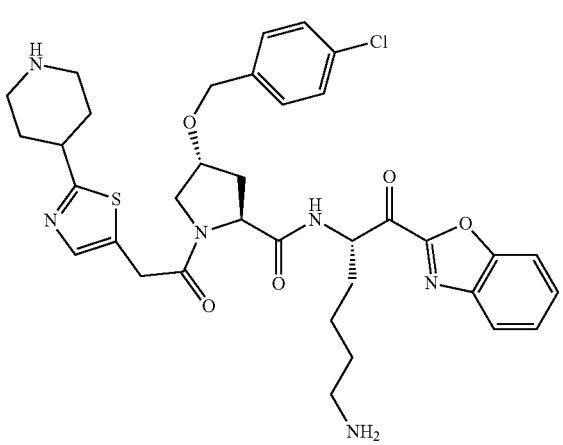
34
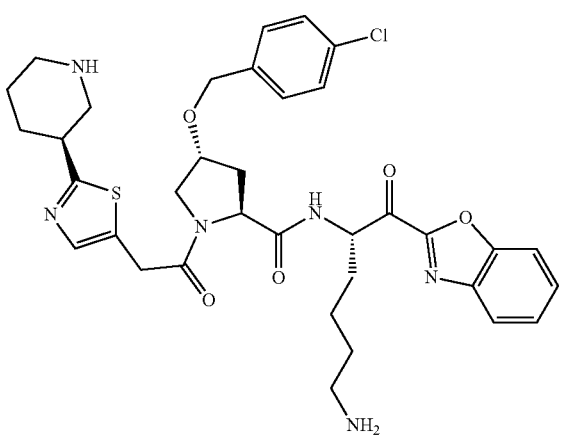
35
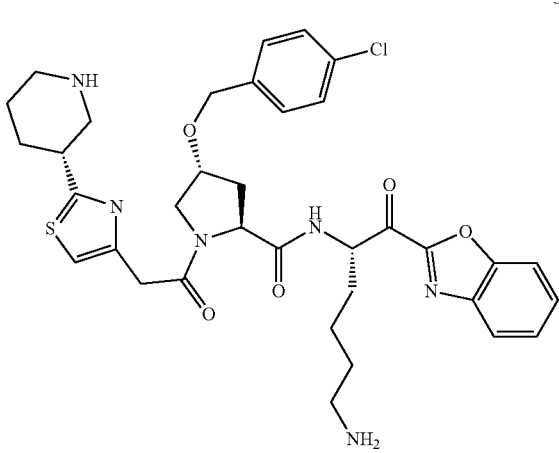
36

37
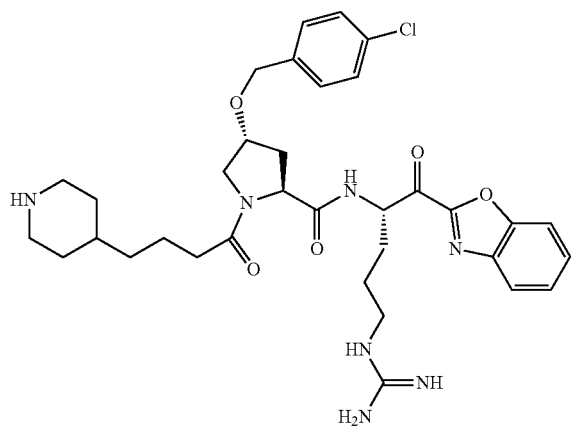
38
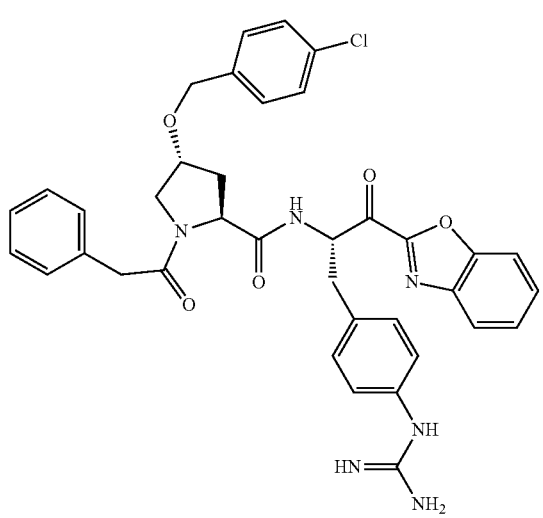
39
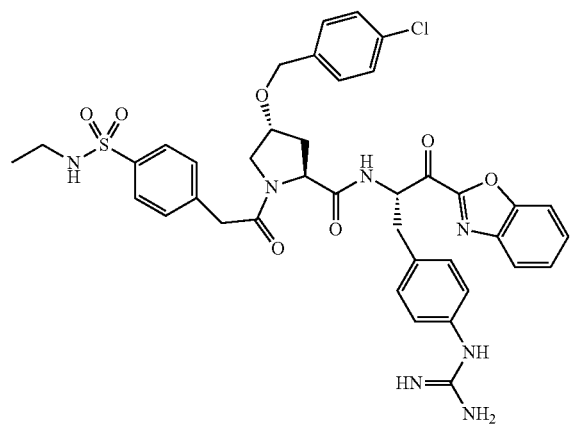
40
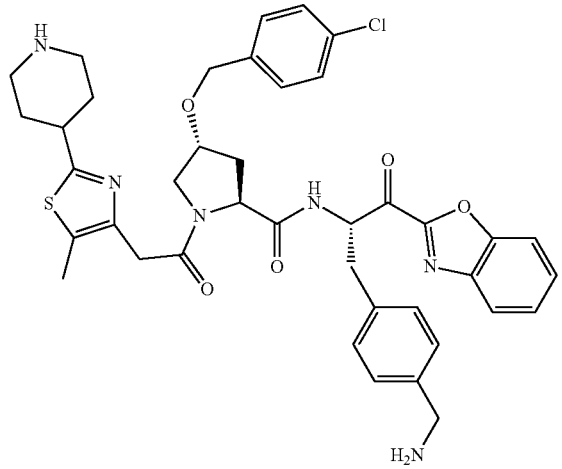
41
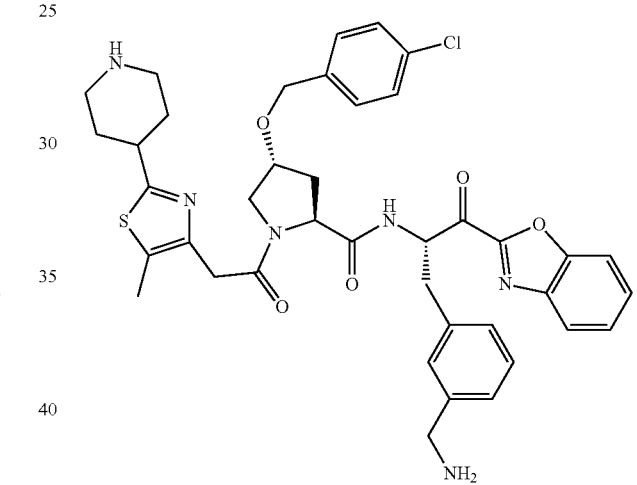
42
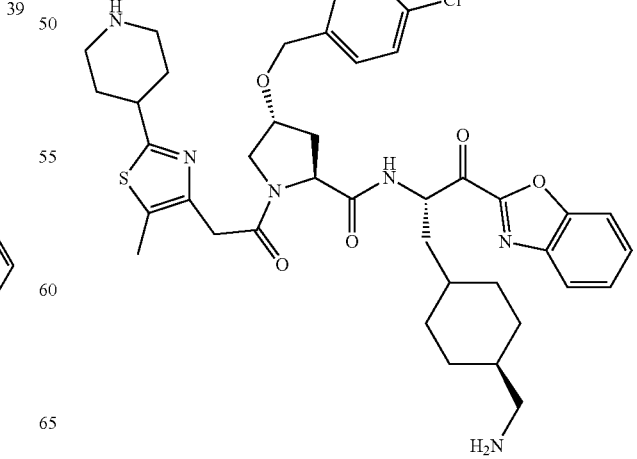

43

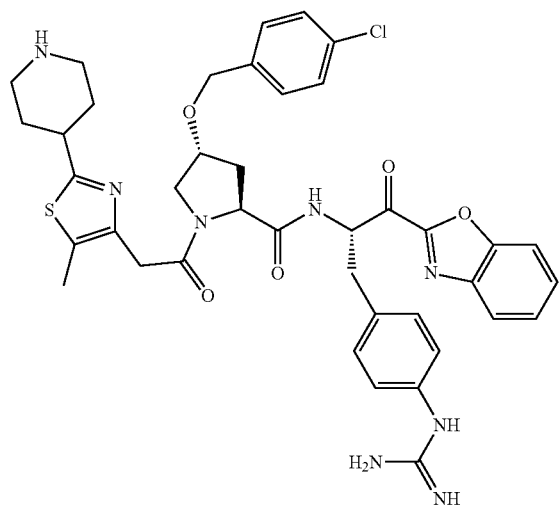

44

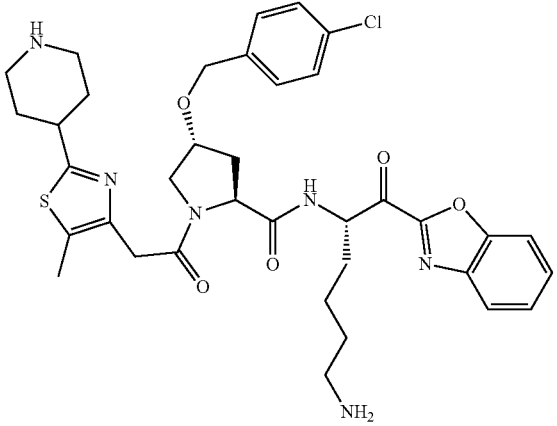

51

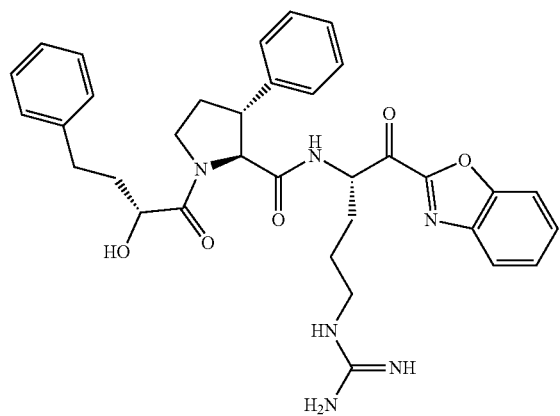

52

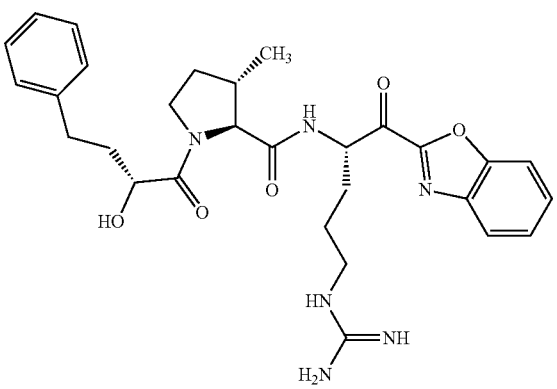

53

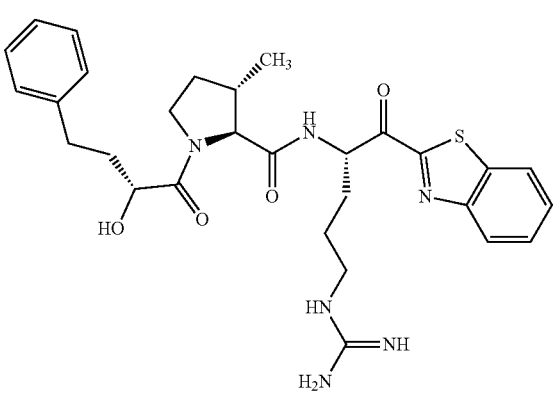

or pharmaceutically acceptable salts thereof.

14. A pharmaceutical composition comprising a therapeutically effective amount of a compound of claim 1 and a pharmaceutically acceptable excipient.

15. A method for inhibiting a channel activating protease selected from prostasin or trypsin, comprising administering to a subject, a cell, or a tissue, in need thereof, a therapeutically effective amount of the compound of claim 1 or pharmaceutically acceptable salts or pharmaceutical compositions thereof, thereby inhibiting said channel activating protease.

16. The method of claim 15, wherein the subject is a human or animal.

17. The method of claim 15, wherein said cell is bronchial epithelial cell.

* * * * *